(12) United States Patent  
Brown et al.

(10) Patent No.: US 8,629,143 B2
(45) Date of Patent: Jan. 14, 2014

(54) POTASSIUM CHANNEL MODULATORS

(75) Inventors: Brian S. Brown, Evanston, IL (US); Tongmei Li, Lake Bluff, IL (US); Arturo Perez-Medrano, Grayslake, IL (US); Sridhar Peddi, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 12/949,435

(22) Filed: Nov. 18, 2010

(65) Prior Publication Data

US 2011/0124642 A1 May 26, 2011

Related U.S. Application Data

(60) Provisional application No. 61/264,337, filed on Nov. 25, 2009.

(51) Int. Cl.
*A01N 43/58* (2006.01)
*A61K 31/50* (2006.01)
*C07D 237/26* (2006.01)
*C07D 487/00* (2006.01)

(52) U.S. Cl.
USPC ............ 514/250; 514/249; 544/235; 544/236

(58) Field of Classification Search
USPC ........... 544/235, 236; 514/248, 235, 249, 250
See application file for complete search history.

(56) References Cited

U.S. PATENT DOCUMENTS

| | | |
|---|---|---|
| 6,180,629 B1 | 1/2001 | Wang et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 2007/0082909 A1 | 4/2007 | Johnson et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |

FOREIGN PATENT DOCUMENTS

| | | |
|---|---|---|
| WO | WO9507271 A1 | 3/1995 |
| WO | WO9710223 A1 | 3/1997 |
| WO | WO2005099353 A2 | 10/2005 |
| WO | WO2006008754 A | 1/2006 |

OTHER PUBLICATIONS

El-Shenawy et al., Synthesis and reactions of 4-(3,4-dimethylphenyl)-5,6,7,8-tetrabromobenz[d][2,3]oxazin-1-one Egyptian Journal of Chemistry (2004), 47(2), 241-246 CODEN: EGJCA3; ISSN: 0449-2285; English Synthesis and reactions of 5,6,7,8-tetrabromo-4-(3,4-dimethylphenyl)-1H-2,3-benzoxazin-1-one Chemical Papers (2004), 58(3), 205-208 CODEN: CHPAE.*
Yassin et al., Synthesis and reactions of 2-amino-4-(substituted phenyl)-5,6,7,8-tetrabromo-1(2H)-phthalazinone derivatives Pakistan Journal of Scientific and Industrial Research (1994), 37(12), 508-11 CODEN: PSIRAA; ISSN: 0030-9885.*
Tamura et al.,Chemical properties of N-benzoylimines of quinazoline, quinoxaline, and phthalazine Journal of Heterocyclic Chemistry (1976), 13(1), 23-8 CODEN: JHTCAD; ISSN: 0022-152X; English.*
Bennett G.J., et al., "A Peripheral Mononeuropathy in Rat that Produces Disorders of Pain Sensation like those Seen in Man," Pain, 1988, vol. 33 (1), pp. 87-107.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blackburn-Munro G., et al., "Retigabine: Chemical Synthesis to Clinical Application," CNS Drug Reviews, 2005, vol. 11 (1), pp. 1-20.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Chaplan S.R., et al., "Quantitative Assessment of Tactile Allodynia in the Rat Paw," Journal of Neuroscience Methods , 1994, vol. 53, pp. 55-63.
Coates W.J., "Reinvestigation and Extension of the Aluminum Chloride Induced Reactions of Resorcinol and Hydroquinone with 3,6-Dichloropyridazine," The Journal of Organic Chemistry , 1990, vol. 55 (19), pp. 5418-5420.

(Continued)

*Primary Examiner* — Paul V. Ward

(57) ABSTRACT

Disclosed herein are KCNQ potassium channels modulators of formula (I)

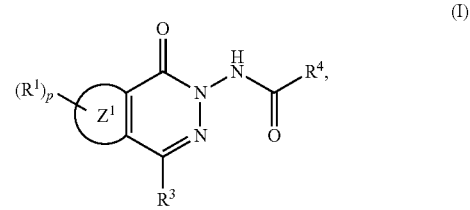

wherein ring $Z^1$, $R^1$, p, $R^3$, and $R^4$ are as defined in the specification. Compositions comprising such compounds; and methods for treating conditions and disorders using such compounds and compositions are also described.

23 Claims, No Drawings

(56) References Cited

OTHER PUBLICATIONS

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Dalby-Brown W., et al., "K(V)7 Channels: Function, Pharmacology and Channel Modulators," Current Topics in Medicinal Chemistry, 2006, vol. 6 (10), pp. 999-1023.

Dixon W.J., "Efficient Analysis of Experimental Observations," Annual Review of Pharmacology and Toxicology, 1980, vol. 20, pp. 441-462.

Eigenmann G.W., et al., "Stereospecific Hydrogenation of a-Pinene Derivatives," Journal of the American Chemical Society, 1959, vol. 81, pp. 3440-3442.

Foster, A. B. et al., "Deuterium Isotope Effects in the Metabolism of Drugs and Xenobiotics: Implications for Drug Design," Advances in Drug Research, 1985, vol. 14, pp. 2-36.

Greene, T.W., et al., Protective Groups in Organic Synthesis, 3rd Edition, John Wiley and Sons, Inc., 1999, Table of Contents.

Hansen H.H., et al., "Kv7 Channels: Interaction with Dopaminergic and Serotonergic Neurotransmission in the CNS," The Journal of Physiology, 2008, vol. 586 (7), pp. 1823-1832.

Hansen H.H., et al., "The KCNQ Channel Opener Retigabine Inhibits the Activity of Mesencephalic Dopaminergic Systems of the Rat," The Journal of Pharmacology and Experimental Therapeutics, 2006, vol. 318 (3), pp. 1006-1019.

Jentsch T.J., "Neuronal KCNQ Potassium Channels: Physiology and Role in Disease," Nature Reviews Neuroscience, 2000, vol. 1 (1), pp. 21-30.

Joshi S. K., et al., "Comparison of Antinociceptive Actions of Standard Analgesics in Attenuating Capsaicin and Nerve-Injury-Induced Mechanical Hypersensitivity ," Neuroscience, 2006, vol. 143, pp. 587-596.

Kato, S. et al., "Synthesis of Deuterated Mosapride Citrate," Journal of Labelled Compounds and Radiopharmaceuticals, 1995, vol. 36 (10), pp. 927-932.

Kim S.H., et al., "An Experimental Model for Peripheral Neuropathy Produced by Segmental Spinal Nerve Ligation in the Rat," Pain, 1992, vol. 50 (3), pp. 355-363.

Klotzer W., et al., "Electrophilic N-Amination of Imide Sodium Salts With O-Diphenylphosphinylhydroxylamine (Dph): 7-Aminotheophylline," Organic Syntheses, 1986, vol. 64, pp. 96.

Kushner et al., "Pharmacological uses and perspectives of heavy water and deuterated compounds," Canadian Journal of Physiology and Pharmacology, 1999, vol. 77 (2), pp. 79-88.

Lizondo, J. et al., "Linezolid: Oxazolidinone antibacterial," Drugs of the Future, 1996, vol. 21 (11), pp. 1116-1123.

Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

March J., "Reactions, Mechanisms, and Structure" in: Advanced Organic Chemistry, 4th Edition, John Wiley & Sons, 1992, pp. 1161-1171.

March J., "Reactions, Mechanisms, and Structure" in: Advanced Organic Chemistry, 4th Edition, John Wiley & Sons, 1992, pp. 539-542.

Matulenko M.A. et al., "5-(3-Bromophenyl)-7-(6-morpholin-4-ylpyridin-3-yl)pyrido- [2,3-d]pyrimidin-4-ylamine: structure-activity relationships of 7-substituted heteroaryl analogs as non-nucleoside adenosine kinase inhibitors," Bioorganic & Medicinal Chemistry, 2005, vol. 13 (11), pp. 3705-3720.

Miceli F., et al., "Molecular Pharmacology and Therapeutic Potential of Neuronal Kv7- Modulating Drugs," Current Opinion in Pharmacology , 2008, vol. 8 (1), pp. 65-74.

Munro G., et al. , "Kv7 (KCNQ) Channel Modulators and Neuropathic Pain," Journal of Medicinal Chemistry, 2007, vol. 50 (11), pp. 2576-2582.

Poste G. et al., "Lipid Vesicles as Carriers for Introducing Biologically Active Materials into Cells," Methods in Cell Biology, 1976, vol. 14, pp. 33-71.

Roeloffs R., et al., "In Vivo Profile of ICA-27243 [N-(6-Chloropyridin-3-yl)-3,4-difluoro-benzamide], a Potent and Selective KCNQ2/Q3(Kv7.2/Kv7.3) Activator in Rodent Anticonvulsant Models," The Journal of Pharmacology and Experimental Therapeutics, 2008, vol. 326 (3), pp. 818-828.

Roza C., et al., "Retigabine, the Specific KCNQ Channel Opener, Blocks Ectopic Discharges in Axotomized Sensory Fibres," Pain, 2008, vol 138 (3), pp. 537-545.

Sotty F., et al., "Antipsychotic-Like Effect of Retigabine [N-(2-Amino-4- (Fluorobenzylamino)-Phenyl)Carbamic Acid Ester], A Kcnq Potassium Channel Opener, Via Modulation of Mesolimbic Dopaminergic Neurotransmission," The Journal of Pharmacology and Experimental Therapeutics, 2009, vol. 328 (3), pp. 951-962.

Streng T., et al., "Urodynamic Effects of the K+ Channel (KCNQ) Opener Retigabine in Freely Moving, Conscious Rats ," The Journal of Urology, 2004, vol. 172 (5 pt 1), pp. 2054-2058.

Thomson, J.F., "Physiological Effects of D20 in Mammals," Annals of the New York Academy of Sciences, 1960, vol. 84, pp. 736-744.

Villemin D., et al., "Isonitriles as efficient ligands in Suzuki-Miyaura reaction," Tetrahedron Letters, 2007, vol. 48, pp. 4191-4193.

Wickenden A.D., et al., "Retigabine, A Novel Anti-Convulsant, Enhances Activation of KCNQ2/Q3 Potassium Channels," Molecular Pharmacology, 2000, vol. 58 (3), pp. 591-600.

Wu, Y.J., et al., "Fluorine Substitution Can Block Cyp3a4 Metabolism-Dependent Inhibition: Identification of (S)-N-[1-(4-Fluoro-3-Morpholin-4-Ylphenyl)Ethyl]-3- (4-Fluorophenyl)Acrylamide as an Orally Bioavailable KCNQ2 Opener Devoid of Cyp3a4 Metabolism-Dependent Inhibition," The Journal of Medicinal Chemistry, 2003, vol. 46 (18), pp. 3778-3781.

Wu Y.J., et al., "(S)-N-[1-(3-Morpholin-4-Ylphenyl)Ethyl]-3-Phenylacrylamide: An Orally Bioavailable KCNQ2 Opener with Significant Activity in a Cortical Spreading Depression Model of Migraine," The Journal of Medicinal Chemistry, 2003, vol. 46 (15), pp. 3197-3200.

Amine M.S., "Synthesis and Reactions of 1-(p-Tolyl)-5,6,7,8-Tetrabromo-3,2-Benzoxazin-4-One," Asian Journal of Chemistry, 1992, vol. 4 (4), pp. 865-872.

El-Shenawy A.L., "Synthesis and Reactions of 5,6,7,3-Tetrabromo-4-(3,4- dimethylphenyl)-H-2,3-benzoxazin-1-one," Chemical Papers, 2004, vol. 58 (3), pp. 205-208.

Tamura Y., et al., "Chemical Properties of N-Benzoylimines of Quinazolinc,Quinoxaline, and Plithalazine," Journal of Hetero Chemistry, 1976, vol. 13, pp. 23-28.

* cited by examiner

POTASSIUM CHANNEL MODULATORS

CROSS REFERENCE TO RELATED APPLICATIONS

This application claims priority to U.S. Patent Application Ser. No. 61/264,337, filed Nov. 25, 2009, which is incorporated herein by reference in its entirety.

TECHNICAL FIELD

Compounds that are potassium channel modulators, compositions comprising such compounds, and methods of treating conditions and disorders using such compounds and compositions are disclosed.

BACKGROUND OF THE INVENTION

Potassium channels are membrane-bound proteins responsible for regulating the flow of potassium ions through a cell membrane. The KCNQ (or $K_v7$) family is an important class of potassium channel that plays a key role in the process of neuronal excitability. There are five recognized subtypes of KCNQ channel: KCNQ1, KCNQ2, KCNQ3, KCNQ4, and KCNQ5. The KCNQ2-KCNQ5 subtypes represent the neuronal KCNQ subtypes. Miceli, *Curr. Op. Pharmacol.*, 2008, 8, 65. Functional KCNQ channels are formed by the assemblage of four individual subunits into a homotetramer or heterotetramer. The KCNQ2/3 channel is composed of a heterotetrameric assemblage of the KCNQ2 and KCNQ3 proteins.

The neuronal KCNQ channels are voltage-gated potassium channels that control cellular excitability by hyperpolarizing membrane potential, reducing action potential firing, and decreasing neurotransmitter release. Jentsch, *Nature Reviews Neurosci.*, 2000, 1, 21; Dalby-Brown, *Curr. Top. Med. Chem.*, 2006, 6, 999; Munro, *J. Med. Chem.*, 2007, 50, 2576. Neuronal KCNQ channels become activated on cellular depolarization (i.e., a change in voltage). See, Roza et al., *Pain,* 2008, 138, 537; Wickenden et al., *Mol. Pharmacol.,* 2000, 58, 591.

Activation of KCNQ channels by KCNQ openers causes an outflow of potassium ions from the cell, reducing the membrane potential (i.e., hyperpolarization), and thereby decreasing cellular excitability and action potential generation. Miceli, *Curr. Op. Pharmacol.,* 2008, 8, 65. In view of the role that KCNQ channels play in controlling cellular excitability and their distribution throughout the nervous system, KCNQ channel openers have been reported to have therapeutic utility in the treatment of a number of disorders characterized by abnormal neuronal excitability including: epilepsy, pain, migraine, anxiety, and overactive bladder. Dalby-Brown, *Curr. Top. Med. Chem.,* 2006, 6, 999; Streng, *J. Urol.,* 2004, 172, 2054. The dampening effect on neuronal excitability of KCNQ opening has also been implicated as a mechanism to inhibit the release of neurotransmitters (e.g., dopamine and serotonin) involved in schizophrenia, anxiety, and substance abuse. Hansen, *J. Physiol.* 2008, 1823.

A number of KCNQ openers, including flupirtine and retigabine, have been reported to be efficacious in treating various pain states in humans or rodents. These pain states include neuropathic pain (including diabetic polyneuropathy), inflammatory pain, persistent pain, cancer pain, and postoperative pain. Munro, *J. Med. Chem.,* 2007, 50, 2576; Dalby-Brown, *Curr. Top. Med. Chem.,* 2006, 6, 999. Thus, KCNQ openers have utility in treating a variety of painful conditions including, but not limited to, the foregoing types of pain.

The utility of KCNQ openers in the treatment of epilepsy is shown by the anticonvulsant and antiseizure activity of flupirtine, retigabine, and ICA-27243. Roeloffs, *J. Pharmacol. Exp. Ther.,* 2008, 326, 818; Miceli, *Curr. Op. Pharmacol.,* 2008, 8, 65; Blackburn-Munro, *CNS Drug Rev.,* 2005, 11, 1.

The utility of KCNQ openers in the treatment of migraine is indicated by the activity of KCNQ openers in an animal model of migraine. Wu, *J. Med. Chem.,* 2003, 46, 3197; Wu, *J. Med. Chem.,* 2003, 46, 3778.

The utility of KCNQ openers as anxiolytics is indicated by the activity of retigabine in animal models of anxiety. Dalby-Brown, *Curr. Top. Med. Chem.,* 2006, 6, 999.

The utility of KCNQ openers in the treatment of schizophrenia is indicated by the ability of retigabine to inhibit the activity of dopaminergic systems (Hansen, *J. Pharmacol. Exp. Ther.,* 2006, 318, 1006; Hansen, *J. Physiol.* 2008, 1823; Sotty, *J. Pharmacol. Exp. Ther.,* 2009, 328, 951) and by retigabine's efficacy in animal models of schizophrenia. Sotty, *J. Pharmacol. Exp. Ther.,* 2009, 328, 951.

Flupirtine and retigabine both possess liabilities in terms of adverse effects, including: asthenia, ataxia, insomnia, headache, drowsiness, dizziness, somnolence, dry mouth, nausea, vomiting, gastric and abdominal discomfort, sedation or loss of motor coordination. Miceli, *Curr. Op. Pharmacol.,* 2008, 8, 65; Munro, *J. Med. Chem.,* 2007, 50, 2576; Blackburn-Munro, *CNS Drug Rev.,* 2005, 11, 1. These adverse effects can be related to activation of one or more KCNQ subtypes not primarily responsible for the desirable therapeutic response. Thus, there is a need for KCNQ openers with efficacy in one or more of the foregoing disorders, states, or conditions, but without the side-effects of flupirtine or retigabine. KCNQ openers that selectively activate a particular subtype or subtypes can possess such efficacy with reduced side-effects.

SUMMARY OF THE INVENTION

Provided herein are compounds of formula (I)

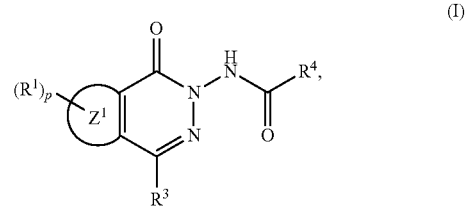

or pharmaceutically acceptable salts, solvates, prodrugs, or combinations thereof, wherein $Z^1$ is a ring fused with the pyridazine ring, selected from the group consisting of benzo, cycloalkyl, cycloalkenyl, heterocycle, and heteroaryl;

$R^1$ is an optional substituent wherein each occurrence of $R^1$ is independently $G^a$, alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —S(O)$_2$NR$^a$R$^b$, —C(O)R$^a$, —C(O)OR$^a$, —C(O)NR$^a$R$^b$, —N(R$^a$)COOR$^b$, —N(R$^a$)CONR$^a$R$^b$, —N(R$^a$)SO$_2$NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, —(CR$^{za}$R$^{zb}$)$_m$—NR$^a$R$^b$, —(CR$^{za}$R$^{zb}$)$_m$—N(R$^a$)COOR$^b$, —(CR$^{za}$R$^{zb}$)$_m$—N(R$^a$)CONR$^a$R$^b$, —(CR$^{za}$R$^{zb}$)$_m$—N(R$^a$)SO$_2$NR$^a$R$^b$, or —(CR$^{za}$R$^{zb}$)$_m$-G$^a$;

p is 0, 1, 2, 3, or 4;

R$^3$ is hydrogen, alkyl, alkenyl, alkynyl, halogen, haloalkyl, —(CR$^{3a}$R$^{3b}$)$_m$-G$^{3a}$, or G$^{3a}$;

G$^{3a}$, at each occurrence, is independently aryl, cycloalkyl, or cycloalkenyl; each of which is optionally substituted;

R$^4$ is alkenyl, alkynyl, haloalkyl, G$^{4a}$, —(CR$^{4a}$R$^{4b}$)$_n$-G$^{4a}$, or alkyl which is optionally substituted with one or two groups independently selected from the group consisting of S(R$^{1a}$), O(R$^{1a}$) and N(R$^{1a}$)$_2$;

each occurrence of R$^{1a}$ is independently hydrogen, G$^a$, —(CR$^{za}$R$^{zb}$)$_m$-G$^a$, alkyl, haloalkyl, hydroxyalkyl, or alkoxyalkyl;

G$^{4a}$, at each occurrence, is independently aryl, heteroaryl, heterocycle, cycloalkyl, or cycloalkenyl; each of which is optionally substituted;

G$^{3a}$ and G$^{4a}$, at each occurrence, are each independently unsubstituted or substituted with 1, 2, 3, or 4 substituents independently selected from the group consisting of G$^a$, alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —S(O)$_2$NR$^a$R$^b$, —C(O)R$^a$, —C(O)OR$^a$, —C(O)NR$^a$R$^b$, —N(R$^a$)COOR$^b$, —N(R$^a$)CONR$^a$R$^b$, —N(R$^a$)SO$_2$NR$^a$R$^b$, —(CR$^{za}$R$^{zb}$)$_m$-G$^a$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—S(O)$_2$NR$^a$R$^b$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, —(CR$^{za}$R$^{zb}$)$_m$—NR$^a$R$^b$, —(CR$^{za}$R$^{zb}$)$_m$—N(R$^a$)COOR$^b$, —(CR$^{za}$R$^{zb}$)$_m$—N(R$^a$)CONR$^a$R$^b$, and —(CR$^{za}$R$^{zb}$)$_m$—N(R$^a$)SO$_2$NR$^a$R$^b$;

G$^a$, at each occurrence, is independently aryl, heteroaryl, heterocycle, cycloalkyl, or cycloalkenyl; each of which is independently unsubstituted or substituted with 1, 2, or 3 substituents selected from the group consisting of alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —S(O)$_2$NR$^a$R$^b$, —C(O)R$^a$, —C(O)OR$^a$, —C(O)NR$^a$R$^b$, —N(R$^a$)COOR$^b$, —N(R$^a$)CONR$^a$R$^b$, —N(R$^a$)SO$_2$NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—S(O)$_2$NR$^a$R$^b$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, —(CR$^{za}$R$^{zb}$)$_m$—NR$^a$R$^b$, —(CR$^{za}$R$^{zb}$)$_m$—N(R$^a$)COOR$^b$, —(CR$^{za}$R$^{zb}$)$_m$—N(R$^a$)CONR$^a$R$^b$, and —(CR$^{za}$R$^{zb}$)$_m$—N(R$^a$)SO$_2$NR$^a$R$^b$;

R$^{za}$, R$^{zb}$, R$^{3a}$, R$^{3b}$, R$^{4a}$, and R$^{4b}$, at each occurrence, are each independently hydrogen, alkyl, halogen, or haloalkyl;

R$^a$ and R$^b$, at each occurrence, are each independently hydrogen, alkyl, or haloalkyl; and m and n, at each occurrence, are each independently 1, 2, 3, or 4;

with the proviso that when Z$^1$ is benzo, p is 0 or 4, R$^1$ is halogen, R$^3$ is G$^{3a}$, and G$^{3a}$ is aryl, substituted with 1 or 2 substituents selected from the group consisting of alkyl and unsubstituted aryl, then R$^4$ is other than unsubstituted aryl, unsubstituted alkyl, or haloalkyl.

Compounds described herein or pharmaceutically acceptable salts or solvates thereof are modulators of KCNQ potassium channels and are thus useful in the treatment of diseases, disorders, or conditions of a subject that are responsive to the opening of the modulation of the potassium channels.

Compounds of formula (I) are openers of KCNQ potassium channels and are useful in the treatment of conditions or disorders that are responsive to the opening of the KCNQ potassium channels, including pain.

Another aspect is related to pharmaceutical compositions comprising therapeutically effective amounts of one or more compound(s) described herein or pharmaceutically acceptable salts or solvates thereof, in combination with one or more pharmaceutically acceptable carrier(s). Such compositions can be administered in accordance with a method of the invention, typically as part of a therapeutic regimen for treatment or prevention of conditions and disorders related to the modulation of KCNQ channels. More particularly, the methods are useful for treating disorders or conditions related to pain such as neuropathic pain (including diabetic polyneuropathy), nociceptive pain, persistent pain, osteoarthritic pain, cancer pain, inflammatory pain, and postoperative pain, fibromyalgia, chronic widespread pain, musculoskeletal pain, myofascial pain, Temporomandibular joint pain (TMJ pain), as well as epilepsy, migraine, overactive bladder, schizophrenia, anxiety, and substance abuse.

Further provided herein are the use of the present compounds or pharmaceutically acceptable salts or solvates thereof, in the manufacture of a medicament for the treatment of the disease conditions described above, alone or in combination with one or more pharmaceutically acceptable carrier(s), particularly for the treatment or alleviation of disorders or conditions related to neuropathic pain (including diabetic polyneuropathy), nociceptive pain, persistent pain, osteoarthritic pain, cancer pain, inflammatory pain, postoperative pain, fibromyalgia, chronic widespread pain, musculoskeletal pain, myofascial pain, Temporomandibular joint pain (TMJ pain), epilepsy, migraine, overactive bladder, schizophrenia, anxiety, and substance abuse.

The compounds, compositions comprising the compounds or pharmaceutically acceptable salts or solvates thereof, and methods for treating or preventing conditions and disorders by administering the compounds or compositions thereof are further described herein.

These and other objects are described in the following paragraphs. These objects should not be deemed to narrow the scope of the invention.

DETAILED DESCRIPTION OF THE INVENTION

Provided herein are compounds of formula (I)

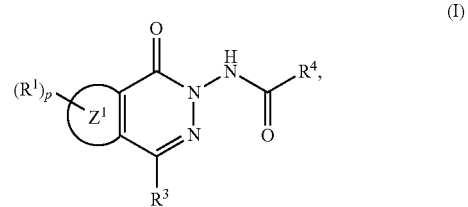

wherein Z$^1$, R$^1$, R$^3$, R$^4$, and p are as defined above in the Summary and below in the Detailed Description. Compositions comprising such compounds and methods for treating conditions and disorders using such compounds and compositions are also disclosed.

In various embodiments, there can be variables that occur more than one time in any substituent or in the compound or any other formulae herein. Definition of a variable on each occurrence is independent of its definition at another occurrence. Further, combinations of variables or substituents are permissible only if such combinations result in stable compounds. Stable compounds are compounds that can be isolated from a reaction mixture.

a. DEFINITIONS

As used in the specification and the appended claims, unless specified to the contrary, the following terms have the meaning indicated:

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylenyl radical.

The term "alkyl" as used herein, means a saturated, straight or branched hydrocarbon chain containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a saturated, straight or branched hydrocarbon chain of from 1 to 10 carbon atoms. Representative examples of alkylene include, but are not limited to, —$CH_2$—, —CH($CH_3$)—, —CH($C_2H_5$), —CH(CH($CH_3$)($C_2H_5$))—, —C(H)($CH_3$)$CH_2CH_2$—, —C($CH_3$)$_2$—, —$CH_2CH_2$—, —$CH_2CH_2CH_2$—, —$CH_2CH_2CH_2CH_2$—, and —$CH_2$CH($CH_3$)$CH_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl (including 1,2,3,4-tetrahydronaphthalen-1-yl). The phenyl and the bicyclic aryls are attached to the parent molecular moiety through any carbon atom contained within the phenyl or the bicyclic aryls respectively.

The term "cycloalkenyl" as used herein, means a monocyclic hydrocarbon ring system containing three-, four-, five-, six-, seven-, or eight carbon atoms and zero heteroatoms in the ring. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. The cycloalkenyl rings can have one or two pairs of non-adjacent carbon atoms within the ring system linked by one or two alkylene bridge(s) of 1, 2, 3, or 4 carbon atoms respectively. An example of such bridged cycloalkenyl group includes, but is not limited to, norbornene (bicyclo[2.2.1]hept-5-ene). The cycloalkenyl groups are appended to the parent molecular moiety through any substitutable carbon atom within the groups.

The term "cycloalkyl" as used herein, means a monocyclic, or a bicyclic cycloalkyl, or a spirocyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl ring. An example of a spirocyclic cycloalkyl is spiro[2.5]octane. The monocyclic cycloalkyl and the bicyclic cycloalkyl rings can have one or two pairs of non-adjacent carbon atoms within the ring system linked by one or two alkylene bridge(s) of 1, 2, 3, or 4 carbon atoms respectively. Non-limiting examples of such cycloalkyls include, hexahydro-2,5-methanopentalen-3a(1H)-yl, bicyclo[2.2.1]heptyl, bicyclo[3.1.1]heptyl (including bicyclo[3.1.1]hept-2-yl), bicyclo[2.2.2]octyl, bicyclo[3.3.1]nonyl, adamantane (tricyclo[3.3.1.1$^{3,7}$]decane), and noradamantane (octahydro-2,5-methanopentalene). The monocyclic, bicyclic, and spirocyclic cycloalkyl groups are appended to the parent molecular moiety through any substitutable carbon atom of the groups.

The term "halo" or "halogen" as used herein, means —Cl, —Br, —I or —F.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "haloalkoxy" as used herein, means an alkoxy group as defined herein, in which one, two, three, four, five, six, or seven hydrogen atoms are replaced by halogen. Non-limiting examples of haloalkoxy include trifluoromethoxy, 2,2,2-trifluoroethoxy, and 2-fluoroethoxy.

The term "haloalkoxyalkyl" as used herein, means an haloalkoxy group, as defined herein, appended to the parent molecular moiety through an alkylenyl radical.

The term "heteroaryl" as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, quinazolinyl, quinoxalinyl, and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings can optionally be oxidized and the nitrogen atoms can optionally be quarternized, and are contemplated within the scope of the invention.

The term "heterocycle" or "heterocyclic" as used herein, means a monocyclic, bicyclic, or a spirocyclic ring system containing at least one heteroatom. The monocyclic heterocycle is a 3-, 4-, 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Representative examples of monocyclic heterocycles include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Non-limiting examples of bicyclic heterocycle include 1,3-benzodioxolyl, 1,3-benzodithiolyl, 2,3-dihydro-1,4-benzodioxinyl, 2,3-dihydrobenzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro[3,4]octane. One or two pairs of non-adjacent carbon atoms within the monocyclic or bicyclic ring system can be linked by one or two alkylene bridge(s) of 1, 2, 3, or 4 carbon atoms respectively, one or two carbon atoms of the alkylene bridge(s) is optionally replaced by heteroatom(s) selected from O, N or S, wherein the nitrogen and sulfur atoms are optionally oxidized, and the nitrogen atom(s) are optionally quarternized. Non-limiting examples of the heterocycloalkyls containing such bridge include, oxadamantane (oxatricyclo[3.3.1.1$^{3,7}$]decane), azaadamantane, and azabicyclo[2.2.1]heptyl. The heterocycle groups are connected to the parent molecular moiety through any substitutable carbon atom or any substitutable nitrogen atom contained within the group. The nitrogen and sulfur heteroatoms in the heterocycle rings can optionally be oxidized (e.g. 1,1-dioxidothiomorpholinyl (thiomorpholine sulfone)) and the nitrogen atoms can optionally be quarternized.

In some instances, the number of carbon atoms in a substituent (e.g., alkyl, alkenyl, alkynyl, alkoxy, haloalkoxy, or cycloalkyl) is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms. Illustrating further, $C_3$-$C_6$ cycloalkyl means a saturated carbocyclic ring containing from 3 to 6 carbon ring atoms.

If a substituent is described as being optionally substituted with up to a particular number of non-hydrogen radicals, that substituent can be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 5 non-hydrogen radicals, then any heteroaryl with less than 5 substitutable positions would be optionally substituted by up to only as many non-hydrogen radicals as the heteroaryl has substitutable positions. To illustrate, thienyl (which has only four substitutable positions) would be optionally substituted with up to four non-hydrogen radicals.

The term "heteroatom" means N, O, or S.

The term "oxo" means =O.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "modulate" refers to the ability of a compound to increase or decrease the function, or activity, of KCNQ channels. "Modulation", as used herein in its various forms, is intended to encompass antagonism, agonism, partial antagonism and/or partial agonism of the activity associated with KCNQ channels. KCNQ channel activators are compounds that, e.g., bind to, stimulate, increase, open, activate, or facilitate KCNQ channels such as, but not limited to, KCNQ2, and/or KCNQ3, and/or KCNQ2/3 potassium channels. Activation of KCNQ channels encompasses either or both of: (1) increasing current through a KCNQ channel; or (2) shifting the half-activation potential of KCNQ channels to lower voltages (i.e. a hyperpolarizing shift of the $V_{1/2}$ for activation).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. COMPOUNDS

KCNQ channel modulators have formula (I) as described above.

Particular values of variable groups in compounds of formula (I) are as follows. Such values can be used where appropriate with any of the other values, definitions, claims or embodiments defined hereinbefore or hereinafter.

In compounds of formula (I), ring $Z^1$ has values as disclosed in the Summary.

In certain embodiments, ring $Z^1$ is benzo, heteroaryl, or cycloalkyl.

In certain embodiments, ring $Z^1$ is benzo, thus, included herein are compounds of formula (I-a)

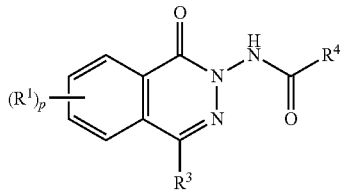

(I-a)

In certain embodiments, ring $Z^1$ is heteroaryl. Examples of such heteroaryl include, but are not limited to, thienyl and pyridinyl. Examples of compounds of formula (I) containing such rings include, but are not limited to, those represented by formula (I-b), (I-c), and (I-d):

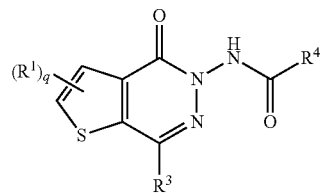

(I-b)

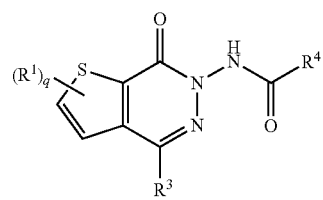

(I-c)

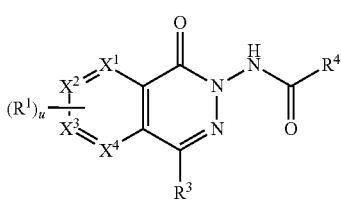

(I-d)

In certain embodiments, ring $Z^1$ is cycloalkyl, for example, a monocyclic cycloalkyl which can contain one or two alkylene bridges of 1, 2, 3, or 4 carbon atoms linking one or two pairs of non-adjacent carbon atoms within the ring system respectively. Examples of compounds of formula (I) containing such rings include but are not limited to those represented by formula (I-e).

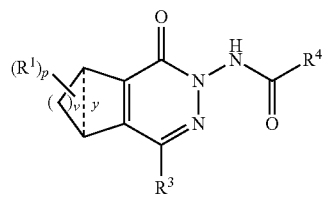

(I-e)

In compounds of formula (I-a)-(I-e) $R^1$, $R^3$, $R^4$, and p are as described in the Summary and in the embodiments herein; q is 0, 1, or 2; u is 0, 1, 2, or 3; v is 1, 2, or 3; dashed-line y is absent, a bond, —CH$_2$—, or —CH$_2$CH$_2$—; one or two of $X^1$, $X^2$, $X^3$, and $X^4$ are N and the others are CH.

Formula (I-e) can be described using the aforementioned values of y. For example, when y is absent, the compounds of the formula (I-e) can be represented by formula (I-e-i)

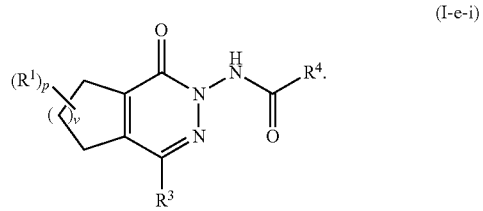

(I-e-i)

For example, when y is a bond, the compounds of the formula (I-e) can be represented by formula (I-e-ii)

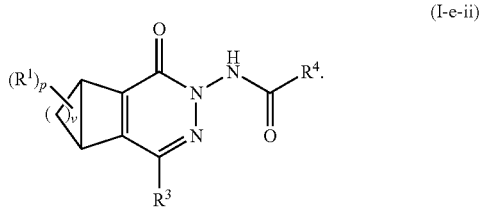

(I-e-ii)

For example, when y is a —CH$_2$—, the compounds of the formula (I-e) can be represented by formula (I-e-iii)

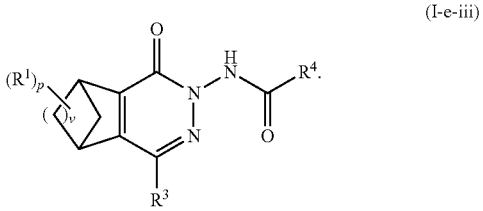

(I-e-iii)

For example, when y is a —CH$_2$CH$_2$—, the compounds of the formula (I-e) can be represented by formula (I-e-iv)

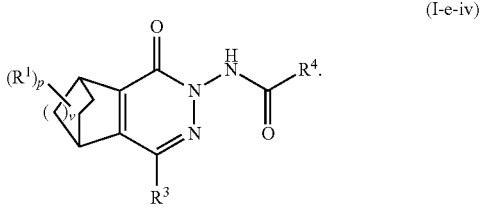

(I-e-iv)

In compounds of formula (I-e-i)-(I-e-iv), $R^1$, $R^3$, $R^4$, v, and p are as described in the embodiments herein above and below. In certain embodiments, v is 1. In yet other embodiments, v is 2.

$R^1$, when present in formula (I), (I-a)-(I-e), and (I-e-i)-(I-e-iv), is attached to any substitutable carbon atoms of ring $Z^1$ and has values as described in the Summary and embodiments herein.

For example, certain compounds of formula (I), (I-a)-(I-e), and (I-e-i)-(I-e-iv) include those wherein $R^1$ is absent.

Yet certain groups of compounds of formula (I), (I-a)-(I-e), and (I-e-i)-(I-e-iv) include those wherein $R^1$, at each occurrence, is independently halogen (e.g. Br, F), alkyl (e.g. $C_1$-$C_6$ alkyl such as, but not limited to, ethyl, methyl), or haloalkyl (e.g. trifluoromethyl).

$R^3$ for compounds of formula (I), (I-a)-(I-e), and (I-e-i)-(I-e-iv) have values as described in the Summary and embodiments herein.

For example, a group of compounds of formula (I), (I-a)-(I-e), and (I-e-i)-(I-e-iv) can have $R^3$ is alkyl (e.g. $C_1$-$C_6$ alkyl such as, but not limited to, methyl, ethyl, isopropyl, tert-butyl), halogen (e.g. Cl), haloalkyl (e.g. trifluoromethyl), $G^{3a}$, or —$(CR^{3a}R^{3b})_m$-$G^{3a}$. In certain embodiments, $R^3$ is alkyl (e.g. $C_1$-$C_6$ alkyl such as, but not limited to, methyl, ethyl, isopropyl, tert-butyl), haloalkyl (e.g. trifluoromethyl), $G^{3a}$ or —$(CR^{3a}R^{3b})_m$-$G^{3a}$. In certain embodiments, $R^3$ is alkyl (e.g. $C_1$-$C_6$ alkyl such as, but not limited to, methyl, ethyl, isopropyl, tert-butyl) or haloalkyl (e.g. trifluoromethyl). In certain embodiments, $R^3$ is $G^{3a}$ or —$(CR^{3a}R^{3b})_m$-$G^{3a}$. In certain embodiments, $R^3$ is $G^{3a}$. $R^{3a}$, $R^{3b}$, $G^{3a}$, and m are as described in the Summary and embodiments herein. For example, $G^{3a}$ is aryl (e.g. phenyl) or cycloalkyl such as, but not limited to $C_3$-$C_6$ alkyl (e.g. cyclopropyl, cyclobutyl, cyclopentyl, cyclohexyl). In certain embodiments, $G^{3a}$ is aryl such as, but not limited to, phenyl. In certain embodiments, $G^{3a}$ is cycloalkyl such as, but not limited to $C_3$-$C_6$ alkyl (e.g. cyclopropyl, cyclobutyl, cyclopentyl, cyclohexyl). Each of the aforementioned $G^{3a}$ is optionally substituted as described in the Summary and embodiments herein. Examples of the optional substituents of $G^{3a}$ include, but are not limited to, alkyl (e.g. $C_1$-$C_6$ alkyl such as, but not limited to, methyl, ethyl, isopropyl), halogen (e.g. Cl, F, Br), haloalkyl (e.g. trifluoromethyl), —$OR^a$, —$C(O)OR^a$, —$C(O)NR^aR^b$, or $G^a$. $R^a$, $R^b$, and $G^a$ are as described in the Summary and embodiments herein. $R^a$ and $R^b$ can be the same or different, and are for example, each independently hydrogen, alkyl such as, but not limited to, $C_1$-$C_6$ alkyl (e.g. methyl), or haloalkyl (e.g. $CF_3$). $G^a$, for example, is optionally substituted aryl such as, but not limited to, optionally substituted phenyl. $R^{3a}$ and $R^{3b}$ can be the same or different, and are each independently hydrogen or alkyl such as, but not limited to, $C_1$-$C_6$ alkyl (e.g. methyl). In certain embodiments, $R^{3a}$ and $R^{3b}$ are hydrogen. m, for example, is 1 or 2. In certain embodiments, m is 1.

$R^4$ for compounds of formula (I), (I-a)-(I-e), and (I-e-i)-(I-e-iv) have values as disclosed in the Summary and embodiments herein. For example, certain groups of compounds of formula (I), (I-a)-(I-e), and (I-e-i)-(I-e-iv) are those wherein $R^4$ is unsubstituted alkyl such as, but not limited to, $C_1$-$C_6$ alkyl (e.g. 2,2-dimethylpropyl, 3-methylbutyl), haloalkyl (e.g. 3,3,3-trifluoropropyl, 2,2,2-trifluoroethyl), —$(CR^{4a}R^{4b})_n$-$G^{4a}$, or alkyl (e.g. $C_1$-$C_2$ alkyl) substituted with a —$S(R^{1a})$ group. In certain embodiments, $R^4$ is haloalkyl (e.g. 3,3,3-trifluoropropyl, 2,2,2-trifluoroethyl) or unsubstituted alkyl such as, but not limited to, $C_1$-$C_6$ alkyl (e.g. 2,2-dimethylpropyl, 3-methylbutyl). In certain embodiments, $R^4$ is —$(CR^{4a}R^{4b})_n$-$G^{4a}$. In certain embodiments, $R^4$ is alkyl (e.g. $C_1$-$C_2$ alkyl) substituted with a —$S(R^{1a})$ group. $R^{1a}$, $R^{4a}$, $R^{4b}$, n, and $G^{4a}$ are as described in the Summary and in embodiments herein. For example, $R^{4a}$ and $R^{4b}$ are the same or different, and are each independently hydrogen, alkyl such as, but not limited to, $C_1$-$C_6$ alkyl (e.g. methyl, ethyl, isopropyl), or halogen (e.g. F). In conjunction with embodiments herein above and below, $R^{4a}$ and $R^{4b}$ are the same or different, and are each independently hydrogen or alkyl such as, but not limited to, $C_1$-$C_6$ alkyl (e.g. methyl, ethyl, isopropyl). n, for example, is 1 or 2. In certain embodiments, n is 1.

In yet other embodiments, n is 2. $G^{4a}$, for example, is heteroaryl such as, but not limited to, monocyclic heteroaryl (e.g. thienyl, pyridinyl), aryl (e.g. phenyl, naphthyl), heterocycle such as, but not limited to, monocyclic heterocycle (e.g. morpholinyl) and bicyclic heterocycle (e.g. 1,3-benzodioxolyl), cycloalkyl (e.g. adamantyl, bicyclo[3.1.1]heptyl, bicyclo[2.2.1]heptyl, cyclopropyl, cyclobutyl, cyclopentyl, cyclohexyl), or cycloalkenyl (e.g. bicyclo[2.2.1]hept-5-en-yl). In certain embodiments, $G^{4a}$ is heteroaryl such as, but not limited to, monocyclic heteroaryl (e.g. thienyl, pyridinyl). In certain embodiments, $G^{4a}$ is aryl (e.g. phenyl, naphthyl). In other embodiments, $G^{4a}$ is cycloalkyl (e.g. adamantyl, bicyclo[3.1.1]heptyl, bicyclo[2.2.1]heptyl, cyclopropyl, cyclobutyl, cyclopentyl, cyclohexyl). In certain embodiments, $G^{4a}$ is cycloalkenyl (e.g. bicyclo[2.2.1]hept-5-en-yl). Each aforementioned $G^{4a}$ (including the exemplary rings) is optionally substituted as described in the Summary and in embodiments herein. $R^{1a}$, for example, is alkyl such as, but not limited to $C_1$-$C_6$ alkyl (e.g. methyl, ethyl, isopropyl), or $G^a$ wherein $G^a$ is as described in the Summary and embodiments herein. For example, $G^a$, in certain embodiments, is optionally substituted cycloalkyl such as, but not limited to, optionally substituted adamantyl.

Examples of the optional substituents of $G^{4a}$ are described in the Summary. For example, the optional substituents of $G^{4a}$ include, but are not limited to, alkyl (e.g. $C_1$-$C_6$ alkyl such as, but not limited to, methyl, ethyl, isopropyl), halogen (e.g. F, Cl, Br), haloalkyl (e.g. trifluoromethyl), —$OR^a$, —$S(O)_2R^a$, $G^a$, —$NR^aR^b$. $R^a$, $R^b$, and $G^a$ are as described in the Summary and embodiments herein. For example, $R^a$ and $R^b$ can be the same or different, and are each, for example, independently hydrogen, alkyl (e.g. $C_1$-$C_6$ alkyl such as, but not limited to, methyl, ethyl, isopropyl), or haloalkyl (e.g. trifluoromethyl). $G^a$, for example, is optionally substituted aryl such as, but not limited to, optionally substituted phenyl.

It is appreciated that compounds of formula (I), (I-a)-(I-e), and (I-e-i)-(I-e-iv) with combinations of the above embodiments, including particular, more particular and preferred embodiments are contemplated.

Accordingly, one aspect relates to a group of compounds of formula (I) wherein ring $Z^1$ is benzo, heteroaryl, or cycloalkyl; and $R^4$ is unsubstituted alkyl such as, but not limited to, $C_1$-$C_6$ alkyl (e.g. 2,2-dimethylpropyl, 3-methylbutyl), haloalkyl (e.g. 3,3,3-trifluoropropyl, 2,2,2-trifluoroethyl), —$(CR^{4a}R^{4b})_n$-$G^{4a}$, or alkyl (e.g. $C_1$-$C_2$ alkyl) substituted with a —$S(R^{1a})$ group.

Another aspect relates to a group of compounds of formula (I) wherein ring $Z^1$ is benzo, heteroaryl, or cycloalkyl and $R^4$ is haloalkyl (e.g. 3,3,3-trifluoropropyl, 2,2,2-trifluoroethyl) or unsubstituted alkyl such as, but not limited to, $C_1$-$C_6$ alkyl (e.g. 2,2-dimethylpropyl, 3-methylbutyl).

Another aspect relates to a group of compounds of formula (I) wherein ring $Z^1$ is benzo, heteroaryl, or cycloalkyl and $R^4$ is alkyl (e.g. $C_1$-$C_2$ alkyl) substituted with a —$S(R^{1a})$ group. In certain embodiments, $R^4$ is $C_1$-$C_2$ alkyl substituted with a —$S(R^{1a})$ group.

Another aspect relates to a group of compounds of formula (I) wherein ring $Z^1$ is benzo, heteroaryl, or cycloalkyl, $R^4$ is —$(CR^{4a}R^{4b})_n$-$G^{4a}$; and $R^{4a}$, $R^{4b}$, n, and $G^{4a}$ are as described in the Summary and in embodiments herein.

Another aspect relates to a group of compounds of formula (I) wherein ring $Z^1$ is benzo, heteroaryl, or cycloalkyl, $R^4$ is —$(CR^{4a}R^{4b})_n$-$G^{4a}$; and $G^{4a}$ is heteroaryl such as, but not limited to, monocyclic heteroaryl (e.g. thienyl, pyridinyl), aryl (e.g. phenyl, naphthyl), heterocycle such as, but not limited to, monocyclic heterocycle (e.g. morpholinyl) and bicyclic heterocycle (e.g. 1,3-benzodioxolyl), cycloalkyl (e.g. adamantyl, bicyclo[3.1.1]heptyl, bicyclo[2.2.1]heptyl, cyclopropyl, cyclobutyl, cyclopentyl, cyclohexyl), or cycloalkenyl (e.g. bicyclo[2.2.1]hept-5-en-yl).

Another aspect relates to a group of compounds of formula (I) wherein ring $Z^1$ is benzo, heteroaryl, or cycloalkyl, $R^4$ is —$(CR^{4a}R^{4b})_n$-$G^{4a}$; and $G^{4a}$ is heteroaryl such as, but not limited to, monocyclic heteroaryl (e.g. thienyl, pyridinyl). In certain embodiments, $G^{4a}$ is thienyl.

Another aspect relates to a group of compounds of formula (I) wherein ring $Z^1$ is benzo, heteroaryl, or cycloalkyl, $R^4$ is —$(CR^{4a}R^{4b})_n$-$G^{4a}$; and $G^{4a}$ is aryl (e.g. phenyl, naphthyl). In certain embodiments, $G^{4a}$ is phenyl.

Another aspect relates to a group of compounds of formula (I) wherein ring $Z^1$ is benzo, heteroaryl, or cycloalkyl, $R^4$ is —$(CR^{4a}R^{4b})_n$-$G^{4a}$; and $G^{4a}$ is cycloalkyl (e.g. adamantyl, bicyclo[3.1.1]heptyl, bicyclo[2.2.1]heptyl, cyclopropyl, cyclobutyl, cyclopentyl, cyclohexyl).

Another aspect relates to a group of compounds of formula (I) wherein ring $Z^1$ is benzo, heteroaryl, or cycloalkyl, $R^4$ is —$(CR^{4a}R^{4b})_n$-$G^{4a}$; and $G^{4a}$ is cycloalkenyl (e.g. bicyclo[2.2.1]hept-5-en-yl).

Within each of the aforementioned groups of compounds, $R^{1a}$, $R^{4a}$, $R^{4b}$, and n are as described in the Summary and embodiments herein above, and each $G^{4a}$ (including the exemplary rings) is optionally substituted as described in the Summary and in embodiments herein above.

Within each group of compounds of formula (I), (I-a)-(I-e), and (I-e-i)-(I-e-iv) as described in the preceding paragraphs, $R^1$, $R^3$, p, q, u, y, and v are as described generally in the Summary and in embodiments described above and herein.

Thus, of each group of compounds of formula (I), (I-a)-(I-e), and (I-e-i)-(I-e-iv) as described in the preceding paragraphs, examples of a subgroup include those wherein $R^3$ is alkyl (e.g. $C_1$-$C_6$ alkyl such as, but not limited to, methyl, ethyl, isopropyl, tert-butyl), halogen (e.g. Cl), haloalkyl (e.g. trifluoromethyl), $G^{3a}$ or —$(CR^{3a}R^{3b})_m$-$G^{3a}$, wherein $R^{3a}$, $R^{3b}$, m, and $G^{3a}$ are as described in the Summary and embodiments herein.

Examples of another subgroup include those wherein $R^3$ is alkyl (e.g. $C_1$-$C_6$ alkyl such as, but not limited to, methyl, ethyl, isopropyl, tert-butyl), haloalkyl (e.g. trifluoromethyl), $G^{3a}$ or —$(CR^{3a}R^{3b})_m$-$G^{3a}$, wherein $R^{3a}$, $R^{3b}$, m, and $G^{3a}$ are as described in the Summary and embodiments herein.

Yet other examples of a subgroup include those wherein $R^3$ is alkyl (e.g. $C_1$-$C_6$ alkyl such as, but not limited to, methyl, ethyl, isopropyl, tert-butyl) or haloalkyl.

Yet other examples of a subgroup include those wherein $R^3$ is $G^{3a}$ or —$(CR^{3a}R^{3b})_m$-$G^{3a}$, wherein $R^{3a}$, $R^{3b}$, m, and $G^{3a}$ are as described in the Summary and embodiments herein.

Yet other examples of a subgroup include those $R^3$ is $G^{3a}$, and $G^{3a}$ is as described in the Summary and embodiments herein.

For each of the groups and subgroups of examples listed herein above, certain embodiments are directed to those wherein $G^{3a}$ is aryl (e.g. phenyl) or cycloalkyl such as, but not limited to, $C_3$-$C_6$ cycloalkyl (cyclopropyl, cyclobutyl, cyclopentyl, cyclohexyl). Certain embodiments are directed to those wherein $G^{3a}$ is aryl (e.g. phenyl). Certain embodiments are directed to those wherein $G^{3a}$ is cycloalkyl such as, but not limited to, $C_3$-$C_6$ cycloalkyl (cyclopropyl, cyclobutyl, cyclopentyl, cyclohexyl). Each of the aforementioned $G^{3a}$ is optionally substituted as described in the Summary and embodiments herein. $R^{3a}$, $R^{3b}$, and m are as disclosed in the Summary and embodiments herein above.

Within each group and subgroup of compounds of formula (I), (I-a)-(I-e), and (I-e-i)-(I-e-iv) as described herein above, $R^1$, p, q, u, and v have values as described generally in the Summary and specifically in embodiments herein above.

Exemplary compounds contemplated include, but are not limited to:

2-(4-chlorophenyl)-N-(4-isopropyl-1-oxophthalazin-2(1H)-yl)acetamide;
2-(1-adamantyl)-N-[4-(4-bromophenyl)-1-oxophthalazin-2(1H)-yl]acetamide;
N-[4-(4-bromophenyl)-1-oxophthalazin-2(1H)-yl]-2-(4-chlorophenyl)acetamide;
2-(4-chlorophenyl)-N-(1-oxo-4-phenylphthalazin-2(1H)-yl)acetamide;
2-(3,5-difluorophenyl)-N-(4-isopropyl-1-oxophthalazin-2(1H)-yl)acetamide;
2-(1-adamantyl)-N-(4-isopropyl-1-oxophthalazin-2(1H)-yl)acetamide;
2-(1-adamantyl)-N-(8-oxo-5-phenylpyrido[2,3-d]pyridazin-7(8H)-yl)acetamide;
2-(1-adamantyl)-N-(4-isopropyl-1-oxo-5,6,7,8-tetrahydro-5,8-ethanophthalazin-2(1H)-yl)acetamide;
2-(1-adamantyl)-N-(4-oxo-7-phenylthieno[2,3-d]pyridazin-5(4H)-yl)acetamide;
2-(3,5-difluorophenyl)-N-(4-oxo-7-phenylthieno[2,3-d]pyridazin-5(4H)-yl)acetamide;
2-(3,5-difluorophenyl)-N-[1-oxo-4-(trifluoromethyl)phthalazin-2(1H)-yl]acetamide;
2-(1-adamantyl)-N-[1-oxo-4-(trifluoromethyl)phthalazin-2(1H)-yl]acetamide;
2-(4-chlorophenyl)-N-[1-oxo-4-(trifluoromethyl)phthalazin-2(1H)-yl]acetamide;
N-(5,8-difluoro-1-oxo-4-phenylphthalazin-2(1H)-yl)-2-(4-fluorophenyl)acetamide;
2-(1-adamantyl)-N-(5,8-difluoro-1-oxo-4-phenylphthalazin-2(1H)-yl)acetamide;
2-(4-chlorophenyl)-N-(5,8-difluoro-1-oxo-4-phenylphthalazin-2(1H)-yl)acetamide;
2-(1-adamantyl)-N-(1-oxo-4-phenylphthalazin-2(1H)-yl)acetamide;
2-(3,5-difluorophenyl)-N-(1-oxo-4-phenylphthalazin-2(1H)-yl)acetamide;
N-(4-chloro-1-oxophthalazin-2(1H)-yl)-2-(3,5-difluorophenyl)acetamide;
2-(1-adamantyl)-N-(4-chloro-1-oxophthalazin-2(1H)-yl)acetamide;
N-(4-chloro-1-oxophthalazin-2(1H)-yl)-2-(4-chlorophenyl)acetamide;
2-(4-chlorophenyl)-N-(4-cyclopropyl-1-oxophthalazin-2(1H)-yl)acetamide;
N-(4-cyclopropyl-1-oxophthalazin-2(1H)-yl)-2-(3,5-difluorophenyl)acetamide;
2-(1-adamantyl)-N-(4-cyclopropyl-1-oxophthalazin-2(1H)-yl)acetamide;
2-(2,3-difluorophenyl)-N-(1-oxo-4-phenylphthalazin-2(1H)-yl)acetamide;
2-(4-fluorophenyl)-N-(1-oxo-4-phenylphthalazin-2(1H)-yl)acetamide;
2-(2,5-difluorophenyl)-N-(1-oxo-4-phenylphthalazin-2(1H)-yl)acetamide;
2-(4-chlorophenyl)-N-(4-methyl-1-oxophthalazin-2(1H)-yl)acetamide;
2-(1-adamantyl)-N-(7-oxo-4-phenylthieno[2,3-d]pyridazin-6(7H)-yl)acetamide;
2-[(1S,2S,5S)-6,6-dimethylbicyclo[3.1.1]hept-2-yl]-N-(7-oxo-4-phenylthieno[2,3-d]pyridazin-6(7H)-yl)acetamide;
2-(4-chlorophenyl)-N-(7-oxo-4-phenylthieno[2,3-d]pyridazin-6(7H)-yl)acetamide;

2-(4-fluorophenyl)-N-(7-oxo-4-phenylthieno[2,3-d]pyridazin-6(7H)-yl)acetamide;
2-(3,5-difluorophenyl)-N-(7-oxo-4-phenylthieno[2,3-d]pyridazin-6(7H)-yl)acetamide;
2-[3,5-dimethyl-1-adamantyl]-N-(4-isopropyl-1-oxophthalazin-2(1H)-yl)acetamide;
2-(3,5-difluorophenyl)-N-(6-fluoro-1-oxo-4-phenylphthalazin-2(1H)-yl)acetamide;
2-(4-chlorophenyl)-N-(6-fluoro-1-oxo-4-phenylphthalazin-2(1H)-yl)acetamide;
2-(1-adamantyl)-N-(6-fluoro-1-oxo-4-phenylphthalazin-2(1H)-yl)acetamide;
2-(3,5-difluorophenyl)-N-(4-methyl-1-oxophthalazin-2(1H)-yl)acetamide;
2-[1-(4-chlorophenyl)cyclopropyl]-N-[1-oxo-4-(trifluoromethyl)phthalazin-2(1H)-yl]acetamide;
2-[1-(4-chlorophenyl)cyclobutyl]-N-[1-oxo-4-(trifluoromethyl)phthalazin-2(1H)-yl]acetamide;
2-(2-naphthyl)-N-[1-oxo-4-(trifluoromethyl)phthalazin-2(1H)-yl]acetamide;
3-(4-chlorophenyl)-3-methyl-N-[1-oxo-4-(trifluoromethyl)phthalazin-2(1H)-yl]butanamide;
2-cyclopentyl-N-[1-oxo-4-(trifluoromethyl)phthalazin-2(1H)-yl]acetamide;
2,2-difluoro-N-[1-oxo-4-(trifluoromethyl)phthalazin-2(1H)-yl]-2-phenylacetamide;
2-cyclobutyl-N-[1-oxo-4-(trifluoromethyl)phthalazin-2(1H)-yl]acetamide;
N-[1-oxo-4-(trifluoromethyl)phthalazin-2(1H)-yl]-2-[4-(trifluoromethyl)phenyl]acetamide;
2-[4-(dimethylamino)phenyl]-N-[1-oxo-4-(trifluoromethyl)phthalazin-2(1H)-yl]acetamide;
3,3-dimethyl-N-[1-oxo-4-(trifluoromethyl)phthalazin-2(1H)-yl]butanamide;
2-[4-(methylsulfonyl)phenyl]-N-[1-oxo-4-(trifluoromethyl)phthalazin-2(1H)-yl]acetamide;
N-[1-oxo-4-(trifluoromethyl)phthalazin-2(1H)-yl]-3-phenylpropanamide;
N-[1-oxo-4-(trifluoromethyl)phthalazin-2(1H)-yl]-2-(1-phenylcyclopropyl)acetamide;
3-methyl-N-[1-oxo-4-(trifluoromethyl)phthalazin-2(1H)-yl]-3-phenylbutanamide;
N-[1-oxo-4-(trifluoromethyl)phthalazin-2(1H)-yl]-2-(3-thienyl)acetamide;
N-[1-oxo-4-(trifluoromethyl)phthalazin-2(1H)-yl]-2-(2-thienyl)acetamide;
2-(5-chloro-2-thienyl)-N-[1-oxo-4-(trifluoromethyl)phthalazin-2(1H)-yl]acetamide;
2-(5-methyl-2-thienyl)-N-[1-oxo-4-(trifluoromethyl)phthalazin-2(1H)-yl]acetamide;
N-[1-oxo-4-(trifluoromethyl)phthalazin-2(1H)-yl]-2-phenylacetamide;
(±)-2-(exo-bicyclo[2.2.1]heptan-2-yl)-N-[1-oxo-4-(trifluoromethyl)phthalazin-2(1H)-yl]acetamide;
2-(4-chloro-3-fluorophenyl)-N-[1-oxo-4-(trifluoromethyl)phthalazin-2(1H)-yl]acetamide;
2-(3-fluoroadamantan-1-yl)-N-(4-isopropyl-1-oxophthalazin-2(1H)-yl)acetamide;
2-(3-hydroxyadamantan-1-yl)-N-(4-isopropyl-1-oxophthalazin-2(1H)-yl)acetamide;
N-(4-tert-butyl-1-oxophthalazin-2(1H)-yl)-2-cyclopentylacetamide;
(±)-2-(exo-bicyclo[2.2.1]heptan-2-yl)-N-(4-tert-butyl-1-oxophthalazin-2(1H)-yl)acetamide;
N-(4-tert-butyl-1-oxophthalazin-2(1H)-yl)-3-methyl-3-phenylbutanamide;
N-(4-tert-butyl-1-oxophthalazin-2(1H)-yl)-2-(4-chlorophenyl)acetamide;
2-[(1S,2S,4R)-bicyclo[2.2.1]hept-2-yl]-N-(4-cyclobutyl-1-oxophthalazin-2(1H)-yl)acetamide;
2-[(1S,2S,4S)-bicyclo[2.2.1]hept-5-en-2-yl]-N-(4-cyclobutyl-1-oxophthalazin-2(1H)-yl)acetamide;
(±)-2-(exo-bicyclo[2.2.1]heptan-2-yl)-N-(4-cyclobutyl-1-oxophthalazin-2(1H)-yl)acetamide;
N-(4-cyclobutyl-1-oxophthalazin-2(1H)-yl)-2-(3,5-difluorophenyl)acetamide;
2-(4-chlorophenyl)-N-(4-cyclobutyl-1-oxophthalazin-2(1H)-yl)acetamide;
(±)-2-(exo-bicyclo[2.2.1]heptan-2-yl)-N-(4-cyclopentyl-1-oxophthalazin-2(1H)-yl)acetamide;
2-(4-chlorophenyl)-N-(4-cyclopentyl-1-oxophthalazin-2(1H)-yl)acetamide;
N-(4-cyclopentyl-1-oxophthalazin-2(1H)-yl)-2-(3,5-difluorophenyl)acetamide;
(±)-2-(exo-bicyclo[2.2.1]heptan-2-yl)-N-(4-cyclohexyl-1-oxophthalazin-2(1H)-yl)acetamide;
2-(adamantan-1-yl)-N-(4-cyclohexyl-1-oxophthalazin-2(1H)-yl)acetamide;
2-(4-chlorophenyl)-N-(4-cyclohexyl-1-oxophthalazin-2(1H)-yl)acetamide;
N-(4-cyclohexyl-1-oxophthalazin-2(1H)-yl)-2-(3,5-difluorophenyl)acetamide;
(±)-4-(3-{[(exo-bicyclo[2.2.1]heptan-2-yl)acetyl]amino}-4-oxo-3,4-dihydrophthalazin-1-yl)benzoic acid;
(±)-methyl 4-(3-{[exo-bicyclo[2.2.1]hept-2-ylacetyl]amino}-4-oxo-3,4-dihydrophthalazin-1-yl)benzoate;
methyl 4-(3-{[(4-chlorophenyl)acetyl]amino}-4-oxo-3,4-dihydrophthalazin-1-yl)benzoate;
(±)-4-(3-{[exo-bicyclo[2.2.1]hept-2-ylacetyl]amino}-4-oxo-3,4-dihydrophthalazin-1-yl)-N,N-dimethylbenzamide;
3-methyl-N-(1-oxo-4-phenylphthalazin-2(1H)-yl)-3-phenylbutanamide;
2-(2,4-dichlorophenyl)-N-(1-oxo-4-phenylphthalazin-2(1H)-yl)acetamide;
(±)-2-(exo-bicyclo[2.2.1]heptan-2-yl)-N-[4-(4-bromophenyl)-1-oxophthalazin-2(1H)-yl]acetamide;
N-[4-(4-bromophenyl)-1-oxophthalazin-2(1H)-yl]-3-methyl-3-phenylbutanamide;
N-[4-(4-chlorophenyl)-1-oxophthalazin-2(1H)-yl]-2-(1-methylcyclopentyl)acetamide;
N-[4-(4-chlorophenyl)-1-oxophthalazin-2(1H)-yl]-2-[1-(trifluoromethyl)cyclopentyl]acetamide;
N-[4-(4-chlorophenyl)-1-oxophthalazin-2(1H)-yl]-2-[(1S,2S,5R)-3,3-difluoro-6,6-dimethylbicyclo[3.1.1]hept-2-yl]acetamide;
N-[4-(4-chlorophenyl)-1-oxophthalazin-2(1H)-yl]-3-methyl-3-phenylbutanamide;
N-[4-(4-chlorophenyl)-1-oxophthalazin-2(1H)-yl]-2-fluoro-2-phenylacetamide;
N-[4-(4-chlorophenyl)-1-oxophthalazin-2(1H)-yl]-2-phenylacetamide;
N-[4-(4-chlorophenyl)-1-oxophthalazin-2(1H)-yl]-2-(morpholin-4-yl)acetamide;
N-[4-(4-chlorophenyl)-1-oxophthalazin-2(1H)-yl]-2-(pyridin-3-yl)acetamide;
N-[4-(4-chlorophenyl)-1-oxophthalazin-2(1H)-yl]-2-(pyridin-2-yl)acetamide;
N-[4-(4-chlorophenyl)-1-oxophthalazin-2(1H)-yl]-2-(3,4-dichlorophenyl)acetamide;
N-[4-(4-chlorophenyl)-1-oxophthalazin-2(1H)-yl]-2-(3,5-dimethoxyphenyl)acetamide;

N-[4-(4-chlorophenyl)-1-oxophthalazin-2(1H)-yl]-2-(3,5-dimethylphenyl)acetamide;
N-[4-(4-chlorophenyl)-1-oxophthalazin-2(1H)-yl]-2-[3-(trifluoromethoxy)phenyl]acetamide;
N-[4-(4-chlorophenyl)-1-oxophthalazin-2(1H)-yl]-2-[4-(trifluoromethyl)phenyl]acetamide;
N-[4-(4-chlorophenyl)-1-oxophthalazin-2(1H)-yl]-2-[3-(trifluoromethyl)phenyl]acetamide;
N-[4-(4-chlorophenyl)-1-oxophthalazin-2(1H)-yl]-2-[4-(dimethylamino)phenyl]acetamide;
2-(4-bromophenyl)-N-[4-(4-chlorophenyl)-1-oxophthalazin-2(1H)-yl]acetamide;
2-(3-chlorophenyl)-N-[4-(4-chlorophenyl)-1-oxophthalazin-2(1H)-yl]acetamide;
N-[4-(4-chlorophenyl)-1-oxophthalazin-2(1H)-yl]-2-(4-methoxyphenyl)acetamide;
N-[4-(4-chlorophenyl)-1-oxophthalazin-2(1H)-yl]-2-(3-methoxyphenyl)acetamide;
N-[4-(4-chlorophenyl)-1-oxophthalazin-2(1H)-yl]-2-(4-hydroxyphenyl)acetamide;
N-[4-(4-chlorophenyl)-1-oxophthalazin-2(1H)-yl]-2-(4-methylphenyl)acetamide;
N-[4-(4-chlorophenyl)-1-oxophthalazin-2(1H)-yl]-2-(3-methylphenyl)acetamide;
N-[4-(4-chlorophenyl)-1-oxophthalazin-2(1H)-yl]-2-cyclopentylacetamide;
N-[4-(4-chlorophenyl)-1-oxophthalazin-2(1H)-yl]-4-methylpentanamide;
N-[4-(4-chlorophenyl)-1-oxophthalazin-2(1H)-yl]-2-[4-(methylsulfonyl)phenyl]acetamide;
N-[4-(4-chlorophenyl)-1-oxophthalazin-2(1H)-yl]-2-(5-chloro-2-thienyl)acetamide;
(±)-2-(exo-bicyclo[2.2.1]hept-2-yl)-N-[4-(4-chlorophenyl)-1-oxophthalazin-2(1H)-yl]acetamide;
2-(4-chloro-3-fluorophenyl)-N-[4-(4-chlorophenyl)-1-oxophthalazin-2(1H)-yl]acetamide;
N-[4-(4-chlorophenyl)-1-oxophthalazin-2(1H)-yl]-2-[(1S,2S,5S)-6,6-dimethylbicyclo[3.1.1]hept-2-yl]acetamide;
2-(adamantan-1-yl)-N-[4-(4-chlorophenyl)-1-oxophthalazin-2(1H)-yl]acetamide;
2-(4-chlorophenyl)-N-[4-(4-chlorophenyl)-1-oxophthalazin-2(1H)-yl]acetamide;
N-[4-(4-chlorophenyl)-1-oxophthalazin-2(1H)-yl]-2-(3,5-difluorophenyl)acetamide;
N-[4-(4-chlorophenyl)-1-oxophthalazin-2(1H)-yl]-2-(1-phenylcyclopentyl)acetamide;
N-[4-(4-chlorophenyl)-1-oxophthalazin-2(1H)-yl]-2-phenylcyclopropanecarboxamide;
N-[4-(4-chlorophenyl)-1-oxophthalazin-2(1H)-yl]-2-(2-naphthyl)acetamide;
N-[4-(4-chlorophenyl)-1-oxophthalazin-2(1H)-yl]-2-(1-naphthyl)acetamide;
N-[4-(4-chlorophenyl)-1-oxophthalazin-2(1H)-yl]-4,4,4-trifluorobutanamide;
N-[4-(4-chlorophenyl)-1-oxophthalazin-2(1H)-yl]-3,3,3-trifluoropropanamide;
(±)-2-(exo-bicyclo[2.2.1]hept-2-yl)-N-[4-(3-chlorophenyl)-1-oxophthalazin-2(1H)-yl]acetamide;
2-(adamantan-1-yl)-N-[4-(3-chlorophenyl)-1-oxophthalazin-2(1H)-yl]acetamide;
2-(4-chlorophenyl)-N-[4-(3-chlorophenyl)-1-oxophthalazin-2(1H)-yl]acetamide;
N-[4-(3-chlorophenyl)-1-oxophthalazin-2(1H)-yl]-2-(3,5-difluorophenyl)acetamide;
2-[(1S,2S,4R)-bicyclo[2.2.1]hept-2-yl]-N-[4-(4-fluorophenyl)-1-oxophthalazin-2(1H)-yl]acetamide;
2-[(1S,2S,4S)-bicyclo[2.2.1]hept-5-en-2-yl]-N-[4-(4-fluorophenyl)-1-oxophthalazin-2(1H)-yl]acetamide;
(±)-2-(exo-bicyclo[2.2.1]hept-2-yl)-N-[4-(4-fluorophenyl)-1-oxophthalazin-2(1H)-yl]acetamide;
2-(4-chlorophenyl)-N-[4-(4-fluorophenyl)-1-oxophthalazin-2(1H)-yl]acetamide;
2-(3,5-difluorophenyl)-N-[4-(4-fluorophenyl)-1-oxophthalazin-2(1H)-yl]acetamide;
(±)-2-(exo-bicyclo[2.2.1]hept-2-yl)-N-[4-(2,4-difluorophenyl)-1-oxophthalazin-2(1H)-yl]acetamide;
2-(4-chlorophenyl)-N-[4-(4-methylphenyl)-1-oxophthalazin-2(1H)-yl]acetamide;
2-(3,5-difluorophenyl)-N-[4-(4-methylphenyl)-1-oxophthalazin-2(1H)-yl]acetamide;
2-[(1S,2S,5S)-6,6-dimethylbicyclo[3.1.1]hept-2-yl]-N-[4-(4-methylphenyl)-1-oxophthalazin-2(1H)-yl]acetamide;
2-(adamantan-1-yl)-N-[4-(4-methylphenyl)-1-oxophthalazin-2(1H)-yl]acetamide;
N-(4-benzyl-1-oxophthalazin-2(1H)-yl)-2-[1-(trifluoromethyl)cyclopentyl]acetamide;
N-(4-benzyl-1-oxophthalazin-2(1H)-yl)-3-methyl-3-phenylbutanamide;
(±)-N-(4-benzyl-1-oxophthalazin-2(1H)-yl)-2-(exo-bicyclo[2.2.1]hept-2-yl)acetamide;
N-(4-benzyl-1-oxophthalazin-2(1H)-yl)-2-(4-chlorophenyl)acetamide;
N-(4-benzyl-1-oxophthalazin-2(1H)-yl)-2-(3,5-difluorophenyl)acetamide;
(±)-2-(exo-bicyclo[2.2.1]hept-2-yl)-N-[4-(4-chlorobenzyl)-1-oxophthalazin-2(1H)-yl]acetamide;
N-[4-(4-chlorobenzyl)-1-oxophthalazin-2(1H)-yl]-2-(4-chlorophenyl)acetamide;
N-[4-(4-chlorobenzyl)-1-oxophthalazin-2(1H)-yl]-2-(3,5-difluorophenyl)acetamide;
2-[(1S,2S,4R)-bicyclo[2.2.1]hept-2-yl]-N-{1-oxo-4-[4-(trifluoromethyl)phenyl]phthalazin-2(1H)-yl}acetamide;
3-methyl-N-{1-oxo-4-[4-(trifluoromethyl)phenyl]phthalazin-2(1H)-yl}-3-phenylbutanamide;
2-(adamantan-1-yl)-N-{1-oxo-4-[4-(trifluoromethyl)phenyl]phthalazin-2(1H)-yl}acetamide;
(±)-2-(exo-bicyclo[2.2.1]hept-2-yl)-N-{1-oxo-4-[4-(trifluoromethyl)phenyl]phthalazin-2(1H)-yl}acetamide;
(±)-2-(exo-bicyclo[2.2.1]hept-2-yl)-N-[4-(4-methoxyphenyl)-1-oxophthalazin-2(1H)-yl]acetamide;
N-[4-(4-methoxyphenyl)-1-oxophthalazin-2(1H)-yl]-2-(4-methylcyclohexyl)acetamide;
2-(3,5-difluorophenyl)-N-[4-(4-methoxyphenyl)-1-oxophthalazin-2(1H)-yl]acetamide;
2-(adamantan-1-yl)-N-[4-(4-methoxyphenyl)-1-oxophthalazin-2(1H)-yl]acetamide;
(±)-2-(exo-bicyclo[2.2.1]hept-2-yl)-N-[4-(2,5-dimethylphenyl)-1-oxophthalazin-2(1H)-yl]acetamide;
2-(adamantan-1-yl)-N-[4-(2,5-dimethylphenyl)-1-oxophthalazin-2(1H)-yl]acetamide;
2-(4-chlorophenyl)-N-[4-(2,5-dimethylphenyl)-1-oxophthalazin-2(1H)-yl]acetamide;
2-(3,5-difluorophenyl)-N-[4-(2,5-dimethylphenyl)-1-oxophthalazin-2(1H)-yl]acetamide;
2-[(1S,2S,4S)-bicyclo[2.2.1]hept-5-en-2-yl]-N-[4-(2,4-dimethylphenyl)-1-oxophthalazin-2(1H)-yl]acetamide;
(±)-2-(exo-bicyclo[2.2.1]hept-2-yl)-N-[4-(2,4-dimethylphenyl)-1-oxophthalazin-2(1H)-yl]acetamide;
2-(4-chlorophenyl)-N-[4-(2,4-dimethylphenyl)-1-oxophthalazin-2(1H)-yl]acetamide;
2-(3,5-difluorophenyl)-N-[4-(2,4-dimethylphenyl)-1-oxophthalazin-2(1H)-yl]acetamide;

(±)-2-(exo-bicyclo[2.2.1]hept-2-yl)-N-[4-(3,4-dimethylphenyl)-1-oxophthalazin-2(1H)-yl]acetamide;
2-(adamantan-1-yl)-N-[4-(3,4-dimethylphenyl)-1-oxophthalazin-2(1H)-yl]acetamide;
2-(4-chlorophenyl)-N-[4-(3,4-dimethylphenyl)-1-oxophthalazin-2(1H)-yl]acetamide;
2-(3,5-difluorophenyl)-N-[4-(3,4-dimethylphenyl)-1-oxophthalazin-2(1H)-yl]acetamide;
(±)-2-(exo-bicyclo[2.2.1]hept-2-yl)-N-[1-oxo-4-(2-phenylethyl)phthalazin-2(1H)-yl]acetamide;
(±)-2-(exo-bicyclo[2.2.1]hept-2-yl)-N-[4-(4-isopropylphenyl)-1-oxophthalazin-2(1H)-yl]acetamide;
2-(adamantan-1-yl)-N-[4-(4-isopropylphenyl)-1-oxophthalazin-2(1H)-yl]acetamide;
2-(4-chlorophenyl)-N-[4-(4-isopropylphenyl)-1-oxophthalazin-2(1H)-yl]acetamide;
2-(3,5-difluorophenyl)-N-[4-(4-isopropylphenyl)-1-oxophthalazin-2(1H)-yl]acetamide;
(±)-2-(exo-bicyclo[2.2.1]hept-2-yl)-N-[1-oxo-4-(1-phenylcyclopropyl)phthalazin-2(1H)-yl]acetamide;
2-(adamantan-1-yl)-N-[4-isopropyl-1-oxo-7-(trifluoromethyl)phthalazin-2(1H)-yl]acetamide;
2-(adamantan-1-yl)-N-[6-bromo-4-(4-methoxyphenyl)-1-oxophthalazin-2(1H)-yl]acetamide;
2-(adamantan-1-yl)-N-[6-bromo-4-(4-methoxyphenyl)-1-oxophthalazin-2(1H)-yl]acetamide;
N-[6-bromo-4-(4-methoxyphenyl)-1-oxophthalazin-2(1H)-yl]-2-(3,5-difluorophenyl)acetamide;
N-[7-bromo-4-(4-methoxyphenyl)-1-oxophthalazin-2(1H)-yl]-2-(3,5-difluorophenyl)acetamide;
2-(3-bromoadamantan-1-yl)-N-(7-oxo-4-phenylthieno[2,3-d]pyridazin-6(7H)-yl)acetamide;
2-(3-fluoroadamantan-1-yl)-N-(7-oxo-4-phenylthieno[2,3-d]pyridazin-6(7H)-yl)acetamide;
2-(3-hydroxyadamantan-1-yl)-N-(7-oxo-4-phenylthieno[2,3-d]pyridazin-6(7H)-yl)acetamide;
N-[4-(4-chlorophenyl)-5,8-difluoro-1-oxophthalazin-2(1H)-yl]-2-(3,5-difluorophenyl)acetamide;
2-(4-chlorophenyl)-N-[4-(4-chlorophenyl)-5,8-difluoro-1-oxophthalazin-2(1H)-yl]acetamide;
2-(adamantan-1-yl)-N-[4-(4-chlorophenyl)-5,8-difluoro-1-oxophthalazin-2(1H)-yl]acetamide;
(±)-2-(exo-bicyclo[2.2.1]hept-2-yl)-N-[4-(4-chlorophenyl)-5,8-difluoro-1-oxophthalazin-2(1H)-yl]acetamide;
2-(adamantan-1-yl)-N-(1-oxo-4-phenyl-5,6,7,8-tetrahydrophthalazin-2(1H)-yl)acetamide;
2-(3,5-difluorophenyl)-N-(1-oxo-4-phenyl-5,6,7,8-tetrahydrophthalazin-2(1H)-yl)acetamide;
2-(4-chlorophenyl)-N-(1-oxo-4-phenyl-5,6,7,8-tetrahydrophthalazin-2(1H)-yl)acetamide;
2-(3,5-difluorophenyl)-N-(1-oxo-4-phenyl-1,5,6,7-tetrahydro-2H-cyclopenta[d]pyridazin-2-yl)acetamide;
2-(adamantan-1-yl)-N-(1-oxo-4-phenyl-1,5,6,7-tetrahydro-2H-cyclopenta[d]pyridazin-2-yl)acetamide;
2-(4-chlorophenyl)-N-(1-oxo-4-phenyl-1,5,6,7-tetrahydro-2H-cyclopenta[d]pyridazin-2-yl)acetamide;
2-(methylthio)-N-[1-oxo-4-(trifluoromethyl)phthalazin-2(1H)-yl]acetamide;
2-(adamantan-1-ylthio)-N-[1-oxo-4-(trifluoromethyl)phthalazin-2(1H)-yl]acetamide;
2-(adamantan-1-ylthio)-N-(1-oxo-4-phenylphthalazin-2(1H)-yl)acetamide; and
2-(1,3-benzodioxol-5-yl)-N-[4-(4-chlorophenyl)-1-oxophthalazin-2(1H)-yl]acetamide;
or pharmaceutically acceptable salts, solvates, or salts of solvates thereof.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It can be appreciated that two or more asymmetric centers can be present in the present compounds, hence several diastereomers and enantiomers of the exemplified structures can often be possible, and that pure diastereomers and enantiomers represent preferred embodiments. It is intended that pure diastereomers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein can exhibit the phenomenon of tautomerism and all tautomeric isomers and mixtures thereof are included in the scope of the invention.

Though structural representations within this specification can show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within drawings or the naming of the compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of KCNQ modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999)).

In addition, non-radioactive isotope-containing drugs, such as deuterated drugs called "heavy drugs," can be used for the treatment of diseases and conditions related to the activation of KCNQ channels. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions, potentially altering the pharmacokinetic profile or efficacy relative to the non-isotopic compound.

c. BIOLOGICAL DATA (i) In Vitro Assay

The following example describes the assay that can be used to identify compounds that activate KCNQ 2/3 channels.

HEK293 cells stably expressing human KCNQ2 and KCNQ3 subunits were seeded in 96-well, black-walled, clear-bottomed, poly-D-lysine coated plates (BD Biosciences, Bedford, Mass.) at a density of $1\times10^5$ cells per well 24 hours before the assay. On the assay day, BTC-AM dye (Invitrogen, Carlsbad, Calif.) was loaded into the cells by replacing the cell culture medium with 55 µL/well of 3 µg/mL dye in DPBS. Dye loading was allowed to proceed for 2 hours at room temperature and then cells were washed twice with 50 µL/well of assay buffer (in mM: 10 HEPES pH 7.3, 5 glucose, 140 Na-gluconate, 2.5 K-gluconate, 3.6 Ca-gluconate, 2 MgSO4, 0.1 Ouabain) to remove unloaded dye. Cells were incubated in 50 µL of assay buffer before loading onto a FLIPR system (Molecular Devices, Sunnyvale, Calif.). Various concentrations of compounds to be assayed were added to the cells in 50 µL of assay buffer and incubated for 4 minutes. The fluorescence signal was initiated by adding 100 µL of assay buffer containing 6 mM $TlNO_3$ and 10 mM $K_2SO_4$. Fluors were excited using the 488-nm line of an argon laser and emission was filtered using a 540±30 nm bandpass filter. Fluorescent signals were recorded for 3 minutes. Sums of the responses over basal responses were plotted versus concentrations of test compounds to obtain an $EC_{50}$ value. The maximum response for each test compound was determined relative to the response produced by 10 µM retigabine. The maximum response of retigabine at 10 µM was set at 100%.

$EC_{50}$ values and the maximum response of compounds described herein assessed by the above-described assays are shown in Table 1 wherein A represents $EC_{50}$ of less than about 100 nM;

B represents $EC_{50}$ between about 100 nM to less than about 500 nM;

C represents $EC_{50}$ between about 500 nM to less than about 1000 nM;

D represents $EC_{50}$ between about 1000 nM to less than about 10,000 nM; and

E represents $EC_{50}$ of about and greater than about 10,000 nM.

TABLE 1

| Example # | $EC_{50}$ | Max. % |
|---|---|---|
| 1 | B | 125 |
| 2 | B | 193 |
| 3 | B | 100 |
| 4 | B | 157 |
| 5 | B | 136 |
| 6 | A | 200 |
| 7 | D | 136 |
| 8 | D | 79 |
| 9 | C | 241 |
| 10 | D | 179 |
| 11 | B | 77 |
| 12 | B | 169 |
| 13 | B | 47 |
| 14 | B | 171 |
| 15 | A | 140 |
| 16 | B | 175 |
| 17 | A | 205 |

TABLE 1-continued

| Example # | EC$_{50}$ | Max. % |
|---|---|---|
| 18 | B | 189 |
| 19 | D | 45 |
| 20 | B | 123 |
| 21 | D | 82 |
| 22 | D | 63 |
| 23 | C | 156 |
| 24 | A | 235 |
| 25 | D | 139 |
| 26 | B | 157 |
| 27 | C | 92 |
| 28 | D | 121 |
| 29 | B | 173 |
| 30 | D | 94 |
| 31 | D | 30 |
| 32 | D | 46 |
| 33 | D | 140 |
| 34 | B | 184 |
| 35 | B | 192 |
| 36 | B | 155 |
| 37 | A | 179 |
| 38 | E | 126 |
| 39 | E | 11 |
| 40 | E | 7 |
| 42 | B | 103 |
| 43 | B | 112 |
| 44 | E | 35 |
| 45 | D | 84 |
| 47 | E | 7 |
| 48 | D | 77 |
| 49 | E | 3 |
| 50 | E | 116 |
| 51 | E | −2 |
| 52 | B | 116 |
| 53 | D | 61 |
| 54 | D | 84 |
| 55 | C | 72 |
| 56 | D | 51 |
| 57 | D | 85 |
| 58 | B | 137 |
| 59 | D | 90 |
| 60 | A | 214 |
| 61 | E | 26 |
| 62 | A | 149 |
| 63 | A | 160 |
| 64 | A | 157 |
| 65 | B | 151 |
| 66 | A | 148 |
| 67 | A | 166 |
| 68 | A | 164 |
| 69 | A | 138 |
| 70 | B | 124 |
| 71 | A | 162 |
| 72 | A | 130 |
| 73 | A | 142 |
| 74 | A | 165 |
| 75 | A | 243 |
| 76 | B | 157 |
| 77 | A | 145 |
| 78 | D | 140 |
| 79 | A | 144 |
| 80 | B | 80 |
| 81 | E | 50 |
| 82 | B | 156 |
| 83 | E | 13 |
| 84 | A | 134 |
| 85 | B | 117 |
| 86 | A | 166 |
| 87 | C | 104 |
| 88 | C | 60 |
| 89 | B | 118 |
| 90 | E | 1 |
| 91 | B | 101 |
| 93 | D | 149 |
| 98 | C | 80 |
| 99 | C | 81 |
| 100 | B | 79 |
| 101 | D | 57 |
| 102 | C | 112 |
| 103 | B | 140 |
| 104 | D | 97 |
| 105 | B | 84 |
| 107 | B | 98 |
| 108 | B | 96 |
| 109 | A | 138 |
| 110 | A | 120 |
| 111 | E | 25 |
| 112 | B | 92 |
| 113 | A | 154 |
| 114 | C | 119 |
| 115 | B | 69 |
| 116 | A | 132 |
| 117 | B | 120 |
| 118 | A | 128 |
| 119 | E | 12 |
| 120 | C | 103 |
| 121 | D | 201 |
| 123 | C | 48 |
| 124 | D | 33 |
| 125 | A | 150 |
| 126 | B | 153 |
| 127 | B | 101 |
| 128 | B | 140 |
| 129 | A | 143 |
| 130 | A | 156 |
| 131 | A | 150 |
| 132 | B | 123 |
| 133 | B | 144 |
| 134 | A | 192 |
| 135 | B | 95 |
| 136 | A | 130 |
| 137 | B | 95 |
| 138 | A | 129 |
| 139 | E | 20 |
| 140 | A | 126 |
| 141 | A | 130 |
| 142 | A | 109 |
| 143 | A | 128 |
| 144 | A | 139 |
| 145 | B | 101 |
| 146 | B | 83 |
| 147 | B | 154 |
| 148 | B | 114 |
| 149 | A | 133 |
| 150 | A | 138 |
| 151 | A | 141 |
| 152 | B | 114 |
| 153 | C | 143 |
| 154 | A | 136 |
| 155 | A | 165 |
| 156 | B | 177 |
| 157 | B | 155 |
| 158 | B | 167 |
| 159 | B | 156 |
| 160 | A | 157 |
| 161 | B | 145 |
| 162 | B | 164 |
| 163 | A | 177 |
| 164 | A | 155 |
| 165 | B | 112 |
| 166 | B | 161 |
| 167 | A | 144 |
| 168 | B | 134 |
| 169 | B | 139 |
| 170 | C | 104 |
| 171 | C | 134 |
| 172 | A | 195 |
| 173 | E | −12 |
| 174 | E | 20 |
| 175 | E | 13 |
| 176 | B | 33 |
| 177 | E | 48 |
| 178 | E | 56 |
| 179 | C | 169 |
| 180 | E | −3 |
| 181 | B | 166 |
| 182 | B | 122 |

TABLE 1-continued

| Example # | EC$_{50}$ | Max. % |
|---|---|---|
| 183 | B | 178 |
| 184 | A | 154 |
| 185 | A | 144 |
| 186 | B | 136 |
| 187 | B | 123 |
| 188 | D | 131 |
| 189 | B | 152 |
| 190 | D | 124 |
| 191 | E | 25 |
| 192 | B | 155 |
| 193 | B | 161 |
| 194 | C | 248 |

(ii) In Vivo Data

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

Capsaicin-Induced Secondary Mechanical Hypersensitivity:

Rats were allowed to acclimate to the study room for 1 h. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 minutes following capsaicin (Joshi et al 2006, Neuroscience 143, 587-596). Compounds were injected (i.p.) 30 minutes before testing (150 minutes post-capsaicin).

Tactile (mechanical) allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats. To evaluate the antinociceptive effects, animals were administered vehicle or test compound and tactile allodynia was assessed 30 minutes after i.p. administration.

Tactile allodynia was measured as described above. The compounds of Example 3 and Example 17 showed a statistically significant change in paw withdrawal latency versus vehicle at about 30 mg/kg.

Chronic Constriction Injury (CCI) Model of Neuropathic Pain (Bennett Model)

A model of chronic constriction injury-induced (CCI) neuropathic pain was produced by following the method of Bennett and Xie (1988, Pain, 33, 87-107). The right common sciatic nerve was isolated at mid-thigh level, and loosely ligated by 4 chromic gut (5-0) ties separated by an interval of 1 mm. The same procedure was performed on Sham rats, but without sciatic nerve constriction. All animals were left to recover for at least 2 weeks and no more than 5 weeks prior to testing of mechanical allodynia. Compounds were injected (i.p.) 30 minutes or more before testing. The compounds of Example 77, Example 117, Example 168, and Example 184 showed a statistically significant change in paw withdrawal latency versus vehicle at about 30 mg/kg.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) was used to test a compound of the present application The left L5 and L6 spinal nerves of the rat were isolated adjacent to the vertebral column and tightly ligated with a 5-0 silk suture distal to the DRG, and care taken to avoid injury of the L4 spinal nerve. The same procedure was performed on Sham rats, but without nerve ligation. All animals were allowed to recover for at least one week and not more than three weeks prior to assessment of tactile allodynia. The compounds of Example 91, Example 117, Example 88, and Example 150 showed a statistically significant change in paw withdrawal latency versus vehicle at about 30 mg/kg.

d. METHODS OF USING THE COMPOUNDS

In one aspect, the present invention provides methods of using one or more compounds or composition described herein to treat or prevent a disorder, disease or condition of a subject (including human), which disorder, disease, or condition is responsive to modulation of KCNQ potassium channels. In particular, compounds described herein are expected to have utility in the treatment of a disorder, disease or condition which is responsive to modulation of KCNQ potassium channels.

In one group of embodiments, diseases and conditions of humans or other animals that can be treated with activation of KCNQ channels, include, but are not limited to, diseases and conditions involving abnormal neuronal excitability such as but not limited to epilepsy, pain, migraine, anxiety, overactive bladder, schizophrenia, anxiety, and substance abuse.

One embodiment provides methods for treating pain (for example, neuropathic pain (including diabetic polyneuropathy), nociceptive pain, persistent pain, osteoarthritic pain, cancer pain, inflammatory pain, postoperative pain, fibromyalgia, chronic widespread pain, musculoskeletal pain, myofascial pain, Temporomandibular joint pain (TMJ pain), particularly, inflammatory pain, osteoarthritic pain, persistent pain, postoperative pain, cancer pain, neuropathic pain, or nociceptive pain) in mammals (including human) in need of such treatment. The methods comprise administering to the mammals therapeutically effective amounts of one or more compounds described herein, or pharmaceutically acceptable salts, solvates, or salts of solvates thereof, alone or in combination with one or more pharmaceutically acceptable carrier(s). The methods further comprise administration of compounds described herein as a single dose. The methods also comprise repeated or chronic administration of present compounds over a period of days, weeks, months, or longer. In certain embodiments, the method comprises administering to the mammal therapeutically effective amounts of one or more of the compounds described herein, or pharmaceutically acceptable salts or solvates thereof, in combination with one or more analgesics (for example, acetaminophen or opioids such as, but not limited to, morphine), or with one or more nonsteroidal anti-inflammatory drugs (NSAIDs); or administered with a combination of one or more analgesics and one or more NSAIDs. Examples of NSAIDs include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition can optionally include one or more pharmaceutically acceptable carriers.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the active ingredients can be required to achieve the desired therapeutic response. "Repeated or chronic administration" refers to the administration of the compositions described herein daily (i.e., every day) or intermittently (i.e., not every day) over a period of days, weeks, months, or longer. In particular, the treatment of chronic painful conditions is anticipated to require such repeated or chronic administration of the compositions described herein. Compounds of the invention can become more effective upon repeated or chronic administration such that the therapeutically effective doses on repeated or chronic administration can be lower than the therapeutically effective dose from a single administration.

Compounds can also be administered as a pharmaceutical composition comprising the compounds of interest in combination with one or more pharmaceutically acceptable carriers. The phrase "therapeutically effective amount" of the compound of the invention means a sufficient amount of the compound to treat disorders or, or to prevent development of or alleviate to some extent one or more of the symptoms of the condition or disorder being treated, at a reasonable benefit/risk ratio applicable to any medical treatment. It can be understood, however, that the total daily usage of the compounds and compositions of the invention can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds can be administered alone, or in combination (i.e. co-administered) with one or more additional pharmaceutical agents. For example, one or more present compounds or pharmaceutically acceptable salts or solvates thereof, can be administered in combination with one or more analgesics (e.g acetaminophen or opioids), or with one or more nonsteroidal anti-inflammatory drugs (NSAIDs), or mixtures thereof. Non limiting examples of suitable NSAIDs include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) can be administered to the patient together, in a single oral dosage composition having a fixed ratio of each active ingredient, such as a tablet or capsule; or each active ingredient can be administered in separate oral dosage formulations.

Separate dosage formulations can be administered at essentially the same time (e.g., concurrently) or at separately staggered times (e.g., sequentially).

Therapeutically effective amounts can be determined by those skilled in the art, and can be adjusted to the requirements of each particular case. Generally, a therapeutically effective amount of a KCNQ modulator can range from a total daily dose, for example in human or other animals, of about 0.01 mg/kg body weight to about 100 mg/kg body weight, preferably of about 0.03 mg/kg body weight to about 30 mg/kg body weight. If desired, the effective daily dose can be divided into multiple doses for purposes of administration. Consequently, single dose compositions can contain such amounts or submultiples thereof to make up the daily dose. It is understood that the effective daily dose can vary with the duration of the treatment.

e. PHARMACEUTICAL COMPOSITIONS

Pharmaceutical compositions comprising compounds described herein or pharmaceutically acceptable salts, solvates, or salts of solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts, solvates, or salts of solvates thereof, and one or more pharmaceutically acceptable carriers, alone or in combination with one or more analgesics (e.g. acetaminophen or opioids), or in combination with one or more nonsteroidal anti-inflammatory drugs (NSAIDs), or a combination of one or more analgesics and one or more NSAIDs.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound can be mixed under sterile conditions with a pharmaceutically acceptable carrier and any needed preservatives, buffers or propellants which can be required. Opthalmic formulations, eye ointments, powders and solutions are also contemplated as being within the scope of this invention.

Compounds described herein can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. GENERAL SYNTHESIS

Compounds described herein when prepared by synthetic processes or by metabolic processes are encompassed in this application. Preparation of the compounds by metabolic processes includes those occurring in the human or animal body (in vivo) or processes occurring in vitro.

The compounds can be prepared by a variety of processes well known for the preparation of compounds of this class. For example, the compounds of formula (I) wherein the groups $Z^1$, $R^1$, $R^3$, $R^4$, and p have the meanings as set forth in the summary section unless otherwise noted, can be synthesized as shown in Schemes 1-6.

Abbreviations which have been used in the descriptions of the Schemes and the Examples that follow are: DMSO-$d_6$ for deuterated dimethyl sulfoxide, EDC for 1-(3-dimethylaminopropyl)-3-ethylcarbodiimide hydrochloride, EtOAc for ethyl acetate, Et$_2$O for diethyl ether, EtOH for ethanol, iPrMgBr for isopropyl magnesium bromide, iPr$_2$Zn for diisopropyl zinc, KOtBu for potassium tert-butoxide, THF for tetrahydrofuran, MeOH for methanol, DMAP for 4-(dimethylamino)pyridine, DMF for N,N-dimethylformamide, PdCl$_2$(dppf) for [1,1'-bis(diphenylphosphino)ferrocene]dichloropalladium(II), Pd(PPh$_3$)$_4$ for tetrakis(triphenylphosphine)palladium(0), Pd(OAc)$_2$ for palladium (II) acetate, PhMgBr for phenyl magnesium bromide, and n-BuLi for n-butyllithium.

Compounds of general formula (I) can be prepared, for example, using the general method outlined in Scheme 1.

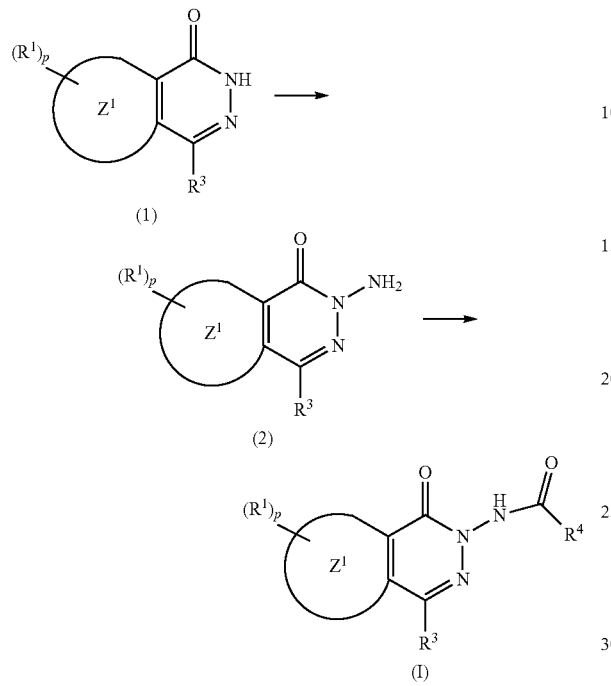

Compounds of formula (I) can be converted to compounds of formula (2) by treatment with a suitable base such as, but not limited to, potassium tert-butoxide or sodium hydride followed by (diphenylphosphoryl)hydroxylamine (Klotzer, W.; Stadlwieser, J.; Raneburger, J. *Organic Syntheses* 1986, 64, 96-103), in solvents such as, but not limited to, tetrahydrofuran, dimethoxyethane, and N,N-dimethylformamide. Reactions are typically conducted at about room temperature.

Compounds of formula (2) when treated with compounds of formula $R^4COX^{101}$, wherein $X^{101}$ is chloro, bromo, or OH under coupling conditions known to one skilled in the art, can provide compounds of general formula (I). Typical conditions for the reaction of (2) with compounds of formula $R^4COX^{101}$, wherein $X^{101}$ is chloro or bromo include, but are not limited to, stirring about an equimolar mixture of the compounds in a solvent such as, but not limited to, chloroform, dichloromethane, THF, or mixture thereof, optionally in the presence of a base such as, but not limited to, diisopropylethylamine or pyridine, at about 0° C. to about 30° C. for about 8-24 hours. Acid coupling conditions for compounds of formula $R^4COX^{101}$ wherein $X^{101}$ is —OH and compounds of formula (2), include stirring about an equimolar mixture of the compounds in a solvent such as, but not limited to, THF, N,N-dimethylacetamide, N,N-dimethylformamide, pyridine, chloroform, or mixtures thereof, with a coupling reagent, optionally along with a coupling auxiliary, and in the presence or absence of a base. Typical reactions can be carried out at temperatures ranging from about 0° C. to about 65° C. or can be carried out in a microwave reactor to facilitate the coupling. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 1-propanephosphonic acid cyclic anhydride. Non limiting examples of a coupling auxiliary include 1-hydroxy-7-azabenzotriazole (HOAT) and 1-hydroxybenzotriazole hydrate (HOBT). Suitable examples of bases include, but are not limited to, N-methylmorpholine and diisopropylethylamine.

Compounds of general formula (1) can be purchased from commercial sources or prepared using one of the methods outlined in the Schemes 2-4 below.

Compounds of general formula (1) can be prepared using the two-step method outlined in Scheme 2.

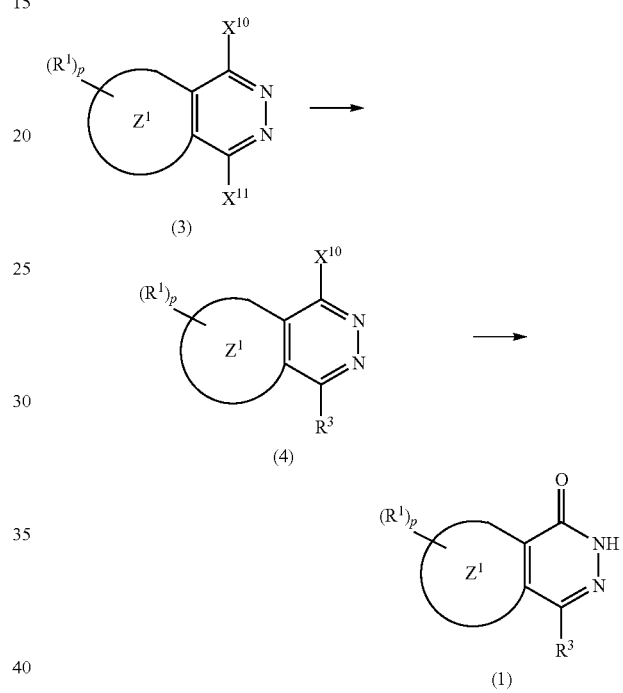

Compounds of formula (3) wherein $X^{10}$ and $X^{11}$ are chloro or bromo, can be converted to compounds of formula (4) by reaction with an organozinc reagent such as, for example, a reagent $Zn(R^3)_2$, wherein $R^3$ is alkyl, alkynyl, aryl, or heteroaryl. The reaction is conducted in the presence of a palladium catalyst such as, but not limited to, $PdCl_2dppf.CH_2Cl_2$ or $Pd(PPh_3)_4$ in a solvent such as, but not limited to, dioxane, tetrahydrofuran, toluene and N,N-dimethylformamide, or mixtures thereof; at temperatures from about 50° C. to about 100° C.; however, elevated temperatures or microwave irradiation can be beneficial. Similar coupling reactions are reported using arylboronic acid derivatives (see Villemin, D.; Jullien, A.; Bar, N.; *Tetrahedron Letters* 2007; 48, 4191-4193) and alkenylstannanes (see Matulenko, M. A.; Lee, C.-H.; Jiang, M.; Frey, R. R.; Cowart, M. D.; Bayburt, E. K.; DiDomenico, S.; Gfesser, G. A.; Gomtsyan, A.; Zheng, G. Z.; McKie, J. A.; et al.; *Bioorganic Medicinal Chemistry* 2005, 13, 3705-3720) under Pd-catalyzed conditions as well. Additionally, electrophilic aryl and heteroaryl substitutions have been accomplished using Lewis acids such as $AlCl_3$ (see Coates, W. J.; McKillop, A.; *Journal of Organic Chemistry* 1990, 55, 5418-5420).

Compounds of formula (4) can be converted to compounds of formula (1) by reaction with sodium acetate in acetic acid with heating from about 50° C. to about 120° C.

Compounds of formula (1) can be prepared using the method outlined in Scheme 3.

Scheme 3

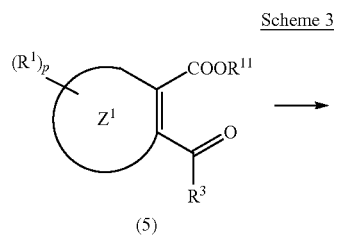

(5)

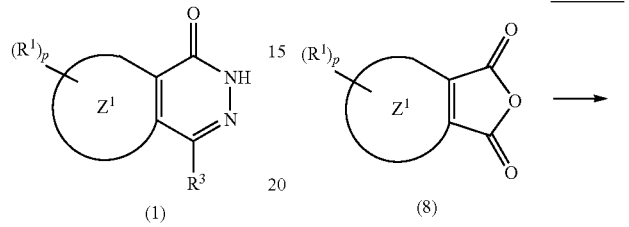

(1)

Compounds of formula (5) wherein $R^{11}$ is hydrogen or alkyl, can be converted to compounds of formula (1) by reaction with hydrazine in a solvent such as, but not limited to, methanol or ethanol; at temperatures from about room temperature to about 100° C. Typically, the reaction is conducted in ethanol at about 80° C. Compounds of formula (5) can be purchased from commercial sources, or prepared using methods set forth herein below.

Compounds of formula (1) can be prepared using the method outlined in Scheme 4.

Scheme 4

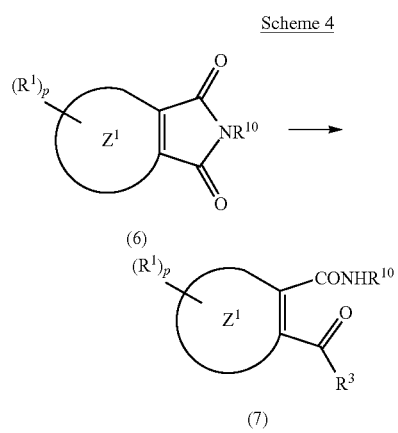

(6)

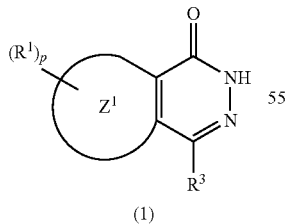

(7)

(1)

Compounds of formula (6) wherein $R^{10}$ is aryl or alkyl, can be converted to compounds of formula (7) by reaction with a Grignard reagent $R^3MgBr$, wherein $R^3$ is alkyl or aryl; in a solvent such as, but not limited to, tetrahydrofuran or diethyl ether; at temperatures ranging from about −78° C. to about room temperature. Compounds of formula (7) can be converted to compounds of formula (1) by reaction with hydrazine in a solvent such as, but not limited to, methanol or ethanol; at temperatures ranging from about room temperature to about 100° C.; and in the presence of a catalytic amount of acid such as, but not limited to, hydrochloric acid. The reaction can also be conducted at temperatures up to around 200° C. in a sealed vessel with microwave irradiation.

Compounds of formula (5) can be prepared using the method outlined in Scheme 5.

Scheme 5

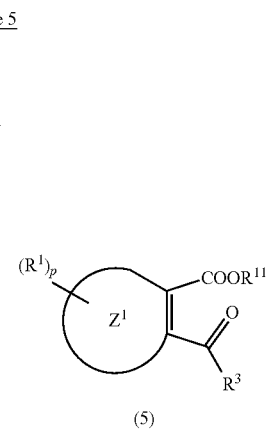

(8)

(5)

Compounds of formula (8) can be converted to compounds of formula (5) wherein $R^3$ is aryl and $R^{11}$ is hydrogen under Friedel-Crafts acylation reaction conditions. This reaction is well known to those skilled in the art and typically involves reaction with a Lewis acid such as, but not limited to, aluminum trichloride, and an aryl reactant (e.g., benzene, toluene). This class of chemical reaction is described more fully in Jerry March, *Advanced Organic Chemistry: Reactions, Mechanisms and Structure,* 4th Ed, pp. 539-542.

Compounds of formula (5) can be prepared using the method outlined in Scheme 6.

Scheme 6

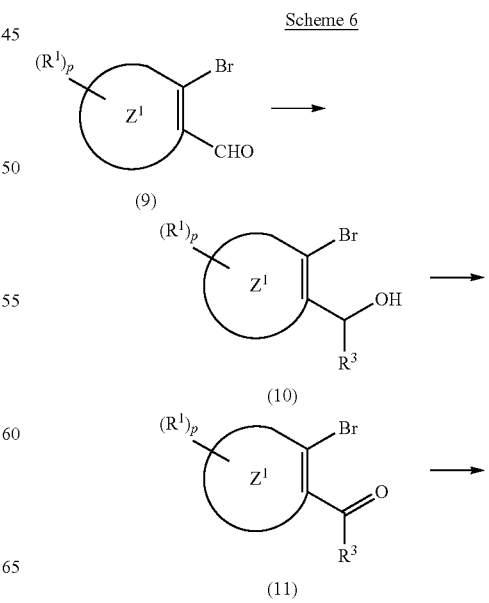

(9)

(10)

(11)

-continued

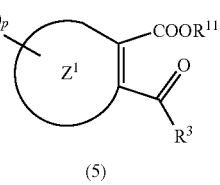

(5)

Compounds of formula (9) wherein $R^3$ is alkyl, haloalkyl, or aryl can be converted to compounds of formula (10) by reaction with a Grignard reagent $R^3MgBr$ or silane $R^3SiMe_3$; in a solvent such as, but not limited to, tetrahydrofuran or diethylether; at temperatures ranging from about −78° C. to about room temperature. Compounds of formula (10) can be converted to compounds of formula (11) by an oxidation reaction. This reaction is well known to those skilled in the art and numerous reagents are known that effectuate the oxidation of an alcohol to a ketone (e.g., $MnO_2$, Dess-Martin periodinane, pyridinium chlorochromate, $KMnO_4$). This class of chemical reaction is described more fully in Jerry March, *Advanced Organic Chemistry: Reactions, Mechanisms and Structure*, 4th Ed, pp. 1167-1171. Compounds of formula (11) can be converted to compounds of formula (5), wherein $R^{11}$ is alkyl, by reaction with carbon monoxide in the presence of a palladium catalyst, an alcohol $R^{11}OH$, and a base such as, but not limited to, triethylamine. Suitable palladium catalysts include, but are not limited to $PdCl_2dppf.CH_2Cl_2$, $Pd(OAc)_2$, and $PdCl_2(PPh_3)_2$. The reaction can be performed at room temperature or at temperatures up to about 100° C. in a solvent such as N,N-dimethylformamide, methanol, ethanol, and the like.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

The following examples can be used for illustrative purposes and should not be deemed to narrow the scope of the invention. All experiments were conducted at room temperature unless otherwise stated.

g. EXAMPLES

Example 1

2-(4-chlorophenyl)-N-(4-isopropyl-1-oxophthalazin-2(1H)-yl)acetamide

Example 1A 4-isopropylphthalazin-1(2H)-one

A solution of isopropylmagnesium bromide in THF (1M, 6.4 mL, 6.4 mmol) was added to a solution of 2-methylisoindoline-1,3-dione (0.793 g, 4.92 mmol) in THF (15 mL) at 0° C., stirred for 15 minutes, concentrated, dissolved in EtOH (12 mL) with a catalytic amount of concentrated HCl. Hydrazine hydrate (0.58 mL, 15 mmol) was added, and mixture was microwaved at 180° C. for 30 minutes, concentrated, and chromatographed on $SiO_2$ (33% EtOAc/hexane) to give the title compound as a white solid (0.591 g, 3.14 mmol). $^1$H NMR (300 MHz, DMSO-d$_6$) δ 12.47 (s, 1H), 8.28 (dd, 1H), 8.06 (d, 1H), 7.94 (ddd, 1H), 7.85 (ddd, 1H), 3.57 (quin, 1H), 1.27 (d, 6H); LC/MS (APCI) M/Z 189.1 (M+H)$^+$.

Example 1B 2-amino-4-isopropylphthalazin-1(2H)-one

A mixture of the product of Example 1A (30.0 mg, 0.159 mmol) and KOtBu (1 M in THF, 0.32 mL, 0.32 mmol) in THF (1 mL) was stirred for 45 minutes, and O-(diphenylphosphoryl)hydroxylamine (57.6 mg, 0.247 mmol) [Klotzer, W.; Stadlwieser, J.; Raneburger, J. *Organic Syntheses* 1986, 64, 96-103] was added and stirred overnight. The mixture was diluted with EtOAc, washed with saturated aqueous $NaHCO_3$ and brine, dried ($Na_2SO_4$), and concentrated to give 35.3 mg of crude product as a tan solid, which was used without purification. $^1$H NMR (300 MHz, DMSO-d$_6$) δ 8.31 (dd, 1H), 8.09 (d, 1H), 7.92 (ddd, 1H), 7.84 (ddd, 1H), 6.31 (s, 2H), 3.63 (quin, 1H), 1.30 (d, 6H); LC/MS (APCI) M/Z 204.1 (M+H)$^+$.

Example 1C 2-(4-chlorophenyl)-N-(4-isopropyl-1-oxophthalazin-2(1H)-yl)acetamide

Example 1B was dissolved in CH$_2$Cl$_2$ (0.5 mL), to which was added a catalytic amount of DMAP, pyridine (0.017 mL, 0.21 mmol), and 2-(4-chlorophenyl)acetyl chloride (0.025 mL, 0.17 mmol). The mixture was stirred for 1 hour, diluted with EtOAc, washed with saturated aqueous NaHCO$_3$ and brine, dried (Na$_2$SO$_4$), and filtered. The residue was chromatographed on SiO$_2$ (5-10% EtOAc/CH$_2$Cl$_2$ gradient elution) to give the title compound (0.0405 g, 0.114 mmol) as a white solid. $^1$H NMR (300 MHz, DMSO-d$_6$) δ 11.50 (s, 1H), 8.32 (dd, 1H), 8.11 (d, 1H), 8.00 (td, 1H), 7.89 (ddd, 1H), 7.41 (s, 4H), 3.68 (s, 2H), 3.60 (quin, 1H), 1.26 (d, 6H); MS (ESI$^-$) M/Z 354.0 (M-H)$^-$.

Example 2

2-(1-adamantyl)-N-[4-(4-bromophenyl)-1-oxophthalazin-2(1H)-yl]acetamide

Example 2A 2-amino-4-(4-bromophenyl)phthalazin-1(2H)-one

A mixture of 4-(4-bromophenyl)phthalazin-1(2H)-one (Aldrich) (0.200 g, 0.663 mmol) and KOtBu (1 M in THF, 1.0 mL, 1.0 mmol) in THF (2 mL) was stirred for 45 minutes, diluted with DMF (1 mL), and O-(diphenylphosphoryl)hydroxylamine (0.240 g, 1.03 mmol) was added and stirred for 90 minutes. The mixture was diluted with EtOAc, washed with saturated aqueous NaHCO$_3$ and brine, dried (Na$_2$SO$_4$), and concentrated to give 302 mg of crude material as a white solid, which was used without purification. LC/MS (APCI) M/Z 318.0 (M+H)$^+$.

Example 2B 2-(1-adamantyl)-N-[4-(4-bromophenyl)-1-oxophthalazin-2(1H)-yl]acetamide Example 2A (59.8 mg) was dissolved in CH$_2$Cl$_2$ (0.5 mL), to which was added pyridine (0.015 mL, 0.19 mmol), and (adamantan-1-yl)acetyl chloride (0.040 g, 0.19 mmol). The mixture was stirred for 2 hours, diluted with EtOAc, washed with saturated aqueous NaHCO$_3$ and brine, dried (Na$_2$SO$_4$), and filtered. The residue was chromatographed on SiO$_2$ (7% EtOAc/CH$_2$Cl$_2$) to give the title compound (0.031 g, 0.063 mmol) as a white solid. $^1$H NMR (300 MHz, DMSO-d$_6$) δ 11.27 (s, 1H), 8.45-8.35 (m, 1H), 8.00-7.89 (m, 2H), 7.78 (d, J=8.4 Hz, 2H), 7.75-7.69 (m, 1H), 7.56 (d, J=8.4 Hz, 2H), 2.05 (s, 2H), 1.97 (m, 3H), 1.68 (m, 12H); MS (ESI$^-$) M/Z 490.0 (M-H)$^-$.

Example 3

N-[4-(4-bromophenyl)-1-oxophthalazin-2(1H)-yl]-2-(4-chlorophenyl)acetamide

Example 2A (0.244 g) was dissolved in CH$_2$Cl$_2$ (2 mL), to which was added pyridine (0.060 mL, 0.74 mmol), and 2-(4-chlorophenyl)acetyl chloride (0.090 mL, 0.61 mmol). The mixture was stirred for 2 hours, diluted with EtOAc, washed with saturated aqueous NaHCO$_3$ and brine, dried (Na$_2$SO$_4$), and filtered. The residue was chromatographed on SiO$_2$ (7-10% EtOAc/CH$_2$Cl$_2$ gradient elution) to give the title compound (0.120 g, 0.256 mmol) as a white solid. $^1$H NMR (300 MHz, DMSO-d$_6$) δ 11.72 (s, 1H), 8.46-8.35 (m, 1H), 8.02-7.90 (m, 2H), 7.77 (d, 2H), 7.75-7.69 (m, 1H), 7.55 (d, 2H), 7.40 (s, 4H), 3.70 (s, 2H); MS (ESI$^-$) M/Z 468 (M-H)$^-$.

Example 4

2-(4-chlorophenyl)-N-(1-oxo-4-phenylphthalazin-2(1H)-yl)acetamide

A suspension of the product of Example 3 (29.9 mg, 0.064 mmol) and 10% Pd/C (catalytic amount) in MeOH (1 mL) was stirred under H$_2$ (1 atm) overnight, filtered though Celite, and concentrated to give the title compound (24.9 mg, 0.064 mmol) as a tan solid. $^1$H NMR (300 MHz, DMSO-d$_6$) δ 11.70 (s, 1H), 8.45-8.35 (m, 1H), 8.01-7.90 (m, 2H), 7.76-7.68 (m, 1H), 7.58 (s, 5H), 7.40 (s, 4H), 3.70 (s, 2H); MS (ESI$^-$) M/Z 388 (M-H)$^-$.

Example 5

2-(3,5-difluorophenyl)-N-(4-isopropyl-1-oxophthalazin-2(1H)-yl)acetamide

A mixture of the product of Example 1B (44.5 mg, 0.219 mmol), triethylamine (0.050 mL, 0.36 mmol), 2-(3,5-difluorophenyl)acetic acid (41.0 mg, 0.238 mmol), and O-(benzotriazol-1-yl)-N,N,N',N'-tetramethyluronium tetrafluoroborate (77.5 mg, 0.241 mmol) in DMF (0.75 mL) was stirred overnight, diluted with EtOAc, washed with 1 N NaOH and brine, dried (Na$_2$SO$_4$), and filtered. The residue was chromatographed on SiO$_2$ (8% EtOAc/CH$_2$Cl$_2$) to give the title compound as a white solid (25.4 mg, 0.071 mmol). $^1$H NMR (300 MHz, DMSO-d$_6$) δ 11.59 (s, 1H), 8.33 (dd, 1H), 8.16-8.09 (m, 1H), 8.00 (td, 1H), 7.89 (ddd, 1H), 7.19-7.07 (m, 3H), 3.75 (s, 2H), 3.61 (quin, 1H), 1.27 (d, 6H); MS (ESI$^+$) M/Z 357.9 (M+H)$^+$.

Example 6

2-(1-adamantyl)-N-(4-isopropyl-1-oxophthalazin-2(1H)-yl)acetamide

A mixture of the product of Example 1B (45.4 mg, 0.223 mmol), pyridine (0.023 mL, 0.28 mmol), and (adamantan-1-yl)acetyl chloride (0.052 g, 0.24 mmol) in CH$_2$Cl$_2$ (0.8 mL) was stirred for 2 hours, diluted with EtOAc, washed with saturated aqueous NaHCO$_3$ and brine, dried (Na$_2$SO$_4$), and filtered. The residue was chromatographed on SiO$_2$ (eluted with 8% EtOAc/CH$_2$Cl$_2$) to give the title compound (0.0743 g, 0.196 mmol) as a white solid. $^1$H NMR (300 MHz, DMSO-d$_6$) δ 11.09 (s, 1H), 8.35 (dd, 1H), 8.10 (d, 1H), 7.98 (td, 1H), 7.89 (ddd, 1H), 3.62 (quin, 1H), 2.03 (s, 2H), 1.95 (s, 3H), 1.76-1.52 (m, 12H), 1.26 (d, 6H); MS (ESI$^-$) M/Z 378.1 (M-H)$^-$.

Example 7

2-(1-adamantyl)-N-(8-oxo-5-phenylpyrido[2,3-d]pyridazin-7(8H)-yl)acetamide

Example 7A 5-phenylpyrido[2,3-d]pyridazin-8-ol

A mixture of 3-benzoylpicolinic acid (0.272 g, 0.120 mmol) and hydrazine hydrate (0.17 mL, 0.37 mmol) in EtOH (3.3 mL) was stirred at 80° C. overnight, concentrated, diluted with saturated aqueous NaHCO$_3$, extracted with CH$_2$Cl$_2$, dried (Na$_2$SO$_4$), and concentrated to give the title compound as a white solid (0.28 g, 0.12 mmol). $^1$H NMR (300 MHz, DMSO-d$_6$) δ 13.09 (s, 1H), 9.10 (dd, 1H), 8.09 (dd, 1H), 7.88 (dd, 1H), 7.54-7.63 (m, 5H).

Example 7B 7-amino-5-phenylpyrido[2,3-d]pyridazin-8(7H)-one

Example 7A was dissolved in THF (2.5 mL) and DMF (2.5 mL), and KOtBu (1 M in THF, 1.4 mL, 1.4 mmol) was added and stirred for 30 minutes. To this mixture was added O-(diphenylphosphoryl)hydroxylamine (0.320 g, 1.37 mmol), and the mixture was stirred for 4 hours, diluted with EtOAc, washed with saturated aqueous NaHCO$_3$ and brine, dried (Na$_2$SO$_4$), and filtered. The residue was chromatographed on SiO$_2$ (7% EtOAc/CH$_2$Cl$_2$) to give the title compound (0.081 g, 0.34 mmol) as a white gum LC/MS (APCI) M/Z 239.1 (M+H)$^+$.

Example 7C 2-(1-adamantyl)-N-(8-oxo-5-phenylpyrido[2,3-d]pyridazin-7(8H)-yl)acetamide A mixture of Example 7B (34.8 mg, 0.146 mmol), pyridine (0.014 mL, 0.18 mmol), and (adamantan-1-yl)acetyl chloride (35.2 mg, 0.165 mmol) in CH$_2$Cl$_2$ (0.45 mL) was stirred for 2 hours, diluted with EtOAc, washed with saturated aqueous NaHCO$_3$ and brine, dried (Na$_2$SO$_4$), and filtered. The residue was chromatographed on SiO$_2$ (3% MeOH/CH$_2$Cl$_2$) to give the title compound (43.9 mg, 0.106 mmol) as a white solid. $^1$H NMR (300 MHz, DMSO-d$_6$) δ 11.35 (s, 1H), 9.15 (dd, 1H), 8.16 (dd, 1H), 7.94 (dd, 1H), 7.65-7.54 (m, 5H), 2.08 (s, 2H), 1.95 (s, 3H), 1.74-1.53 (m, 12H); MS (DCI) M/Z 432.2 (M+NH$_4$).

Example 8

2-(1-adamantyl)-N-(4-isopropyl-1-oxo-5,6,7,8-tetrahydro-5,8-ethanophthalazin-2(1H)-yl)acetamide Example 8A 4-isopropyl-1-chloro-5,6,7,8-tetrahydro-5,8-ethanophthalazine A solution of 1,4-dichloro-5,6,7,8-tetrahydro-5,8-ethanophthalazine (Alfa Aesar) (0.109 g, 0.474 mmol), iPr$_2$Zn (1 M in toluene, 0.50 mL, 0.50 mmol), PdCl$_2$dppf CH$_2$Cl$_2$ (19.3 mg, 0.024 mmol) in dioxane (1.5 mL) was stirred at 80° C. for 2.5 hours, quenched with 1 N HCl, diluted with EtOAc, washed with saturated aqueous NaHCO$_3$ and brine, dried (Na$_2$SO$_4$), and filtered. The residue was chromatographed on SiO$_2$ (10% Et$_2$O/CH$_2$Cl$_2$ to 5% MeOH/CH$_2$Cl$_2$) to give impure title compound as a tacky solid (34.9 mg). LC/MS (APCI) M/Z 237.1 (M+H)$^+$.

Example 8B 4-isopropyl-1-oxo-5,6,7,8-tetrahydro-5,8-ethanophthalazine

A mixture of Example 8A and sodium acetate (25.4 mg, 0.310 mmol) in acetic acid (1.5 mL) was stirred at 115° C. for 3 hours, diluted with water, neutralized with Na$_2$CO$_3$, extracted with EtOAc, washed with brine, dried (Na$_2$SO$_4$), and concentrated to give 31.5 mg of title compound as a white solid. LC/MS (APCI) M/Z 219.2 (M+H)$^+$.

Example 8C 2-amino-4-isopropyl-1-oxo-5,6,7,8-tetrahydro-5,8-ethanophthalazine

A mixture of Example 8B (31.5 mg, 0.144 mmol) and KOtBu (1 M in THF, 0.16 mL, 0.16 mmol) in THF (0.3 mL) and DMF (0.2 mL) was stirred for 30 minutes, and O-(diphenylphosphoryl)hydroxylamine (37.0 mg, 0.159 mmol) was added and stirred 4 h. The mixture was diluted with EtOAc, washed with saturated aqueous NaHCO$_3$ and brine, dried (Na$_2$SO$_4$), and filtered. The residue was chromatographed on SiO$_2$ (2.5% MeOH/CH$_2$Cl$_2$) to give the title compound as a white solid (18.3 mg) which was used without further purification. LC/MS (APCI) M/Z 234.2 (M+H)$^+$.

Example 8D 2-(1-adamantyl)-N-(4-isopropyl-1-oxo-5,6,7,8-tetrahydro-5,8-ethanophthalazin-2(1H)-yl)acetamide A mixture of Example 8C (18.3 mg), pyridine (0.008 mL, 0.10 mmol), and (adamantan-1-yl)acetyl chloride (18.7 mg, 0.088 mmol) in CH$_2$Cl$_2$ (0.35 mL) was stirred for 2 hours, diluted with EtOAc, washed with saturated aqueous NaHCO$_3$ and brine, dried (Na$_2$SO$_4$), and filtered. The residue was chromatographed on SiO$_2$ (20% EtOAc/CH$_2$Cl$_2$) to give the title compound (17.6 mg, 0.043 mmol) as a white solid. $^1$H NMR (300 MHz, DMSO-d$_6$) δ 10.95 (s, 1H), 3.40-3.35 (m, 1H), 3.21-3.07 (m, 2H), 1.99 (s, 2H), 1.93 (s, 3H), 1.83-1.72 (m, 4H), 1.72-1.54 (m, 12H), 1.33-1.17 (m, 4H), 1.14 (d, 6H); MS (ESI$^+$) M/Z 410.1 (M+H)$^+$.

Example 9

2-(1-adamantyl)-N-(4-oxo-7-phenylthieno[2,3-d]pyridazin-5(4H)-yl)acetamide

Example 9A 7-phenylthieno[2,3-d]pyridazin-4(5H)-one

A solution of n-BuLi (2.5 M in hexanes, 3.44 mL, 8.6 mmol) was added to diisopropylamine (1.25 mL, 8.9 mmol) in THF (5 mL) at 0° C. and stirred for 15 minutes. This solution was added quickly to a 0° C. solution of thiophene-3-carboxylic acid (0.500 g, 3.91 mmol) in THF (20 mL), and stirred for 5 min. Benzoic anhydride (0.972 g, 4.30 mmol) was then added, the ice bath was removed, and the mixture was stirred overnight, concentrated, dissolved in EtOH (25 mL), stirred with hydrazine hydrate (1.35 mL, 23.9 mmol) at 80° C. for 7 h, concentrated, and diluted with EtOAc, washed with saturated aqueous NaHCO$_3$ and brine, dried (Na$_2$SO$_4$), and filtered. The residue was chromatographed on SiO$_2$ (5% MeOH/CH$_2$Cl$_2$) to give impure title compound (84.4 mg, 0.370 mmol) as a white solid. LC/MS (APCI) M/Z 229.0 (M+H)$^+$.

Example 9B 5-amino-7-phenylthieno[2,3-d]pyridazin-4(5H)-one

A mixture of Example 9A (69.1 mg, 0.303 mmol) and KOtBu (1 M in THF, 0.35 mL, 0.35 mmol) in THF (1.5 mL)

was stirred for 60 min, and O-(diphenylphosphoryl)hydroxylamine (81.0 mg, 0.348 mmol) and DMF (1.5 mL) were added and stirred 1 hour. The mixture was diluted with EtOAc, washed with 1 N NaOH and water, dried ($Na_2SO_4$), filtered, and concentrated to give the title compound as a white solid (62.6 mg), which was used without purification. $^1$H NMR (300 MHz, DMSO-$d_6$) δ 8.16 (d, 1H), 7.89-7.82 (m, 2H), 7.75 (d, 1H), 7.64-7.51 (m, 3H), 6.65 (s, 2H); LC/MS (APCI) M/Z 244.1 (M+H)$^+$.

Example 9C 2-(1-adamantyl)-N-(4-oxo-7-phenylthieno[2,3-d]pyridazin-5(4H)-yl)acetamide A mixture of the product from Example 9B (31 mg), pyridine (0.012 mL, 0.15 mmol), and (adamantan-1-yl)acetyl chloride (31 mg, 0.15 mmol) in $CH_2Cl_2$ (0.4 mL) was stirred for 2 hours, diluted with EtOAc, washed with saturated aqueous $NaHCO_3$ and brine, dried ($Na_2SO_4$), and filtered. The residue was chromatographed on $SiO_2$ (10% EtOAc/$CH_2Cl_2$) to give the title compound (27.7 mg, 0.066 mmol) as a white solid. $^1$H NMR (300 MHz, DMSO-$d_6$) δ 11.31 (s, 1H), 8.23 (d, J=5.2 Hz, 1H), 7.86-7.78 (m, 3H), 7.65-7.55 (m, 3H), 2.07 (s, 2H), 1.95 (s, 3H), 1.76-1.53 (m, 12H); MS (ESI$^+$) M/Z 420.3 (M+H)$^+$.

Example 10

2-(3,5-difluorophenyl)-N-(4-oxo-7-phenylthieno[2,3-d]pyridazin-5(4H)-yl)acetamide A mixture of the product of Example 9B (31.6 mg, 0.13 mmol), triethylamine (0.028 mL, 0.20 mmol), 2-(3,5-difluorophenyl)acetic acid (25.4 mg, 0.15 mmol), and O-(benzotriazol-1-yl)-N,N,N',N'-tetramethyluronium tetrafluoroborate (49.8 mg, 0.16 mmol) in DMF (0.4 mL) was stirred overnight, diluted with EtOAc, washed with 1 N NaOH and brine, dried ($Na_2SO_4$), and filtered. The residue was chromatographed on $SiO_2$ (12% EtOAc/$CH_2Cl_2$) to give the title compound as a white solid (6.2 mg, 0.016 mmol). $^1$H NMR (300 MHz, DMSO-$d_6$) δ 11.80 (s, 1H), 8.24 (d, J=5.2 Hz, 1H), 7.87-7.77 (m, 3H), 7.64-7.55 (m, 3H), 7.22-7.08 (m, 3H), 3.78 (s, 2H); MS (ESI$^-$) M/Z 396.1 (M−H)$^-$.

Example 11

2-(3,5-difluorophenyl)-N-[1-oxo-4-(trifluoromethyl)phthalazin-2(1H)-yl]acetamide

Example 11A 4-(trifluoromethyl)phthalazin-1(2H)-one

A solution of 2-(2,2,2-trifluoroacetyl)benzoic acid (0.554 g, 2.54 mmol) and hydrazine hydrate (0.44 mL, 7.8 mmol) in EtOH (7.5 mL) was stirred at 80° C. overnight, concentrated, azeotroped with toluene, and dried in vacuo to give the crude title compound as a tan solid, which was used without purification). $^1$H NMR (300 MHz, DMSO-$d_6$) δ 8.36 (dd, 1H), 7.91-8.10 (m, 3H).

Example 11B 2-amino-4-(trifluoromethyl)phthalazin-1(2H)-one

A mixture of Example 11A and KOtBu (1 M in THF, 2.8 mL, 2.8 mmol) in THF (5 mL) was stirred for 60 min, and O-(diphenylphosphoryl)hydroxylamine (0.680 mg, 0.348 mmol) was added and stirred for 1 hour. The mixture was diluted with EtOAc, washed with 1 N NaOH and water, dried ($Na_2SO_4$), and concentrated to give the title compound as a white solid (402 mg) which was used without purification. $^1$H NMR (300 MHz, DMSO-$d_6$) δ 8.45-8.35 (m, 1H), 8.10-7.92 (m, 3H), 6.58 (s, 2H).

Example 11C 2-(3,5-difluorophenyl)-N-[1-oxo-4-(trifluoromethyl)phthalazin-2(1H)-yl]acetamide A mixture of the product of Example 11B (40.3 mg, 0.18 mmol), triethylamine (0.037 mL, 0.26 mmol), 2-(3,5-difluorophenyl)acetic acid (36.4 mg, 0.21 mmol), and O-(benzotriazol-1-yl)-N,N,N',N'-tetramethyluronium tetrafluoroborate (61.8 mg, 0.19 mmol) in DMF (0.75 mL) was stirred overnight, diluted with EtOAc, washed with 1 N NaOH and brine, dried ($Na_2SO_4$), and filtered. The residue was chromatographed on $SiO_2$ (3% EtOAc/$CH_2Cl_2$) to give the title compound as a white solid (4.8 mg, 0.013 mmol). $^1$H NMR (300 MHz, DMSO-$d_6$) δ 11.95 (s, 1H), 8.44 (d, 1H), 8.23-7.90 (m, 3H), 7.26-7.00 (m, 3H), 3.80 (s, 2H); MS (DCI) M/Z 401.2 (M+$NH_4$)$^+$.

Example 12

2-(1-adamantyl)-N-[1-oxo-4-(trifluoromethyl)phthalazin-2(1H)-yl]acetamide

The product of Example 11B (50.6 mg) and (adamantan-1-yl)acetyl chloride (54 mg, 0.25 mmol) were treated as in Example 6 to give the title compound (69 mg, 0.17 mmol) as a white solid. $^1$H NMR (300 MHz, DMSO-$d_6$) δ 11.47 (s, 1H), 8.44 (dd, 1H), 8.18-7.98 (m, 3H), 2.08 (s, 2H), 1.99-1.92 (m, 3H), 1.75-1.55 (m, 12H); MS (DCI) M/Z 423.3 (M+$NH_4$)$^+$.

Example 13

2-(4-chlorophenyl)-N-[1-oxo-4-(trifluoromethyl)phthalazin-2(1H)-yl]acetamide

The product of Example 11B (41 mg) and 2-(4-chlorophenyl)acetyl chloride (0.030 mL, 0.20 mmol) were treated using a method similar to that described in Example 1C to give the title compound (57 mg, 0.15 mmol) as a white solid. $^1$H NMR (300 MHz, DMSO-$d_6$) δ 11.90 (s, 1H), 8.42 (dd, 1H), 8.19-7.97 (m, 3H), 7.41 (dd, J=3.3 Hz, 4H), 3.74 (s, 2H); MS (DCI) M/Z 399.2 (M+$NH_4$)$^+$.

Example 14

N-(5,8-difluoro-1-oxo-4-phenylphthalazin-2(1H)-yl)-2-(4-fluorophenyl)acetamide

Example 14A 5,8-difluoro-4-phenylphthalazin-2(1H)-one

A mixture of 4,7-difluoroisobenzofuran-1,3-dione (Alfa Aesar) (0.498 g, 2.70 mmol) and aluminum trichloride (1.08 g, 8.10 mmol) in benzene (8 mL) was heated to 90° C. overnight, concentrated, quenched with 1N HCl, diluted with EtOAc, washed with water and brine, dried ($Na_2SO_4$), filtered, and concentrated. The crude material was dissolved in EtOH (10 mL) and stirred with hydrazine hydrate (0.5 mL, 8.84 mmol) at 85° C. for 4 h, concentrated, and filtered. The residue was chromatographed on SiO$_2$ (3% MeOH/CH$_2$Cl$_2$) to give the title compound (0.326 g, 1.26 mmol) as a white solid. $^1$H NMR (300 MHz, DMSO-d$_6$) δ 12.91 (s, 1H), 7.79-7.64 (m, 2H), 7.45 (s, 5H).

Example 14B 2-amino-5,8-difluoro-4-phenylphthalazin-2(1H)-one

The product of Example 14A (0.326 g, 1.26 mmol) and O-(diphenylphosphoryl)hydroxylamine (0.295 mg, 1.27 mmol) were treated as in Example 9B to give the crude title compound (216 mg) as an orange solid. $^1$H NMR (300 MHz, DMSO-d$_6$) δ 7.77-7.63 (m, 2H), 7.53-7.40 (m, 5H), 6.52 (s, 2H).

Example 14C

N-(5,8-difluoro-1-oxo-4-phenylphthalazin-2(1H)-yl)-2-(4-fluorophenyl)acetamide

The product of Example 14B (38 mg) and 2-(4-fluorophenyl)acetic acid (26.4 mg, 0.17 mmol) were treated using a method similar to that described in Example 5 to give the title compound (17 mg, 0.042 mmol) as a white solid. $^1$H NMR (300 MHz, DMSO) δ 11.64 (s, 1H), 7.87-7.74 (m, 2H), 7.47 (s, 5H), 7.42-7.33 (m, 2H), 7.22-7.09 (m, 2H), 3.67 (s, 2H); MS (ESI$^-$) M/Z 408.6 (M−H)$^-$.

Example 15

2-(1-adamantyl)-N-(5,8-difluoro-1-oxo-4-phenylphthalazin-2(1H)-yl)acetamide

The product of Example 14B (47 mg) and (adamantan-1-yl)acetyl chloride (44 mg, 0.21 mmol) were treated using a method similar to that described in Example 6 to give the title compound (38.1 mg, 0.085 mmol) as a white solid. $^1$H NMR (300 MHz, DMSO-d$_6$) δ 11.21 (s, 1H), 7.87-7.74 (m, 2H), 7.47 (s, 5H), 2.04 (s, 2H), 1.94 (s, 3H), 1.67 (s, 12H); MS (ESI$^+$) M/Z 450.3 (M+H)$^+$.

Example 16

2-(4-chlorophenyl)-N-(5,8-difluoro-1-oxo-4-phenylphthalazin-2(1H)-yl)acetamide

The product of Example 14B (42.5 mg) and 2-(4-chlorophenyl)acetyl chloride (0.026 mL, 0.18 mmol) were treated method similar to that described in Example 1C to give the title compound (40.8 mg, 0.096 mmol) as a white solid. $^1$H NMR (300 MHz, DMSO-d$_6$) δ 11.65 (s, 1H), 7.86-7.75 (m, 2H), 7.46 (s, 5H), 7.38 (dd, 4H), 3.68 (s, 2H); MS (ESI$^-$) M/Z 424.6 (M−H)$^-$.

Example 17

2-(1-adamantyl)-N-(1-oxo-4-phenylphthalazin-2(1H)-yl)acetamide

Example 17A
O-(diphenylphosphoryl)hydroxylamine

To a stirred solution of hydroxylamine hydrochloride (9.5 g, 137 mmol) in H$_2$O (21 mL) was added aqueous sodium hydroxide (4.6 g, 116 mmol) in H$_2$O (16 mL), followed by dioxane (66 mL). The resulting solution was cooled in an ice/salt bath, and diphenylphosphinyl chloride (11.8 g, 50 mmol) in dioxane (50 mL) was added in one portion with vigorous stirring. Stirring was continued for 5 minutes as copious precipitation ensued. Water (200 mL) was added, and the slurry filtered, and was purified by stirring the slurry with aqueous sodium hydroxide (1 g, 25 mmol) in water (100 mL) at 0° C. for 30 min, followed by filtration and drying in vacuo to afford 6.8 g (59%) of the title compound. $^1$H NMR (300 MHz, DMSO-d$_6$) δ ppm 7.38-7.57 (m, 6H) 7.64-7.79 (m, 4H).

Example 17B 2-amino-4-phenylphthalazin-1(2H)-one

A mixture of 4-phenylphthalazin-1(2H)-one (Aldrich) (500 mg, 2.25 mmol) and KOtBu (3.37 mL, 3.37 mmol) was stirred for 45 minutes, diluted with DMF for solubility, and Example 17A (787 mg, 3.37 mmol) was added and stirred for 3 hours. The mixture was diluted with EtOAc, washed with saturated NaHCO$_3$ and brine, dried (Na$_2$SO$_4$), filtered, and concentrated to give 509 mg (95%) of the title compound. MS (DCI/NH$_3$) m/z 238 (M+H)$^+$.

Example 17C 2-(1-adamantyl)-N-(1-oxo-4-phenylphthalazin-2(1H)-yl)acetamide

The product from Example 17B (100 mg, 0.42 mmol), 2-(adamant-1-yl)acetic acid (82 mg, 0.42 mmol), 1-hydroxybenzotriazole hydrate (HOBT, 116 mg, 0.84 mmol), EDC (161 mg, 0.84 mmol), and DMAP (82 mg) were combined in pyridine (5 mL). The mixture was stirred at room temperature for 12 hours. The mixture was concentrated to dryness. The residue was dissolved in EtOAc and washed with NaHCO$_3$, dried (Na$_2$SO$_4$), and concentrated. The residue was purified by Intelliflash280™ (SiO$_2$, 90% hexanes/EtOAc to 50% hexanes/EtOAc) to afford 35 mg (20%) of the title compound. $^1$H NMR (500 MHz, DMSO-d$_6$) δ ppm 1.52-1.77 (m, 13H) 1.94 (s, 3H) 1.99-2.11 (m, 2H) 7.50-7.65 (m, 5H) 7.63-7.80 (m, 1H) 7.86-8.06 (m, 2H) 8.33-8.49 (m, 1H) 11.26 (s, 1H); MS (ESI) m/z 414 (M+H)$^+$.

Example 18

2-(3,5-difluorophenyl)-N-(1-oxo-4-phenylphthalazin-2(1H)-yl)acetamide

The product from Example 17B and 2-(3,5-difluorophenyl)acetic acid were processed using a method similar to that described in Example 17C to afford the title compound. $^1$H NMR (500 MHz, DMSO-d$_6$) δ ppm 3.76 (s, 2H) 7.12 (d, J=8.85 Hz, 3H) 7.50-7.64 (m, 5H) 7.66-7.80 (m, 1H) 7.86-8.10 (m, 2H) 8.30-8.56 (m, 1H) 11.80 (s, 1 H); MS (ESI) m/z 392 (M+H)$^+$.

Example 19

N-(4-chloro-1-oxophthalazin-2(1H)-yl)-2-(3,5-difluorophenyl)acetamide

Example 19A

2-amino-4-chlorophthalazin-1(2H)-one

4-Chlorophthalazin-1(2H)-one (Maybridge) was processed using a method similar to that described in Example 17B to afford the title compound. MS (ESI) m/z 196 (M+H)$^+$.

Example 19B

N-(4-chloro-1-oxophthalazin-2(1H)-yl)-2-(3,5-difluorophenyl)acetamide

The product from Example 19A and 2-(3,5-difluorophenyl)acetic acid were processed using a method similar to that described in Example 17C to afford the title compound. $^1$H NMR (500 MHz, DMSO-d$_6$) δ ppm 3.77 (s, 2H) 7.06-7.22 (m, 3H) 7.98-8.20 (m, 3H) 8.37 (d, J=7.32 Hz, 1H) 11.82 (s, 1H); MS (ESI) m/z 350 (M+H)$^+$.

Example 20

2-(1-adamantyl)-N-(4-chloro-1-oxophthalazin-2(1H)-yl)acetamide

The product from Example 19A and adamantyl acetic acid were processed using a method similar to that described in Example 17C to afford the title compound. $^1$H NMR (400 MHz, DMSO-d$_6$) δ ppm 1.54-1.76 (m, 12H) 1.96 (s, 3H) 2.05 (s, 2H) 7.92-8.20 (m, 3H) 8.37 (d, J=7.63 Hz, 1H) 11.20-11.50 (m, 1H); MS (ESI) m/z 372 (M+H)$^+$.

Example 21

N-(4-chloro-1-oxophthalazin-2(1H)-yl)-2-(4-chlorophenyl)acetamide

The product from Example 19A and 2-(4-chlorophenyl)acetic acid were processed using a method similar to that described in Example 17C to afford the title compound. $^1$H NMR (400 MHz, DMSO-d$_6$) δ ppm 3.70 (s, 2H) 7.23-7.56 (m, 4H) 7.97-8.17 (m, 3H) 8.36 (d, J=7.63 Hz, 1H) 11.77 (s, 1H); MS (ESI) m/z 349 (M+H)$^+$.

Example 22

2-(4-chlorophenyl)-N-(4-cyclopropyl-1-oxophthalazin-2(1H)-yl)acetamide

Example 22A

4-cyclopropylphthalazin-1(2H)-one

Cyclopropylmagnesium bromide was processed using a method similar to that described in Example 1A to afford the title compound. MS (ESI) m/z 187 (M+H)$^+$.

Example 22B

2-amino-4-cyclopropylphthalazin-1(2H)-one

The product from Example 22A was processed using a method similar to that described in Example 17B to afford the title compound. MS (ESI) m/z 202 (M+H)$^+$.

Example 22C

2-(4-chlorophenyl)-N-(4-cyclopropyl-1-oxophthalazin-2(1H)-yl)acetamide

The product from Example 22B and 2-(4-chlorophenyl)acetic acid were processed using a method similar to that described in Example 17C to afford the title compound. $^1$H NMR (500 MHz, DMSO-d$_6$) δ ppm 0.79-0.92 (m, 2H) 0.92-1.07 (m, 2H) 2.45-2.55 (m, 1H) 3.67 (s, 2H) 7.32-7.52 (m, 4H) 7.92 (t, J=8.09 Hz, 1H) 7.99-8.14 (m, 1H) 8.31 (t, J=7.32 Hz, 2H) 11.50 (s, 1H); MS (ESI) m/z 354 (M+H)$^+$.

Example 23

N-(4-cyclopropyl-1-oxophthalazin-2(1H)-yl)-2-(3,5-difluorophenyl)acetamide

The product from Example 22B and 2-(3,5-difluorophenyl)acetic acid were processed using a method similar to that described in Example 17C to afford the title compound. $^1$H NMR (500 MHz, DMSO-d$_6$) δ ppm 0.79-0.94 (m, 2H) 0.93-1.09 (m, 2H) 2.42-2.55 (m, 1H) 3.73 (s, 2H) 6.95-7.29 (m, 3H) 7.92 (t, J=7.63 Hz, 1H) 7.98-8.13 (m, 1H) 8.32 (d, J=7.93 Hz, 2H) 11.56 (s, 1H); MS (ESI) m/z 356 (M+H)$^+$.

Example 24

2-(1-adamantyl)-N-(4-cyclopropyl-1-oxophthalazin-2(1H)-yl)acetamide

The product from Example 22B was processed using a method similar to that described in Example 17C to afford the title compound. $^1$H NMR (500 MHz, DMSO-d$_6$) δ ppm 0.78-0.93 (m, 2H) 0.93-1.08 (m, 2H) 1.55-1.75 (m, 12H) 1.95 (s, 3H) 2.01 (s, 2H) 2.42-2.56 (m, 1H) 7.91 (t, J=7.48 Hz, 1H) 8.00-8.08 (m, 1H) 8.31 (dd, J=7.48, 4.73 Hz, 2 H) 11.05 (s, 1H); MS (ESI) m/z 378 (M+H)$^+$.

Example 25

2-(2,3-difluorophenyl)-N-(1-oxo-4-phenylphthalazin-2(1H)-yl)acetamide

The product from Example 17B and 2-(2,3-difluorophenyl)acetic acid were processed using a method similar to that described in Example 17C to afford the title compound. $^1$H NMR (500 MHz, DMSO-d$_6$) δ ppm 3.84 (s, 2H) 7.20 (d, J=6.10 Hz, 1H) 7.25-7.43 (m, 2 H) 7.53-7.66 (m, 5H) 7.66-7.83 (m, 1H) 7.88-8.06 (m, 2H) 8.19-8.67 (m, 1H) 11.78 (s, 1H); MS (ESI) m/z 392 (M+H)$^+$.

Example 26

2-(4-fluorophenyl)-N-(1-oxo-4-phenylphthalazin-2(1H)-yl)acetamide

The product from Example 17B and 2-(4-fluorophenyl) acetic acid were processed using a method similar to that described in Example 17C to afford the title compound. $^1$H NMR (500 MHz, DMSO-d$_6$) δ ppm 3.69 (s, 2H) 7.17 (t, J=8.85 Hz, 2H) 7.41 (dd, J=8.54, 5.49 Hz, 2H) 7.50-7.64 (m, 5H) 7.65-7.78 (m, 1H) 7.84-8.08 (m, 2H) 8.24-8.61 (m, 1H) 11.70 (s, 1H); MS (ESI) m/z 374 (M+H)$^+$.

Example 27

2-(2,5-difluorophenyl)-N-(1-oxo-4-phenylphthalazin-2(1H)-yl)acetamide

The product from Example 17B and 2-(2,5-difluorophenyl)acetic acid were processed using a method similar to that described in Example 17C to afford the title compound. $^1$H NMR (500 MHz, DMSO-d$_6$) δ ppm 3.78 (s, 2H) 7.15-7.22 (m, 1H) 7.22-7.30 (m, 1H) 7.30-7.46 (m, 1H) 7.54-7.65 (m, 5H) 7.66-7.80 (m, 1H) 7.87-8.11 (m, 2H) 8.33-8.53 (m, 1H) 11.77 (s, 1H); MS (ESI) m/z 392 (M+H)$^+$.

Example 28

2-(4-chlorophenyl)-N-(4-methyl-1-oxophthalazin-2(1H)-yl)acetamide

Example 28A 2-amino-4-methylphthalazin-1(2H)-one

4-Methylphthalazin-1(2H)-one (Enamine) was processed using a method similar to that described in Example 17B to afford the title compound. MS (ESI) m/z 196 (M+H)$^+$.

Example 28B 2-(4-chlorophenyl)-N-(4-methyl-1-oxophthalazin-2(1H)-yl)acetamide

The product from Example 28A and 2-(4-chlorophenyl)acetic acid were processed using a method similar to that described in Example 17C to afford the title compound. $^1$H NMR (500 MHz, DMSO-d$_6$) δ ppm 2.54 (s, 3H) 3.74 (s, 2H) 6.94-7.09 (m, 1H) 7.10-7.20 (m, 3H) 7.85-7.98 (m, 1H) 7.95-8.11 (m, 2H) 8.32 (d, J=7.93 Hz, 1H) 11.47-11.69 (m, 1H); MS (ESI) m/z 328 (M+H)$^+$.

Example 29

2-(1-adamantyl)-N-(7-oxo-4-phenylthieno[2,3-d]pyridazin-6(7H)-yl)acetamide

Example 29A 4-phenylthieno[2,3-d]pyridazin-7(6H)-one

A solution of 3-benzoylthiophene-2-carboxylic acid (0.497 g, 2.14 mmol) (Alfa Aesar) and hydrazine hydrate (0.50 mL, 8.8 mmol) in EtOH (6 mL) was stirred at 85° C. for 4 hours, concentrated, and azeotroped with toluene to give the title compound (0.50 g, 2.2 mmol) as a tan solid. $^1$H NMR (300 MHz, DMSO-d$_6$) δ 8.28 (d, 1H), 7.69-7.75 (m, 2H), 7.51-7.59 (m, 4H).

Example 29B 6-amino-4-phenylthieno[2,3-d]pyridazin-7(6H)-one

The product of Example 29A was processed using a method similar to that described in Example 17B to afford the title compound. MS (ESI) m/z 244 (M+H)$^+$.

Example 29C 2-(1-adamantyl)-N-(7-oxo-4-phenylthieno[2,3-d]pyridazin-6(7H)-yl)acetamide The product from Example 29B and 2-(adamant-1-yl)acetic acid was processed using a method similar to that described in Example 17C to afford the title compound. $^1$H NMR (500 MHz, DMSO-d$_6$) δ ppm 1.52-1.81 (m, 12H) 1.95 (s, 3H) 2.07 (s, 2H) 7.46-7.64 (m, 4H) 7.71 (dd, J=7.48, 1.98 Hz, 2H) 8.35 (d, J=5.49 Hz, 1H) 11.36 (s, 1H); MS (ESI) m/z 420 (M+H)$^+$.

Example 30

2-[(1S,2S,5S)-6,6-dimethylbicyclo[3.1.1]hept-2-yl]-N-(7-oxo-4-phenylthieno[2,3-d]pyridazin-6(7H)-yl)acetamide The product from Example 29B and 2-[(1S,2S,5S)-6,6-dimethylbicyclo[3.1.1]hept-2-yl]acetic acid (Eigenmann, G. W.; Arnold, R. T. JACS 1959, 81, 3440-2) were processed using a method similar to that described in Example 17C to afford the title compound. $^1$H NMR (500 MHz, DMSO-d$_6$) δ ppm 0.91 (d, J=9.76 Hz, 1H) 1.08 (s, 3H) 1.20 (s, 3H) 1.39-1.66 (m, 1H) 1.76-2.05 (m, 5H) 2.20-2.46 (m, 4H) 7.45-7.65 (m, 4H) 7.71 (dd, J=7.63, 1.83 Hz, 2H) 8.35 (d, J=5.19 Hz, 1H) 11.46 (s, 1H); MS (ESI) m/z 408 (M+H)$^+$.

Example 31

2-(4-chlorophenyl)-N-(7-oxo-4-phenylthieno[2,3-d]pyridazin-6(7H)-yl)acetamide

The product from Example 29B and 2-(4-chlorophenyl)acetic acid were processed using a method similar to that described in Example 17C to afford the title compound. $^1$H NMR (500 MHz, DMSO-d$_6$) δ ppm 3.72 (s, 2H) 7.41 (s, 4H) 7.56 (dd, J=4.42, 2.59 Hz, 4H) 7.63-7.80 (m, 2H) 8.36 (d, J=5.19 Hz, 1H) 11.81 (s, 1H); MS (ESI) m/z 396 (M+H)$^+$.

Example 32

2-(4-fluorophenyl)-N-(7-oxo-4-phenylthieno[2,3-d]pyridazin-6(7H)-yl)acetamide

The product from Example 29B and 2-(4-fluorophenyl)acetic acid were processed using a method similar to that described in Example 17C to afford the title compound. $^1$H NMR (500 MHz, DMSO-d$_6$) δ ppm 3.71 (s, 2H) 7.18 (t, J=8.85 Hz, 2H) 7.41 (dd, J=8.54, 5.80 Hz, 2H) 7.48-7.65 (m, 4H) 7.63-7.78 (m, 2H) 8.36 (d, J=5.19 Hz, 1H) 11.80 (s, 1 H); MS (ESI) m/z 380 (M+H)$^+$.

Example 33

2-(3,5-difluorophenyl)-N-(7-oxo-4-phenylthieno[2,3-d]pyridazin-6(7H)-yl)acetamide The product from Example 29B and 2-(3,5-difluorophenyl)acetic acid were processed using a method similar to that described in Example 17C to afford the title compound. $^1$H NMR (500 MHz, DMSO-d$_6$) δ ppm 3.79 (s, 2H) 6.94-7.36 (m, 3H) 7.51-7.64 (m, 4H) 7.61-7.84 (m, 2H) 8.37 (d, J=5.19 Hz, 1H) 11.87 (s, 1H); MS (ESI) m/z 398 (M+H)$^+$.

Example 34

2-[3,5-dimethyl-1-adamantyl]-N-(4-isopropyl-1-oxophthalazin-2(1H)-yl)acetamide

The product from Example 1B and 2-(3,5-dimethyl-1-adamantyl)acetic acid were processed using the method described in Example 17C to afford the title compound. $^1$H NMR (500 MHz, DMSO-d$_6$) δ ppm 0.81 (s, 6H) 0.98-1.20 (m, 2H) 1.20-1.42 (m, 14H) 1.52 (s, 2H) 1.98-2.14 (m, 3H) 3.49-3.73 (m, 1H) 7.89 (t, J=7.48 Hz, 1H) 7.95-8.04 (m, 1H) 8.11 (d, J=8.24 Hz, 1H) 8.34 (d, J=6.71 Hz, 1H) 11.12 (s, 1H); MS (ESI) m/z 408 (M+H)$^+$.

Example 35

2-(3,5-difluorophenyl)-N-(6-fluoro-1-oxo-4-phenylphthalazin-2(1H)-yl)acetamide

Example 35A
(2-bromo-5-fluorophenyl)(phenyl)methanol

A solution of PhMgBr (1M in THF, 2.60 mL, 2.60 mmol) was added dropwise to a −78° C. solution of 2-bromo-5-fluorobenzaldehyde (0.4742 g, 2.336 mmol) in Et$_2$O (5 mL) and THF (1.3 mL), stirred for 15 minutes, allowed to warm to room temperature, stirred for 30 minutes, diluted with EtOAc, washed with water and saturated NH$_4$Cl, dried (Na$_2$SO$_4$), and filtered. The residue was chromatographed on SiO$_2$ (0-10% Et$_2$O/hexanes) to give 561.0 mg of the title compound as a clear gum. $^1$H NMR (300 MHz, DMSO-d$_6$) δ 7.60 (dd, 1H), 7.46 (dd, 1H), 7.21-7.36 (m, 5H), 7.10 (ddd, 1H), 6.21 (s, 1H), 5.88 (s, 1H).

Example 35B
(2-bromo-5-fluorophenyl)(phenyl)methanone

A mixture of Dess-Martin periodinane (0.931 g, 2.20 mmol) and the product of example 35A (0.561 g, 2.00 mmol) was stirred in CH$_2$Cl$_2$ (10 mL) for 1 hour, diluted with EtOAc, washed with saturated aqueous NaHCO$_3$ and brine, dried (Na$_2$SO$_4$), filtered, and concentrated. The residue was chromatographed on SiO$_2$ (eluted with 4% Et$_2$O/hexanes) to give 515.6 mg of the title compound as a clear gum. $^1$H NMR (300 MHz, DMSO) δ 7.81 (dd, 1H), 7.69-7.76 (m, 3H), 7.54-7.61 (m, 2H), 7.50 (dd, 1H), 7.39 (ddd, 1H).

Example 35C methyl 2-benzoyl-4-fluorobenzoate

A mixture of the product of example 35B (0.516 g, 1.85 mmol), PdCl$_2$dppf.CHCl$_3$ (75 mg, 0.091 mmol), and triethylamine (0.39 mL, 2.8 mmol) was stirred in 1:1 DMF:MeOH (6 mL, pre-saturated with CO) under CO (1 atm) at 80° C. for 4 hours, diluted with EtOAc, washed with water and brine, dried (Na$_2$SO$_4$), and filtered. The residue was chromatographed on SiO$_2$ (3-12% Et$_2$O/hexanes) to give 112.0 mg of the title compound as a clear gum. $^1$H NMR (300 MHz, DMSO) δ 8.09 (dd, 1H), 7.62-7.69 (m, 3H), 7.49-7.57 (m, 3H), 7.45 (dd, 1H), 3.57 (s, 3H).

Example 35D 6-fluoro-4-phenylphthalazin-1(2H)-one

A solution of hydrazine hydrate (0.26 mL, 4.6 mmol) and the product of example 35C (0.390 g, 1.5 mmol) in EtOH (4.5 mL) was stirred at 80° C. for 3 hours, concentrated, and chromatographed on SiO$_2$ (3% MeOH/CH$_2$Cl$_2$) to give 293.5 mg of the title compound as a white solid. $^1$H NMR (300 MHz, DMSO-d$_6$) δ 12.93 (s, 1H), 8.42 (dd, 1H), 7.76 (ddd, 1H), 7.53-7.63 (m, 5H), 7.32 (dd, 1H).

Example 35E 2-amino-6-fluoro-4-phenylphthalazin-1(2H)-one

The product of example 35D was processed using a method similar to that described in Example 17B to afford the title compound. MS (ESI) m/z 256 (M+H)$^+$.

Example 35F 2-(3,5-difluorophenyl)-N-(6-fluoro-1-oxo-4-phenylphthalazin-2(1H)-yl)acetamide The product from Example 35E and 2-(3,5-difluorophenyl)acetic acid were processed using a method similar to that described in Example 17C to afford the title compound. $^1$H NMR (500 MHz, DMSO-d$_6$) δ ppm 3.75 (s, 2H) 7.03-7.20 (m, 3H) 7.38 (dd, J=9.46, 2.44 Hz, 1H) 7.52-7.68 (m, 5H) 7.82 (d, J=2.44 Hz, 1H) 8.48 (d, J=3.36 Hz, 1H); MS (ESI) m/z 410 (M+H)$^+$.

Example 36

2-(4-chlorophenyl)-N-(6-fluoro-1-oxo-4-phenylphthalazin-2(1H)-yl)acetamide

The product from Example 35E and 4-chlorophenylacetic acid were processed using a method similar to that described in Example 17C to afford the title compound. $^1$H NMR (500 MHz, DMSO-d$_6$) δ ppm 3.70 (s, 2H) 7.28-7.52 (m, 5H) 7.50-7.70 (m, 5H) 7.72-7.99 (m, 1H) 8.47 (dd, J=8.85, 5.49 Hz, 1H) 11.62-11.89 (m, 1H); MS (ESI) m/z 408 (M+H)$^+$.

Example 37

2-(1-adamantyl)-N-(6-fluoro-1-oxo-4-phenylphthalazin-2(1H)-yl)acetamide

The product from Example 35E and 2-(adamant-1-yl)acetic acid were processed using a method similar to that described in Example 17C to afford the title compound. $^1$H NMR (500 MHz, DMSO-d$_6$) δ ppm 1.49-1.76 (m, 12H) 1.86-1.99 (m, 3H) 2.06 (s, 2H) 7.39 (dd, J=9.46, 2.44 Hz, 1H) 7.52-7.67 (m, 5H) 7.71-7.94 (m, 1H) 8.49 (dd, J=8.85, 5.49 Hz, 1H) 11.29 (s, 1H); MS (ESI) m/z 432 (M+H)$^+$.

Example 38

2-(3,5-difluorophenyl)-N-(4-methyl-1-oxophthalazin-2(1H)-yl)acetamide

The product from Example 28A and 2-(3,5-difluorophenyl)acetic acid were processed using a method similar to that described in Example 17C to afford the title compound. $^1$H NMR (500 MHz, DMSO-d$_6$) δ ppm 11.58-11.61 (m, 1H), 8.32 (d, J=7.9 Hz, 1H), 8.00-8.02 (m, 2H), 7.90-7.93 (m, 1H), 7.09-7.21 (m, 2H), 7.02-7.05 (m, 1H), 3.74 (s, 2H), 2.55 (s, 3H); MS (ESI) m/z 330 (M+H)$^+$.

Example 39

2-[1-(4-chlorophenyl)cyclopropyl]-N-[1-oxo-4-(trifluoromethyl)phthalazin-2(1H)-yl]acetamide A solution of 1-(4-chlorophenyl)cyclopropanecarboxylic acid (0.3502 g, 1.781 mmol) and oxalyl dichloride (0.20 mL, 2.293 mmol) in dichloromethane (6 mL) containing a catalytic amount of DMF was stirred for 2 hours, concentrated, and re-dissolved in acetonitrile (5 mL) and THF (5 mL), and cooled to 0° C. A solution of (diazomethyl)trimethylsilane in Et$_2$O (2M, 1.78 mL, 3.56 mmol) was added, stirred for 4 hours, allowing to warm to room temperature, concentrated, diluted with EtOAc, washed with saturated aqueous NaHCO$_3$ and brine, dried (Na$_2$SO$_4$), filtered, and concentrated to give 355 mg of crude product as a dark oil, which was used without purification.

A solution of the above crude 1-(1-(4-chlorophenyl)cyclopropyl)-2-diazoethanone (0.050 g, 0.23 mmol), the product from Example 11B (0.0505 g, 0.22 mmol), triethylamine (0.12 mL, 0.86 mmol), and silver benzoate (0.0504 g, 0.220 mmol) in DMF (1 mL) were stirred for 2 hours at 70° C., diluted with EtOAc, washed with saturated aqueous NaHCO$_3$ and brine, dried (Na$_2$SO$_4$), and filtered. The residue was chromatographed on SiO$_2$ (30% EtOAc/hexanes) to give the title compound (23.0 mg, 0.055 mmol) as a white solid: $^1$H NMR (300 MHz, DMSO-d$_6$) δ ppm 11.56 (s, 1H), 8.41-8.44 (m, 1H), 7.95-8.20 (m, 3H), 7.22-7.42 (m, 4H), 2.72 (d, J=1.0 Hz, 2H), 1.04-1.10 (m, 2H), 0.84-0.90 (m, 2H); MS (ESI$^+$) M/Z 422 (M+H)$^+$, 439 (M+NH$_4$)$^+$.

Example 40

2-[1-(4-chlorophenyl)cyclobutyl]-N-[1-oxo-4-(trifluoromethyl)phthalazin-2(1H)-yl]acetamide A solution of 1-(4-chlorophenyl)cyclobutanecarboxylic acid (1.0068 g, 4.78 mmol) and oxalyl chloride in dichloromethane (15 mL) containing a catalytic amount of DMF was stirred for 2 hours, concentrated, re-dissolved in 1:1 acetonitrile:THF, and cooled to 0° C. A solution of (diazomethyl)trimethylsilane in Et$_2$O (2M, 4.8 mL, 9.6 mmol) was added, and the mix was stirred for 4 hours, allowing to warm to room temperature, concentrated, washed with saturated aqueous NaHCO$_3$ and brine, dried (Na$_2$SO$_4$), filtered, and concentrated to give 1.12 g of crude product which was used without purification.

A solution of the above crude 1-(1-(4-chlorophenyl)cyclobutyl)-2-diazoethanone (65.6 mg, 0.280 mmol), the product from Example 11B (0.0503 g, 0.219 mmol), triethylamine (0.12 mL, 0.86 mmol), and silver benzoate (12.4 mg, 0.054 mmol) in DMF (1 mL) was stirred for 2 hours, diluted with EtOAc, washed with saturated aqueous NaHCO$_3$ and brine, dried (Na$_2$SO$_4$), and filtered. The residue was chromatographed on SiO$_2$ (4% EtOAc/dichloromethane) to give the title compound (33.5 mg) as a white solid. $^1$H NMR (300 MHz, DMSO-d$_6$) δ ppm 11.50 (s, 1H), 8.41 (dd, J=7.9, 1.4 Hz, 1H), 8.09-8.15 (m, 1H), 8.02-8.07 (m, 1H), 7.97-8.02 (m, 1H), 7.30-7.34 (m, 2H), 7.21-7.24 (m, 2H), 2.80 (s, 2H), 2.44-2.49 (m, 2H), 2.26-2.39 (m, 2H), 2.06-2.21 (m, 1H), 1.70-1.84 (m, 1H); MS (ESI$^+$) M/Z 436 (M+H)$^+$.

Example 41

2-(2-naphthyl)-N-[1-oxo-4-(trifluoromethyl)phthalazin-2(1H)-yl]acetamide

The product of Example 11B and 2-napthylacetic acid were treated using a method similar to that described in Example 57 to give the title compound. $^1$H NMR (500 MHz, DMSO-d$_6$/Deuterium Oxide) δ ppm 8.44 (ddd, J=8.0, 1.4, 0.6 Hz, 1H), 8.12-8.16 (m, 1H), 8.01-8.09 (m, 2H), 7.87-7.97 (m, 4H), 7.48-7.59 (m, 3H), 3.91 (s, 2H); MS (ESI$^-$) M/Z 396 (M–H)$^-$.

Example 42

3-(4-chlorophenyl)-3-methyl-N-[1-oxo-4-(trifluoromethyl)phthalazin-2(1H)-yl]butanamide The product of Example 11B and 2-(4-chlorophenyl)-2-methylpropanoic acid were treated using a method similar to that described in Example 39 to give the title compound. $^1$H NMR (300 MHz, DMSO-d$_6$) δ ppm 11.57 (s, 1H), 8.42 (dd, J=7.9, 1.4 Hz, 1H), 8.10-8.16 (m, 1H), 8.03-8.07 (m, 1H), 7.98-8.03 (m, 1H), 7.44-7.47 (m, 2H), 7.33-7.36 (m, 2H), 2.66 (s, 2H), 1.45 (s, 6H); MS (ESI$^+$) M/Z 424 (M+H)$^+$, 441 (M+NH$_4$)$^+$.

Example 43

2-cyclopentyl-N-[1-oxo-4-(trifluoromethyl)phthalazin-2(1H)-yl]acetamide

The product of Example 11B and 2-cyclopentylacetic acid were processed using a method similar to that described in Example 17C to afford the title compound. $^1$H NMR (400 MHz, DMSO-d$_6$) δ ppm 11.56-11.57 (m, 1H), 8.43 (d, J=8.5 Hz, 1H), 8.11-8.17 (m, 1H), 8.04-8.08 (m, 1H), 8.00-8.05 (m, 1H), 2.34 (d, J=7.4 Hz, 2H), 2.16-2.28 (m, 1H), 1.77-1.86 (m, 2H), 1.57-1.66 (m, 2H), 1.48-1.57 (m, 2H), 1.21-1.32 (m, 2H); MS (ESI) m/z 340 (M+H)$^+$.

Example 44

2,2-difluoro-N-[1-oxo-4-(trifluoromethyl)phthalazin-2(1H)-yl]-2-phenylacetamide

The product of Example 11B and 2,2-difluoro-2-phenylacetic acid were treated using a method similar to that described in Example 51 to give the title compound. $^1$H NMR (300 MHz, DMSO-d$_6$) δ ppm 13.10 (s, 1H), 8.43-8.47 (m, 1H), 8.16 (td, J=7.6, 1.6 Hz, 1H), 8.03-8.12 (m, 2H), 7.74-7.78 (m, 2H), 7.54-7.66 (m, 3H); MS (ESI$^+$) M/Z 384 (M+H)$^+$.

Example 45

2-cyclobutyl-N-[1-oxo-4-(trifluoromethyl)phthalazin-2(1H)-yl]acetamide

The product of Example 11B and 2-cyclobutylacetic acid were processed using a method similar to that described in Example 17C to afford the title compound. $^1$H NMR (400 MHz, DMSO) δ 11.61-11.40 (m, 1H), 8.46-8.38 (m, 1H), 8.17-8.09 (m, 1H), 8.09-7.98 (m, 2H), 2.73-2.61 (m, 1H), 2.46 (d, J=7.5, 2H), 2.15-2.01 (m, 2H), 1.93-1.70 (m, 4H); MS (ESI) m/z 326 (M+H)$^+$.

Example 46

N-[1-oxo-4-(trifluoromethyl)phthalazin-2(1H)-yl]-2-[4-(trifluoromethyl)phenyl]acetamide The product from Example 11B and 2-[4-(trifluoromethyl)phenyl]acetic acid were treated using a method similar to that described in Example 57 to give the title compound. $^1$H NMR (500 MHz, DMSO-$d_6$/Deuterium Oxide) δ ppm 8.44 (d, J=7.1 Hz, 1H), 8.14 (td, J=7.7, 1.4 Hz, 1H), 8.01-8.10 (m, 2H), 7.70-7.76 (m, 2H), 7.60-7.63 (m, 2H), 3.86-3.87 (bs, 2H); MS (ESI) m/z 416 (M+H)$^+$.

Example 47

2-[4-(dimethylamino)phenyl]-N-[1-oxo-4-(trifluoromethyl)phthalazin-2(1H)-yl]acetamide The product from Example 11B and 2-[4-(dimethylamino)phenyl]acetic acid were treated using a method similar to that described in Example 57 to give the title compound. $^1$H NMR (500 MHz, DMSO-$d_6$/Deuterium Oxide) δ ppm 8.43 (dd, J=7.9, 1.3 Hz, 1H), 8.13-8.17 (m, 1H), 8.04-8.08 (m, 2H), 7.38-7.40 (m, 2H), 7.19-7.21 (m, 2H), 3.70 (s, 2H), 3.05 (s, 6H); MS (ESI$^-$) M/Z 389 (M–H)$^-$.

Example 48

3,3-dimethyl-N-[1-oxo-4-(trifluoromethyl)phthalazin-2(1H)-yl]butanamide

The product from Example 11B and 3,3-dimethylbutanoic acid were treated using a method similar to that described in Example 57 to give the title compound. $^1$H NMR (500 MHz, DMSO-$d_6$/Deuterium Oxide) δ ppm 8.43-8.46 (m, 1H), 8.13-8.16 (m, 1H), 8.03-8.09 (m, 2H), 2.23 (s, 2H), 1.07 (s, 9H); MS (ESI$^-$) M/Z 326 (M–H)$^-$.

Example 49

2-[4-(methylsulfonyl)phenyl]-N-[1-oxo-4-(trifluoromethyl)phthalazin-2(1H)-yl]acetamide The product from Example 11B and 2-[4-(methylsulfonyl)phenyl]acetic acid were treated as in Example 57 to give the title compound. $^1$H NMR (500 MHz, DMSO-$d_6$/Deuterium Oxide) δ ppm 8.40-8.45 (m, 1H), 8.13-8.17 (m, 1H), 8.02-8.09 (m, 2H), 7.92-7.94 (m, 2H), 7.65-7.68 (m, 2H), 3.90 (s, 2H), 3.21 (s, 3H); MS (ESI$^-$) M/Z 424 (M–H)$^-$.

Example 50

N-[1-oxo-4-(trifluoromethyl)phthalazin-2(1H)-yl]-3-phenylpropanamide

The product from Example 11B and 3-phenylpropanoic acid were treated using a method similar to that described in Example 57 to give the title compound. $^1$H NMR (500 MHz, DMSO-$d_6$/Deuterium Oxide) δ ppm 8.40-8.46 (m, 1H), 8.15 (td, J=7.7, 1.4 Hz, 1H), 7.99-8.09 (m, 2H), 7.28-7.34 (m, 4H), 7.20-7.25 (m, 1H), 2.94 (t, J=7.7 Hz, 2H), 2.68 (t, J=7.7 Hz, 2H); MS (ESI$^-$) M/Z 360 (M–H)$^-$.

Example 51

N-[1-oxo-4-(trifluoromethyl)phthalazin-2(1H)-yl]-2-(1-phenylcyclopropyl)acetamide A solution of 2-(1-phenylcyclopropyl)acetic acid (0.063 g, 0.36 mmol) and oxalyl dichloride (0.042 mL, 0.48 mmol) in dichloromethane (1 mL) with a catalytic amount of DMF was stirred for 90 minutes, and concentrated. The material was re-dissolved in dichloromethane (1 mL) and the product from Example 11B (0.080 g, 0.35 mmol) was added, stirred for 2 hours, and concentrated. The residue was chromatographed on SiO$_2$ (0-2% diethyl ether/dichloromethane) to give the title compound (52 mg) as a white solid: $^1$H NMR (300 MHz, DMSO-$d_6$) δ ppm 11.56 (s, 1H), 8.41-8.45 (m, 1H), 8.10-8.16 (m, 1H), 7.97-8.07 (m, 2H), 7.32-7.40 (m, 2H), 7.23-7.29 (m, 2H), 7.13-7.20 (m, 1H), 2.74 (s, 2H), 1.04-1.10 (m, 2H), 0.84-0.89 (m, 2H); MS (ESI$^-$) M/Z 386 (M–H)$^-$.

Example 52

3-methyl-N-[1-oxo-4-(trifluoromethyl)phthalazin-2(1H)-yl]-3-phenylbutanamide

The product of Example 11B and 3-methyl-3-phenylbutanoic acid were processed using a method similar to that described in Example 17C to afford the title compound. $^1$H NMR (400 MHz, DMSO-$d_6$) δ ppm 11.58-11.60 (bs, 1H), 8.43 (dd, J=7.9, 1.3 Hz, 1H), 8.11-8.15 (m, 1H), 7.97-8.07 (m, 2H), 7.43-7.46 (m, 2H), 7.28-7.36 (m, 2H), 7.16-7.21 (m, 1H), 2.66 (s, 2H), 1.46 (s, 6H); MS (ESI) m/z 390 (M+H)$^+$.

Example 53

N-[1-oxo-4-(trifluoromethyl)phthalazin-2(1H)-yl]-2-(3-thienyl)acetamide

A mixture of the product of Example 11B (30.2 mg, 0.13 mmol), pyridine (0.14 mL, 0.17 mmol), and 2-(thiophen-3-yl)acetyl chloride (24.0 mg, 0.15 mmol) in dichloromethane (0.4 mL) was stirred for 3 hours, concentrated, and chromatographed (20% acetone/hexanes) to give the title compound (33.8 mg) as a white solid. $^1$H NMR (300 MHz, DMSO-$d_6$) δ ppm 11.82-11.94 (m, 1H), 8.44 (dd, J=7.9, 1.5 Hz, 1H), 8.11-8.17 (m, 1H), 8.00-8.09 (m, 2H), 7.36-7.58 (m, 2H), 7.14 (dd, J=4.9, 1.3 Hz, 1H), 3.74 (s, 2H); MS (ESI$^-$) M/Z 352 (M–H)$^-$.

Example 54

N-[1-oxo-4-(trifluoromethyl)phthalazin-2(1H)-yl]-2-(2-thienyl)acetamide

The product of Example 11B and 2-(thiophen-2-yl)acetyl chloride were treated using a method similar to that described in Example 53 to give the title compound. $^1$H NMR (300 MHz, DMSO-$d_6$) δ ppm 11.88-11.97 (m, 1H), 8.41-8.48 (m, 1H), 8.13 (td, J=7.7, 1.6 Hz, 1H), 8.00-8.09 (m, 2H), 7.43 (dd, J=5.1, 1.3 Hz, 1H), 7.04-7.08 (m, 1H), 7.01 (dd, J=5.1, 3.5 Hz, 1H), 3.96 (d, J=0.9 Hz, 2H); MS (ESI$^-$) M/Z 352 (M–H)$^-$.

Example 55

2-(5-chloro-2-thienyl)-N-[1-oxo-4-(trifluoromethyl)phthalazin-2(1H)-yl]acetamide The product of Example 11B and 2-(5-chlorothiophen-2-yl)acetic acid were treated using a method similar to that described in Example 5 to give the title compound. $^1$H NMR (300 MHz, DMSO-$d_6$) δ ppm 11.96-11.98 (bs, 1H), 8.43 (d, J=8.4 Hz, 1H), 8.11-8.17 (m, 1H), 7.97-8.10 (m, 2H), 7.01 (d, J=3.8 Hz, 1H), 6.93 (d, J=3.8 Hz, 1H), 3.96 (d, J=0.8 Hz, 2H); MS (ESI) m/z 388 (M+H)$^+$.

Example 56

2-(5-methyl-2-thienyl)-N-[1-oxo-4-(trifluoromethyl)phthalazin-2(1H)-yl]acetamide The product of Example 11B and 2-(5-methylthiophen-2-yl)acetic acid were treated using a method similar to that described in Example 5 to give the title compound. $^1$H NMR (300 MHz, DMSO-$d_6$) δ ppm 11.85-11.96 (m, 1H), 8.43 (d, J=6.9 Hz, 1H), 8.10-8.17 (m, 1H), 8.01-8.08 (m, 2H), 6.81 (d, J=3.4 Hz, 1H), 6.66-6.68 (m, 1H), 3.84-3.85 (bs, 2H), 2.41 (d, J=0.8 Hz, 3H); MS (ESI$^+$) M/Z 368 (M+H)$^+$, 385 (M+NH$_4$)$^+$.

Example 57

N-[1-oxo-4-(trifluoromethyl)phthalazin-2(1H)-yl]-2-phenylacetamide

To a 4 mL vial was added the product from Example 11B (20 mg in DMA), phenylacetic acid [1.5 equivalents in dimethyl acetamide, O-(7-azabenzotriazol-1-yl)-N,N,N',N'-tetramethyluronium hexafluorophosphate (HATU, 2 equivalents in dimethyl acetamide) and triethylamine (3 equivalents, neat). The vial was capped and microwaved at 150° C. for 30 minutes. The reaction was checked by LC/MS and concentrated to dryness upon completion. The residue was dissolved in 1:1 MeOH:DMSO and purified by reverse phase HPLC [Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min [0-0.5 min 10% A, 0.5-7.0 min linear gradient 10-95% A, 7.0-10.0 min 95% A, 10.0-12.0 min linear gradient 95-10% A]. $^1$H NMR (500 MHz, DMSO-$d_6$) δ ppm 11.89-11.91 (bs, 1H), 8.43 (dd, J=8.0, 1.3 Hz, 1H), 8.12-8.15 (m, 1H), 7.96-8.08 (m, 2H), 7.32-7.42 (m, 4H), 7.26-7.30 (m, 1H), 3.73 (s, 2H); MS (ESI$^+$) M/Z 348 (M+H)$^+$, 365 (M+NH$_4$)$^+$.

Example 58

(±)-2-(exo-bicyclo[2.2.1]heptan-2-yl)-N-[1-oxo-4-(trifluoromethyl)phthalazin-2(1H)-yl]acetamide

Example 58A

(±)-2-(exo-bicyclo[2.2.1]heptan-2-yl)acetyl chloride

A mixture of (±)-2-(exo-bicyclo[2.2.1]heptan-2-yl)acetic acid (0.294 g, 1.9 mmol) and oxalyl chloride (0.22 mL, 2.5 mmol) in dichloromethane (6 mL) with a catalytic amount of DMF was stirred for 90 minutes, concentrated, and used without purification.

Example 58B

(±)-2-(exo-bicyclo[2.2.1]heptan-2-yl)-N-[1-oxo-4-(trifluoromethyl)phthalazin-2(1H)-yl]acetamide The products from Example 11B and Example 58A were treated using a method similar to that described in Example 53 to give the title compound. $^1$H NMR (300 MHz, DMSO-$d_6$) δ ppm 11.54-11.56 (bs, 1H), 8.43 (d, J=8.4 Hz, 1H), 8.10-8.17 (m, 1H), 7.98-8.08 (m, 2H), 2.29 (dd, J=14.3, 8.3 Hz, 1H), 2.14-2.21 (m, 2H), 2.08-2.12 (m, 1H), 1.84-1.94 (m, 1H), 1.43-1.55 (m, 3H), 1.36-1.41 (m, 1H), 1.05-1.26 (m, 4H); MS (ESI$^-$) M/Z 364 (M−H)$^-$.

Example 59

2-(4-chloro-3-fluorophenyl)-N-[1-oxo-4-(trifluoromethyl)phthalazin-2(1H)-yl]acetamide The product of Example 11B and 2-(4-chloro-3-fluorophenyl)acetyl chloride were treated using a method similar to that described in Example 1C to give the title compound. $^1$H NMR (300 MHz, DMSO-$d_6$) δ ppm 11.92-11.95 (bs, 1H), 8.43 (d, J=8.3 Hz, 1H), 8.11-8.17 (m, 1H), 7.99-8.08 (m, 2H), 7.58 (t, J=8.1 Hz, 1H), 7.43 (dd, J=10.5, 1.9 Hz, 1H), 7.25 (dd, J=8.3, 1.9 Hz, 1H), 3.79 (s, 2H); MS (ESI) m/z 400 (M+H)$^+$.

Example 60

2-(3-fluoroadamantan-1-yl)-N-(4-isopropyl-1-oxophthalazin-2(1H)-yl)acetamide The product of Example 61 (44 mg, 0.11 mmol) in CH$_2$Cl$_2$ (5 mL) was treated with (diethylamino)sulfur trifluoride (26 µL, 0.17 mmol) at 0 C. The reaction mixture was allowed to warm to room temperature for 1 hour, quenched with aqueous saturated NaHCO$_3$, diluted with EtOAc, washed with water and brine, dried (Na$_2$SO$_4$), filtered, and concentrated. The residue was purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to give the title compound (22 mg, 50%): $^1$H NMR (500 MHz, DMSO-$d_6$) δ ppm 11.20 (s, 1H), 8.35 (dd, J=7.9, 1.3 Hz, 1H), 8.12 (d, J=8.1 Hz, 1H), 7.98-8.02 (m, 1H), 7.88-7.91 (m, 1H), 3.61 (p, J=6.7 Hz, 1H), 2.24-2.27 (m, 2H), 2.16-2.16 (bs, 2H), 1.75-1.85 (m, 6H), 1.45-1.65 (m, 6H), 1.26 (d, J=6.7 Hz, 6H); MS (ESI) m/z 398 (M+H)$^+$.

Example 61

2-(3-hydroxyadamantan-1-yl)-N-(4-isopropyl-1-oxophthalazin-2(1H)-yl)acetamide The product of Example 1B and 2-(3-hydroxyadamantan-1-yl)acetic acid were processed using a method similar to that described in Example 17C to afford the title compound. $^1$H NMR (500 MHz, DMSO-$d_6$) δ ppm 11.12 (s, 1H), 8.34 (dd, J=7.9, 1.3 Hz, 1H), 8.11 (d, J=8.1 Hz, 1H), 8.00 (ddd, J=8.3, 7.1, 1.3 Hz, 1H), 7.89 (ddd, J=8.0, 7.1, 1.0 Hz, 1H), 3.61 (p, J=6.7 Hz, 1H), 2.08-2.11 (m, 4H), 1.36-1.63 (m, 13H), 1.26 (d, J=6.7 Hz, 6H); MS (ESI) m/z 396 (M+H)$^+$.

Example 62

N-(4-tert-butyl-1-oxophthalazin-2(1H)-yl)-2-cyclopentylacetamide

Example 62A

2-amino-4-tert-butylphthalazin-1(2H)-one

Ethyl 2-pivaloylbenzoate was treated using procedures similar to those described in Examples 11A and Example 11B to give the title compound. MS (APCI$^+$) M/Z 218 (M+H)$^+$.

Example 62B

N-(4-tert-butyl-1-oxophthalazin-2(1H)-yl)-2-cyclopentylacetamide

The product from Example 62A and 2-cyclopentylacetic acid were treated using a method similar to that described in Example 17C to give the title compound. $^1$H NMR (300 MHz, DMSO-$d_6$) δ ppm 11.18 (s, 1H), 8.39 (d, J=2.0 Hz, 2H), 7.93-8.00 (m, 1H), 7.87 (t, J=7.5 Hz, 1H), 2.20-2.31 (m, 3H), 1.74-1.90 (m, 2H), 1.47-1.70 (m, 4H), 1.47 (s, 9H), 1.17-1.33 (m, 2H); MS (ESI$^+$) M/Z 328 (M+H)$^+$.

Example 63

(±)-2-(exo-bicyclo[2.2.1]heptan-2-yl)-N-(4-tert-butyl-1-oxophthalazin-2(1H)-yl)acetamide The products from Example 62A and Example 58A were treated using a method similar to that described in Example 53 to give the title compound. $^1$H NMR (300 MHz, DMSO-$d_6$) δ ppm 11.15 (s, 1H), 8.38-8.39 (m, 1H), 8.36 (d, J=1.4 Hz, 1H), 7.93-8.00 (m, 1H), 7.87 (td, J=7.5, 1.1 Hz, 1H), 2.04-2.33 (m, 4H), 1.83-1.93 (m, 1H), 1.47 (s, 9H), 1.34-1.50 (m, 4H), 1.08-1.22 (m, 4H); MS (ESI$^-$) M/Z 352 (M–H)$^-$.

Example 64

N-(4-tert-butyl-1-oxophthalazin-2(1H)-yl)-3-methyl-3-phenylbutanamide

The product from Example 62A and 3-methyl-3-phenylbutanoic acid were treated using a method similar to that described in Example 51 to give the title compound. $^1$H NMR (300 MHz, DMSO-$d_6$) δ ppm 11.21 (s, 1H), 8.35-8.39 (m, 2H), 7.93-7.99 (m, 1H), 7.84-7.90 (m, 1H), 7.43-7.47 (m, 2H), 7.24-7.39 (m, 2H), 7.15-7.21 (m, 1H), 2.59 (s, 2H), 1.47 (s, 6H), 1.46 (s, 9H); MS (ESI$^-$) M/Z 376 (M–H)$^-$.

Example 65

N-(4-tert-butyl-1-oxophthalazin-2(1H)-yl)-2-(4-chlorophenyl)acetamide

The product from Example 62A and 2-(4-chlorophenyl) acetyl chloride were treated using a method similar to that described in Example 1C to give the title compound. $^1$H NMR (300 MHz, DMSO-$d_6$) δ ppm 11.54 (s, 1H), 8.38 (d, J=8.3 Hz, 1H), 8.37 (dd, J=7.7, 1.6 Hz, 1H), 7.94-8.00 (m, 1H), 7.84-7.90 (m, 1H), 7.41 (s, 4H), 3.68 (s, 2H), 1.47 (s, 9H); MS (ESI$^+$) M/Z 370 (M+H)$^+$.

Example 66

2-[(1S,2S,4R)-bicyclo[2.2.1]hept-2-yl]-N-(4-cyclobutyl-1-oxophthalazin-2(1H)-yl)acetamide The product from Example 67B (78 mg, 0.223 mmol) in MeOH (30 mL) was stirred with 10% Pd/C (20 mg) under hydrogen (1 atm) for 12 hours. The mixture was filtered, concentrated, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to give the title compound 76 mg (93%). $^1$H NMR (400 MHz, DMSO-$d_6$) δ ppm 11.17 (s, 1H), 8.29-8.31 (m, 1H), 7.96 (ddd, J=8.2, 6.9, 1.4 Hz, 1H), 7.85-7.92 (m, 2H), 4.05 (p, J=8.5 Hz, 1H), 2.14-2.42 (m, 9H), 2.02-2.12 (m, 1H), 1.72-1.90 (m, 2H), 1.55-1.66 (m, 1H), 1.44-1.55 (m, 1H), 1.31-1.42 (m, 2H), 1.25-1.28 (m, 1H), 1.11-1.18 (m, 1H), 0.76 (ddd, J=12.1, 4.7, 2.3 Hz, 1H); MS (ESI) m/z 352 (M+H)$^+$.

Example 67

2-[(1S,2S,4S)-bicyclo[2.2.1]hept-5-en-2-yl]-N-(4-cyclobutyl-1-oxophthalazin-2(1H)-yl)acetamide

Example 67A 2-amino-4-cyclobutylphthalazin-1(2H)-one

4-Cyclobutylphthalazin-1(2H)-one was processed using a method similar to that described in Example 1B to afford the title compound. MS (ESI) m/z 216 (M+H)$^+$.

Example 67B

2-[(1S,2S,4S)-bicyclo[2.2.1]hept-5-en-2-yl]-N-(4-cyclobutyl-1-oxophthalazin-2(1H)-yl)acetamide The product of Example 67A and 2-((1S,2S,4S)-bicyclo[2.2.1]hept-5-en-2-yl)acetic acid were processed using a method similar to that described in Example 17C to afford the title compound. $^1$H NMR (400 MHz, DMSO-$d_6$) δ 11.13 (s, 1H), 8.34-8.28 (m, 1H), 8.00-7.93 (m, 1H), 7.92-7.83 (m, 2H), 6.22 (dd, J=5.7, 3.0, 1H), 6.07 (dd, J=5.7, 2.9, 1H), 4.10-3.99 (m, 1H), 2.91 (s, 1H), 2.79 (s, 1H), 2.49-2.42 (m, 1H), 2.41-2.22 (m, 4H), 2.14-2.02 (m, 3H), 1.95-1.87 (m, 1H), 1.86-1.77 (m, 1H), 1.39-1.31 (m, 1H), 1.26 (d, J=8.0, 1H), 0.61 (ddd, J=11.5, 4.2, 2.6, 1H); MS (ESI) m/z 350 (M+H)$^+$.

Example 68

(±)-2-(exo-bicyclo[2.2.1]heptan-2-yl)-N-(4-cyclobutyl-1-oxophthalazin-2(1H)-yl)acetamide The product of Example 67A and the product of Example 58A were treated using a method similar to that described in Example 1C, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to give the title compound. $^1$H NMR (400 MHz, DMSO-$d_6$) δ 11.18 (s, 1H), 8.31 (d, J=8.3, 1H), 8.00-7.92 (m, 1H), 7.89 (dd, J=8.4, 1.4, 2H), 4.09-3.99 (m, 1H), 2.42-2.18 (m, 6H), 2.15 (t, J=6.9, 3H), 1.94-1.77 (m, 2H), 1.55-1.34 (m, 4H), 1.22-1.06 (m, 4H); MS (ESI) m/z 352 (M+H)$^+$.

Example 69

N-(4-cyclobutyl-1-oxophthalazin-2(1H)-yl)-2-(3,5-difluorophenyl)acetamide

The product of Example 67A and 2-(3,5-difluorophenyl) acetic acid were processed using a method similar to that described in Example 17C to afford the title compound. $^1$H NMR (400 MHz, DMSO-$d_6$) δ 11.62 (s, 1H), 8.35-8.28 (m, 1H), 8.01-7.94 (m, 1H), 7.94-7.85 (m, 2H), 7.20-7.10 (m, 3H), 4.12-3.99 (m, 1H), 3.76 (s, 2H), 2.42-2.22 (m, 4H), 2.14-2.00 (m, 1H), 1.89-1.76 (m, 1H); MS (ESI) m/z 370 (M+H)$^+$.

Example 70

2-(4-chlorophenyl)-N-(4-cyclobutyl-1-oxophthalazin-2(1H)-yl)acetamide

The product of Example 67A and 2-(4-chlorophenyl)acetic acid were processed using a method similar to that described in Example 17C to afford the title compound. $^1$H NMR (400 MHz, DMSO-d$_6$) δ ppm 11.57 (s, 1H), 8.31 (d, J=8.3 Hz, 1H), 7.83-8.03 (m, 3H), 7.42 (s, 4H), 4.05 (p, J=8.5 Hz, 1H), 3.70 (s, 2H), 2.21-2.44 (m, 4H), 2.02-2.14 (m, 1H), 1.78-1.87 (m, 1H); MS (ESI) m/z 368 (M+H)$^+$.

Example 71

(±)-2-(exo-bicyclo[2.2.1]heptan-2-yl)-N-(4-cyclopentyl-1-oxophthalazin-2(1H)-yl)acetamide

Example 71A 2-amino-4-cyclopentylphthalazin-1(2H)-one

4-Cyclopentylphthalazin-1(2H)-one was processed using a method similar to that described in Example 1B to afford the title compound. MS (ESI) m/z 230 (M+H)$^+$.

Example 71B (±)-2-(exo-bicyclo[2.2.1]heptan-2-yl)-N-(4-cyclopentyl-1-oxophthalazin-2(1H)-yl)acetamide The product of Example 71A and the product of Example 58A were processed using a method similar to that described in Example 1C, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to afford the title compound. $^1$H NMR (400 MHz, DMSOd$_6$) δ 11.15 (s, 1H), 8.32 (dd, J=7.9, 1.1, 1H), 8.12 (d, J=8.0, 1H), 8.04-7.95 (m, 1H), 7.93-7.84 (m, 1H), 3.69 (p, J=7.7, 1H), 2.24 (dd, J=14.1, 8.4, 2H), 2.12 (dd, J=14.1, 7.4, 2H), 2.08-1.97 (m, 2H), 1.93-1.61 (m, 7H), 1.55-1.34 (m, 4H), 1.14 (dt, J=11.6, 8.8, 4H); MS (ESI) m/z 366 (M+H)$^+$.

Example 72

2-(4-chlorophenyl)-N-(4-cyclopentyl-1-oxophthalazin-2(1H)-yl)acetamide

The product of Example 71A and 2-(4-chlorophenyl)acetic acid were processed using a method similar to that described in Example 17C to afford the title compound. $^1$H NMR (400 MHz, DMSO-d$_6$) δ ppm 11.52-11.54 (bs, 1H), 8.31 (dd, J=7.9, 1.3 Hz, 1H), 8.13 (d, J=8.1 Hz, 1H), 7.97-7.91 (m, 1H), 7.35-7.47 (m, 4H), 3.62-3.77 (m, 3H), 1.96-2.10 (m, 2H), 1.59-1.87 (m, 6H); MS (ESI) m/z 382 (M+H)$^+$.

Example 73

N-(4-cyclopentyl-1-oxophthalazin-2(1H)-yl)-2-(3,5-difluorophenyl)acetamide

The product of Example 71A and 2-(3,5-difluorophenyl) acetic acid were processed using a method similar to that described in Example 17C to afford the title compound. $^1$H NMR (400 MHz, DMSO-d$_6$) δ ppm 11.58-11.61 (bs, 1H), 8.33 (dd, J=7.9, 1.3 Hz, 1H), 8.14 (d, J=8.1 Hz, 1H), 7.98-8.02 (m, 1H), 7.87-7.92 (m, 1H), 7.09-7.22 (m, 3H), 3.74-3.75 (m, 2H), 3.70 (d, J=7.8 Hz, 1H), 1.97-2.11 (m, 2H), 1.59-1.94 (m, 6H); MS (ESI) m/z 384 (M+H)$^+$.

Example 74

(±)-2-(exo-bicyclo[2.2.1]heptan-2-yl)-N-(4-cyclohexyl-1-oxophthalazin-2(1H)-yl)acetamide

Example 74A 2-amino-4-cyclohexylphthalazin-1(2H)-one

4-Cyclohexylphthalazin-1(2H)-one was processed using a method similar to that described in Example 1B to afford the title compound. MS (ESI) m/z 244 (M+H)$^+$.

Example 74B (±)-2-(exo-bicyclo[2.2.1]heptan-2-yl)-N-(4-cyclohexyl-1-oxophthalazin-2(1H)-yl)acetamide The product of Example 74A and the product from Example 58A were processed using a method similar to that described in Example 1C, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to afford the title compound. $^1$H NMR (500 MHz, DMSO-d$_6$) δ ppm 11.15 (s, 1H), 8.32 (dd, J=7.9, 1.3 Hz, 1H), 8.12 (d, J=8.2 Hz, 1H), 7.97-8.01 (m, 1H), 7.87-7.90 (m, 1H), 3.17-3.30 (m, 1H), 2.21-2.26 (m, 2H), 2.10-2.15 (m, 2H), 1.69-1.94 (m, 6H), 1.34-1.64 (m, 9H), 0.87-1.32 (m, 5H), MS (ESI) m/z 380 (M+H)$^+$.

Example 75

2-(adamantan-1-yl)-N-(4-cyclohexyl-1-oxophthalazin-2(1H)-yl)acetamide

The product of Example 74A and 2-(adamantan-1-yl) acetyl chloride were processed using a method similar to that described in Example 1C, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to afford the title compound. $^1$H NMR (400 MHz, DMSO-d$_6$) δ ppm 11.10 (s, 1H), 8.34 (d, J=7.9 Hz, 1H), 8.11 (d, J=8.1 Hz, 1H), 7.97-8.01 (m, 1H), 7.89 (t, J=7.5 Hz, 1H), 3.21-3.40 (m, 1H), 1.39-1.98 (m, 26H), 1.13-1.27 (m, 1H); MS (ESI) m/z 420 (M+H)$^+$.

Example 76

2-(4-chlorophenyl)-N-(4-cyclohexyl-1-oxophthalazin-2(1H)-yl)acetamide

The product of Example 74A and 2-(4-chlorophenyl)acetic acid were processed using a method similar to that described in Example 17C to afford the title compound. $^1$H NMR (400 MHz, DMSO-$d_6$) δ ppm 11.55 (s, 1H), 8.32 (dd, J=7.9, 1.4 Hz, 1H), 8.12 (d, J=8.1 Hz, 1H), 7.97-8.02 (m, 1H), 7.87-7.92 (m, 1H), 7.37-7.47 (m, 4H), 3.68 (s, 2H), 3.22-3.29 (bs, 1H), 1.87-1.92 (m, 2H), 1.78-1.82 (m, 2H), 1.70-1.76 (m, 1H), 1.41-1.54 (m, 4H), 1.18-1.29 (m, 1H); MS (ESI) m/z 396 (M+H)$^+$.

Example 77

N-(4-cyclohexyl-1-oxophthalazin-2(1H)-yl)-2-(3,5-difluorophenyl)acetamide

The product of Example 74A and 2-(3,5-difluorophenyl)acetic acid were processed using a method similar to that described in Example 17C to afford the title compound. $^1$H NMR (400 MHz, DMSO-$d_6$) δ ppm 11.60-11.61 (bs, 1H), 8.34 (dd, J=7.9, 1.4 Hz, 1H), 8.13 (d, J=8.2 Hz, 1H), 8.00 (ddd, J=8.1, 7.2, 1.5 Hz, 1H), 7.90 (ddd, J=8.0, 7.1, 1.0 Hz, 1H), 7.07-7.22 (m, 3H), 3.75 (s, 2H), 3.26 (d, J=10.3 Hz, 1H), 1.89-1.93 (m, 2H), 1.79-1.83 (m, 2H), 1.70-1.76 (m, 1H), 1.39-1.58 (m, 4H), 1.19-1.32 (m, 1H); MS (ESI) m/z 398 (M+H)$^+$.

Example 78

(±)-4-(3-{[(exo-bicyclo[2.2.1]heptan-2-yl)acetyl]amino}-4-oxo-3,4-dihydrophthalazin-1-yl)benzoic acid A mixture of the product from Example 79 (0.108 g, 0.25 mmol) and 1 N aqueous sodium hydroxide (0.55 mL, 0.55 mmol) in MeOH (0.3 mL) and THF (0.6 mL) was stirred for 4 hours, concentrated, diluted with EtOAc, acidified with 1N HCl, washed with water, dried (Na$_2$SO$_4$), filtered, and concentrated to give the title compound (89.2 mg) as an orange solid. $^1$H NMR (500 MHz, DMSO-$d_6$) δ 13.5-12.8 (br s, 1H), 11.37 (s, 1H), 8.45-8.38 (m, 1H), 8.13 (d, J=8.2, 2H), 8.00-7.93 (m, 2H), 7.79-7.69 (m, 3H), 2.28 (dd, J=14.2, 8.3, 1H), 2.21 (m, 1H), 2.19-2.09 (m, 2H), 1.91 (m, 1H), 1.46 (m, 3H), 1.38 (d, J=9.8, 1H), 1.17-1.07 (m, 4H); MS (ESI+) M/Z 418 (M+H)+.

Example 79

(±)-methyl 4-(3-{[exo-bicyclo[2.2.1]hept-2-ylacetyl]amino}-4-oxo-3,4-dihydrophthalazin-1-yl)benzoate A solution of the product from Example 84 (0.128 g, 0.28 mmol) in MeOH (20 mL) was added to PdCl$_2$(dppf) (10.4 mg, 0.014 mmol) and triethylamine (0.079 mL, 0.57 mmol) in a 50 ml pressure bottle. The mixture was pressurized with CO (60 psi), and stirred for 16 hours at 100° C. The mixture was concentrated and chromatographed on SiO$_2$ (35% EtOAc/hexanes) to give the title compound (114.0 mg) as an orange solid; $^1$H NMR (300 MHz, DMSO-$d_6$) δ 11.36 (s, 1H), 8.41 (dt, J=6.5, 2.9, 1H), 8.15 (d, J=8.4, 2H), 8.02-7.92 (m, 2H), 7.79-7.70 (m, 3H), 3.92 (s, 3H), 2.28 (dd, J=14.3, 8.3, 1H), 2.23-2.08 (m, 3H), 1.95-1.83 (m, 1H), 1.56-1.33 (m, 4H), 1.22-1.05 (m, 4H); MS (ESI$^+$) m/z 432 (M+H)$^+$.

Example 80 methyl 4-(3-{[(4-chlorophenyl)acetyl]amino}-4-oxo-3,4-dihydrophthalazin-1-yl)benzoate The product from Example 3 was treated similarly as described in Example 79 to give the title compound. $^1$H NMR (300 MHz, DMSO-$d_6$) δ 11.74 (s, 1H), 8.40 (s, 1H), 8.14 (d, J=8.3, 2H), 8.01-7.92 (m, 2H), 7.76 (d, J=8.2, 3H), 7.40 (s, 4H), 3.91 (s, 3H), 3.71 (s, 2H); MS (ESI+) m/z 448 (M+H)$^+$.

Example 81

(±)-4-(3-{[exo-bicyclo[2.2.1]hept-2-ylacetyl]amino}-4-oxo-3,4-dihydrophthalazin-1-yl)-N,N-dimethylbenzamide

Example 81A

N,N-dimethyl-4-(4-oxo-3,4-dihydrophthalazin-1-yl)benzamide

A mixture of 4-chlorophthalazin-1(2H)-one (550 mg, 3.05 mmol), 4 (dimethylcarbamoyl)phenylboronic acid (588 mg, 3.05 mmol) Cs$_2$CO$_3$ (1985 mg, 6.09 mmol) and PdCl$_2$(dppf).CH$_2$Cl$_2$ (130 mg, 0.15 mmol) in dioxane (8 mL) was heated at 160° C. for 20 minutes under microwave conditions. The mixture was diluted with EtOAc and washed with saturated aqueous NaHCO$_3$, dried (Na$_2$SO$_4$), filtered, and concentrated. The residue was purified by Intelliflash280™ (SiO$_2$, 95% hexanes/EtOAc to 10% hexanes/EtOAc) to afford the title compound (75 mg, 8%). MS (APCI+) m/z 294 (M+H)$^+$.

Example 81B 4-(3-amino-4-oxo-3,4-dihydrophthalazin-1-yl)-N,N-dimethylbenzamide The product from Example 81A was processed using a method similar to that described in Example 1B to afford the title compound. MS (APCI+) m/z 309 (M+H)$^+$.

Example 81C (±)-4-(3-{[exo-bicyclo[2.2.1]hept-2-ylacetyl]amino}-4-oxo-3,4-dihydrophthalazin-1-yl)-N,N-dimethylbenzamide The product of Example 81B and the product from Example 58A were processed using a method similar to that described in Example 1C, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to afford the title compound: $^1$H NMR (400 MHz, DMSO) δ 11.36 (s, 1H), 8.41 (m, 1H), 8.01-7.93 (m, 2H), 7.79-7.74 (m, 1H), 7.66 (d, J=8.1, 2H), 7.59 (d, J=8.1, 2H), 3.00 (d, J=20.0, 6H), 2.30-2.23 (m, 1H), 2.18-2.23 (m, 1H), 2.09-2.18 (m, 2H), 1.84-1.94 (m, 1H), 1.42-1.53 (m, 3H), 1.35-1.41 (m, 1H), 1.07-1.21 (m, 4H); MS (APCI$^+$) m/z 445 (M+H)$^+$.

Example 82

3-methyl-N-(1-oxo-4-phenylphthalazin-2(1H)-yl)-3-phenylbutanamide

The product of Example 17B and 3-methyl-3-phenylbutanoic acid were processed using a method similar to that described in Example 17C to afford the title compound. $^1$H NMR (400 MHz, DMSO-d$_6$) δ ppm 11.39 (s, 1H), 8.40-8.42 (m, 1H), 7.89-8.02 (m, 2H), 7.72-7.75 (m, 1H), 7.55-7.61 (m, 5H), 7.42-7.47 (m, 2H), 7.28-7.34 (m, 2H), 7.15-7.20 (m, 1H), 2.62 (s, 2H), 1.47 (s, 6H); MS (APCI+) m/z 398 (M+H)$^+$.

Example 83

2-(2,4-dichlorophenyl)-N-(1-oxo-4-phenylphthalazin-2(1H)-yl)acetamide

The product of Example 17B and 2-(2,4-dichlorophenyl)acetic acid were processed using a method similar to that described in Example 17C to afford the title compound. $^1$H NMR (500 MHz, DMSO-d$_6$) δ ppm 11.73-11.75 (m, 1H), 8.41 (dd, J=7.0, 2.2 Hz, 1H), 7.91-8.02 (m, 2H), 7.72-7.74 (m, 1H), 7.63 (d, J=2.1 Hz, 1H), 7.57-7.61 (m, 5H), 7.56 (d, J=8.4 Hz, 1H), 7.44 (dd, J=8.3, 2.2 Hz, 1H), 3.87 (s, 2H); MS (APCI+) m/z 424 (M+H)$^+$.

Example 84

(±)-2-(exo-bicyclo[2.2.1]heptan-2-yl)-N-[4-(4-bromophenyl)-1-oxophthalazin-2(1H)-yl]acetamide The products from Example 2A and Example 58A were treated using a method similar to that described in Example 53 to give the title compound. $^1$H NMR (300 MHz, DMSO-d$_6$) δ ppm 11.34-11.36 (bs, 1H), 8.37-8.43 (m, 1H), 7.92-8.01 (m, 2H), 7.75-7.81 (m, 2H), 7.70-7.76 (m, 1H), 7.52-7.61 (m, 2H), 2.27 (dd, J=14.2, 8.3 Hz, 1H), 2.18-2.23 (m, 1H), 2.14 (dd, J=14.2, 7.4 Hz, 1H), 2.08-2.13 (m, 1H), 1.84-1.94 (m, 1H), 1.34-1.56 (m, 4H), 1.07-1.21 (m, 4H); MS (ESI$^+$) M/Z 452 (M+H)$^+$.

Example 85

N-[4-(4-bromophenyl)-1-oxophthalazin-2(1H)-yl]-3-methyl-3-phenylbutanamide

The products from Example 2A and 3-methyl-3-phenylbutanoic acid were treated using a method similar to that described in Example 51 to give the title compound. $^1$H NMR (300 MHz, DMSO-d$_6$) δ ppm 11.38 (s, 1H), 8.39-8.42 (m, 1H), 7.88-8.04 (m, 2H), 7.76-7.81 (m, 2H), 7.70-7.77 (m, 1H), 7.53-7.58 (m, 2H), 7.42-7.46 (m, 2H), 7.25-7.36 (m, 2H), 7.15-7.21 (m, 1H), 2.62 (s, 2H), 1.47 (s, 6H); MS (ESI$^-$) M/Z 474 (M-H)$^-$.

Example 86

N-[4-(4-chlorophenyl)-1-oxophthalazin-2(1H)-yl]-2-(1-methylcyclopentyl)acetamide

Example 86A

2-amino-4-(4-chlorophenyl)phthalazin-1(2H)-one 4-(4-chlorophenyl)phthalazin-1(2H)-one was treated as in Example 2A to give the title compound. MS (APCI$^+$) M/Z 272 (M+H)$^+$.

Example 86B

N-[4-(4-chlorophenyl)-1-oxophthalazin-2(1H)-yl]-2-(1-methylcyclopentyl)acetamide The product from Example 86A and 1-methylcyclopentanecarboxylic acid were treated using a method similar to that described in Example 39 to give the title compound. $^1$H NMR (300 MHz, DMSO-d$_6$) δ ppm 11.33 (s, 1H), 8.39-8.43 (m, 1H), 7.88-8.05 (m, 2H), 7.69-7.77 (m, 1H), 7.60-7.68 (m, 4H), 2.29 (s, 2H), 1.58-1.73 (m, 3H), 1.64 (s, 3H), 1.32-1.48 (m, 2H), 1.11 (s, 3H); MS (ESI$^-$) M/Z 394 (M-H)$^-$.

Example 87

N-[4-(4-chlorophenyl)-1-oxophthalazin-2(1H)-yl]-2-[1-(trifluoromethyl)cyclopentyl]acetamide A solution of 1-(trifluoromethyl)cyclopentanecarboxylic acid and oxalyl chloride in dichloromethane containing a catalytic amount of DMF was stirred for 2 hours, concentrated, re-dissolved in 1:1 acetonitrile:THF, and cooled to 0° C. A solution of (diazomethyl)trimethylsilane in Et$_2$O was added, and the mix was stirred for 4 h, allowing to warm to room temperature, concentrated, washed with saturated aqueous NaHCO$_3$ and brine, dried (Na$_2$SO$_4$), filtered, and concentrated to give crude product which was used without purification.

A solution of the above crude 2-diazo-1-(1-(trifluoromethyl)cyclopentyl)ethanone and the product from Example 86A in 1,2-dichloroethane and 1-methyl-2-pyrrolidinone was microwaved at 200° C. for 15 minutes, diluted with EtOAc, washed with saturated aqueous NaHCO$_3$ and brine, dried (Na$_2$SO$_4$), and filtered. The residue was chromatographed on SiO$_2$ (1-2% acetone/dichloromethane) to give the title compound as a white solid: $^1$H NMR (300 MHz, CDCl$_3$) δ ppm 8.50-8.58 (m, 1H), 8.47-8.50 (bs, 1H), 7.78-7.86 (m, 2H), 7.67-7.75 (m, 1H), 7.52-7.57 (m, 2H), 7.48-7.52 (m, 2H), 2.67 (s, 2H), 2.07-2.18 (m, 2H), 1.94-2.04 (m, 2H), 1.67-1.84 (m, 4H); MS (ESI$^-$) M/Z 448 (M-H)$^-$.

Example 88

N-[4-(4-chlorophenyl)-1-oxophthalazin-2(1H)-yl]-2-[(1S,2S,5R)-3,3-difluoro-6,6-dimethylbicyclo[3.1.1]hept-2-yl]acetamide

Example 88A (1R,5R)-3,3-difluoro-6,6-dimethylbicyclo[3.1.1]heptan-2-one

To a 1M solution of sodium bis(trimethylsilyl)amide in tetrahydrofuran (Aldrich, 50.6 mL, 50.6 mmol) was added a solution of (+)-nopinone (Aldrich, 2.0 g, 14.5 mmol) in tetrahydrofuran (200 mL) at −78° C. under nitrogen atmosphere, and then the mixture was stirred at 0° C. for 30 minutes. After cooling at −78° C., a solution of N-fluorobenzenesulfonamide (18.3 g, 57.9 mmol) in tetrahydrofuran (100 mL) was added to the reaction mixture and stirred at room temperature for 1 hour. The reaction mixture was then quenched with 1M HCl aqueous solution (80 mL) and concentrated under reduced pressure. The residue was diluted with EtOAc (100 mL), and washed with 1 M HCl aqueous solution (2×100 mL), brine (100 mL), and 1M NaHCO$_3$ aqueous solution (100 mL), dried (Na$_2$SO$_4$), filtered, and concentrated under reduced pressure. The residue was purified by column chromatography using an Analogix® Intelliflash280™ (SiO₂, 0-20% of EtOAc in hexanes) to obtain 1.0 g of the title compound. MS (DCI/NH₃) m/z 192 (M+NH₄)⁺.

Example 88B ethyl 2-((1R,5R)-3,3-difluoro-6,6-dimethylbicyclo [3.1.1]heptan-2-ylidene)acetate To a suspension of NaH (0.31 g, 7.8 mmol, 60% dispersion in oil) in 1,2-dimethoxy ethane (30 mL) at 0° C. was added triethyl phosphono acetate (1.5 mL, 7.8 mmol). The resulting mixture was stirred 15 minutes at 0° C., 15 minutes at room temperature, and cooled to 0° C. Then, a solution of the product from Example 88A (0.9 g, 5.2 mmol) in 1,2-dimethoxy ethane (20 mL) was added and the resulting solution was stirred for 5 minutes at 0° C., and then stirred at room temperature overnight. Water was added and the aqueous layer was extracted with ethyl acetate (3×20 mL). The combined organic layers were washed with H₂O (20 mL), brine (20 mL), dried over MgSO₄, filtered and concentrated under reduced pressure. The residue was purified by flash chromatography using an Analogix® Intelliflash280™ (Hexanes-EtOAc, 0 to 20%) to give the title compound. MS (DCI/NH₃) m/z 262 (M+NH₄)⁺

Example 88C ethyl 2-((1S,2S,5R)-3,3-difluoro-6,6-dimethylbicyclo[3.1.1]heptan-2-yl)acetate A mixture of the product from Example 88B (0.8 g, 3.3 mmol) and 10% Pd/C (70 mg, 0.07 mmol) in ethanol (20 mL) was stirred under H₂ (1 atm) using a balloon until the starting material was completely consumed. The mixture was filtered and concentrated under reduced pressure to obtain 0.8 g of the title compound. MS (DCI/NH₃) m/z 264 (M+NH₄)⁺.

Example 88D 2-((1S,2S,5R)-3,3-difluoro-6,6-dimethylbicyclo [3.1.1]heptan-2-yl)acetic acid To a solution of the product from Example 88C (0.8 g, 3.25 mmol) in tetrahydrofuran (6 mL), methanol (3 mL) and water (3 mL) was added 5M NaOH (3.3 mL, 16.2 mmol). After stirring at room temperature for 16 hours, the reaction mixture was concentrated to half the volume, washed with dichloromethane (10 mL), neutralized to pH~2, and extracted with dichloromethane (3×15 mL). The combined organic layers were dried (Na₂SO₄), filtered and concentrated under reduced pressure to obtain 0.6 g of the title compound. MS (DCI/NH₃) m/z 236 (M+NH₄)⁺

Example 88E

N-[4-(4-chlorophenyl)-1-oxophthalazin-2(1H)-yl]-2-[(1S,2S,5R)-3,3-difluoro-6,6-dimethylbicyclo[3.1.1]hept-2-yl]acetamide To a mixture of the product from Example 88D (60 mg, 0.275 mmol) in thionyl chloride (140 μL, 1.924 mmol) was added one drop of DMF. The reaction was stirred at room temperature for 2 hours. The excess of SOCl₂ was evaporated and the product was dried under vacuum, and used without purification.
To a mixture of the above crude 2-((1S,2S,5R)-3,3-difluoro-6,6-dimethylbicyclo[3.1.1]heptan-2-yl)acetyl chloride (50 mg, 0.211 mmol) and the product from Example 86A (57.4 mg, 0.211 mmol) in 10 mL of CHCl₃ was added pyridine (0.051 mL, 0.634 mmol). The reaction is stirred at rt for 12 hours and then reluxed for 16 hours, and quenched with 1M NaHCO3 (10 mL). The aq layer was extracted with EtOAc (2×20 mL), and the combined organic layers were dried (Na₂SO₄), filtered, and concentrated. The residue was purified by column chromatography using an Analogix® Intelliflash280™ (SiO₂, 0-40% of EtOAc in hexanes). ¹H NMR (300 MHz, DMSO-d₆) δ ppm 11.51 (s, 1H), 8.39-8.43 (m, 1H), 7.94-8.00 (m, 2H), 7.70-7.76 (m, 1H), 7.58-7.70 (m, 4H), 2.92-3.09 (m, 1H), 2.81 (dd, J=15.3, 6.4 Hz, 1H), 2.36-2.45 (m, 3H), 2.11-2.16 (m, 1H), 1.93-2.04 (m, 1H), 1.27 (s, 3H), 1.08-1.20 (m, 2H), 1.01 (s, 3H); MS (ESI⁺) M/Z 472 (M+H)⁺.

Example 89

N-[4-(4-chlorophenyl)-1-oxophthalazin-2(1H)-yl]-3-methyl-3-phenylbutanamide

The product of Example 86A and 3-methyl-3-phenylbutanoic acid were treated as in Example 51 to give the title compound. ¹H NMR (300 MHz, DMSO-d₆) δ ppm 11.39 (s, 1H), 8.39-8.44 (m, 1H), 7.88-8.02 (m, 2H), 7.70-7.77 (m, 1H), 7.63-7.67 (m, 2H), 7.60-7.63 (m, 2H), 7.42-7.46 (m, 2H), 7.28-7.34 (m, 2H), 7.15-7.21 (m, 1H), 2.62 (s, 2H), 1.47 (s, 6H); MS (APCI⁺) M/Z 432 (M+H)⁺.

Example 90

N-[4-(4-chlorophenyl)-1-oxophthalazin-2(1H)-yl]-2-fluoro-2-phenylacetamide

The product of Example 86A and 2-fluoro-2-phenylacetyl chloride were treated using a method similar to that described in Example 1C to give the title compound. ¹H NMR (300 MHz, DMSO-d₆) δ ppm 12.22 (s, 1H), 8.39-8.45 (m, 1H), 7.90-8.07 (m, 2H), 7.69-7.78 (m, 1H), 7.61-7.68 (m, 6H), 7.46-7.53 (m, 3H), 6.26 (d, J=47.1 Hz, 1H); MS (ESI+) M/Z 408 (M+H)+.

Example 91

N-[4-(4-chlorophenyl)-1-oxophthalazin-2(1H)-yl]-2-phenylacetamide

The product of Example 86A and 2-phenylacetyl chloride were treated as in Example 53 to give the title compound. ¹H NMR (300 MHz, DMSO-d₆) δ ppm 11.70 (s, 1H), 8.39-8.44 (m, 1H), 7.85-8.05 (m, 2H), 7.69-7.76 (m, 1H), 7.59-7.66 (m, 4H), 7.21-7.41 (m, 5H), 3.69 (s, 2H); MS (ESI+) M/Z 390 (M+H)+.

Example 92

N-[4-(4-chlorophenyl)-1-oxophthalazin-2(1H)-yl]-2-(morpholin-4-yl)acetamide

The product of Example 86A and 2-morpholinoacetic acid hydrochloride were treated using a method similar to that described in Example 57 to give the title compound. ¹H NMR (500 MHz, DMSO-d₆/Deuterium Oxide) δ ppm 8.42-8.46 (m, 1H), 7.96-8.08 (m, 2H), 7.75-7.79 (m, 1H), 7.64-7.69 (m, 4H), 4.27-4.28 (m, 2H), 3.79-3.94 (m, 4H), 3.34-3.38 (m, 4H); MS (APCI⁺) M/Z 399 (M+H)⁺.

Example 93

N-[4-(4-chlorophenyl)-1-oxophthalazin-2(1H)-yl]-2-(pyridin-3-yl)acetamide

The product of Example 86A and 2-(pyridin-3-yl)acetic acid hydrochloride were treated using a method similar to that described in Example 57 to give the title compound. $^1$H NMR (500 MHz, DMSO-d$_6$/Deuterium Oxide) δ ppm 8.83-8.84 (bs, 1H), 8.75 (d, J=5.5 Hz, 1H), 8.36-8.50 (m, 2H), 7.96-8.02 (m, 2H), 7.92 (dd, J=8.0, 5.5 Hz, 1H), 7.73-7.75 (m, 1H), 7.59-7.70 (m, 4H), 4.00 (s, 2H); MS (APCI$^+$) M/Z 391 (M+H)$^+$.

Example 94

N-[4-(4-chlorophenyl)-1-oxophthalazin-2(1H)-yl]-2-(pyridin-2-yl)acetamide

The product of Example 86A and 2-(pyridin-2-yl)acetic acid hydrochloride were treated using a method similar to that described in Example 57 to give the title compound. $^1$H NMR (500 MHz, DMSO-d$_6$/Deuterium Oxide) δ ppm 8.71-8.73 (m, 1H), 8.41-8.43 (m, 1H), 8.22 (td, J=7.8, 1.7 Hz, 1H), 7.94-8.06 (m, 2H), 7.82 (d, J=7.9 Hz, 1H), 7.73-7.75 (m, 1H), 7.69 (d, J=6.8 Hz, 1H), 7.59-7.67 (m, 4H); MS (APCI$^+$) M/Z 391 (M+H)$^+$.

Example 95

N-[4-(4-chlorophenyl)-1-oxophthalazin-2(1H)-yl]-2-(3,4-dichlorophenyl)acetamide

The product of Example 86A and 2-(3,4-dichlorophenyl)acetic acid were treated using a method similar to that described in Example 57 to give the title compound. $^1$H NMR (500 MHz, DMSO-d$_6$/Deuterium Oxide) δ ppm 8.40-8.43 (m, 1H), 7.90-8.04 (m, 2H), 7.72-7.75 (m, 1H), 7.58-7.70 (m, 6H), 7.38 (dd, J=8.3, 2.1 Hz, 1H), 3.75 (s, 2H); MS (ESI$^-$) M/Z 456 (M−H)$^-$.

Example 96

N-[4-(4-chlorophenyl)-1-oxophthalazin-2(1H)-yl]-2-(3,5-dimethoxyphenyl)acetamide The product of Example 86A and 2-(3,5-dimethoxyphenyl)acetic acid were treated using a method similar to that described in Example 57 to give the title compound. $^1$H NMR (500 MHz, DMSO-d$_6$/Deuterium Oxide) δ ppm 8.41-8.43 (m, 1H), 7.90-8.04 (m, 2H), 7.72-7.74 (m, 1H), 7.62-7.66 (m, 4H), 6.58 (d, J=2.3 Hz, 2H), 6.41 (t, J=2.3 Hz, 1H), 3.75 (s, 6H), 3.74 (s, 2H); MS (ESI$^-$) M/Z 448 (M−H)$^-$.

Example 97

N-[4-(4-chlorophenyl)-1-oxophthalazin-2(1H)-yl]-2-(3,5-dimethylphenyl)acetamide

The product of Example 86A and 2-(3,5-dimethylphenyl)acetic acid were treated using a method similar to that described in Example 57 to give the title compound. $^1$H NMR (500 MHz, DMSO-d$_6$/Deuterium Oxide) δ ppm 8.41-8.43 (m, 1H), 7.93-8.04 (m, 2H), 7.72-7.74 (m, 1H), 7.59-7.69 (m, 4H), 6.98-6.99 (bs, 2H), 6.90-6.91 (bs, 1H), 3.60 (s, 2H), 2.26 (s, 6H); MS (ESI$^-$) M/Z 416 (M−H)$^-$.

Example 98

N-[4-(4-chlorophenyl)-1-oxophthalazin-2(1H)-yl]-2-[3-(trifluoromethoxy)phenyl]acetamide The product of Example 86A and 2-[3-(trifluoromethoxy)phenyl]acetic acid were treated using a method similar to that described in Example 57 to give the title compound. $^1$H NMR (500 MHz, DMSO-d$_6$/Deuterium Oxide) δ ppm 8.41-8.43 (m, 1H), 7.95-8.02 (m, 2H), 7.73-7.75 (m, 1H), 7.63-7.64 (m, 4H), 7.50 (t, J=7.9 Hz, 1H), 7.42 (d, J=7.8 Hz, 1H), 7.38-7.40 (bs, 1H), 7.27-7.30 (m, 1H), 3.79 (s, 2H); MS (ESI$^-$) M/Z 472 (M−H)$^-$.

Example 99

N-[4-(4-chlorophenyl)-1-oxophthalazin-2(1H)-yl]-2-[4-(trifluoromethyl)phenyl]acetamide The product of Example 86A and 2-[4-(trifluoromethyl)phenyl]acetic acid were treated using a method similar to that described in Example 57 to give the title compound. $^1$H NMR (500 MHz, DMSO-d$_6$/Deuterium Oxide) δ ppm 8.40-8.42 (m, 1H), 7.93-8.04 (m, 2H), 7.72-7.74 (m, 3H), 7.59-7.69 (m, 6H), 3.83-3.84 (bs, 2H); MS (ESI$^-$) M/Z 456 (M−H)$^-$.

Example 100

N-[4-(4-chlorophenyl)-1-oxophthalazin-2(1H)-yl]-2-[3-(trifluoromethyl)phenyl]acetamide The product of Example 86A and 2-[3-(trifluoromethyl)phenyl]acetic acid were treated using a method similar to that described in Example 57 to give the title compound. $^1$H NMR (500 MHz, DMSO-d$_6$/Deuterium Oxide) δ ppm 8.40-8.43 (m, 1H), 7.93-8.04 (m, 2H), 7.72-7.79 (m, 2H), 7.57-7.70 (m, 7H), 3.84 (s, 2H); MS (ESI$^-$) M/Z 456 (M−H)$^-$.

Example 101

N-[4-(4-chlorophenyl)-1-oxophthalazin-2(1H)-yl]-2-[4-(dimethylamino)phenyl]acetamide The product of Example 86A and 2-[4-(dimethylamino)phenyl]acetic acid were treated using a method similar to that described in Example 57 to give the title compound. $^1$H NMR (500 MHz, DMSO-d$_6$/Deuterium Oxide) δ ppm 8.40-8.42 (m, 1H), 7.93-8.04 (m, 2H), 7.71-7.74 (m, 1H), 7.58-7.69 (m, 4H), 7.41-7.43 (m, 2H), 7.23-7.25 (m, 2H), 3.68-3.69 (bs, 2H), 3.06 (s, 6H); MS (APCI$^+$) M/Z 433 (M+H)$^+$.

Example 102

2-(4-bromophenyl)-N-[4-(4-chlorophenyl)-1-oxophthalazin-2(1H)-yl]acetamide

The product of Example 86A and 2-(4-bromophenyl)acetic acid were treated using a method similar to that described in Example 57 to give the title compound. $^1$H NMR (500 MHz, DMSO-d$_6$/Deuterium Oxide) δ ppm 8.40-8.44 (m, 1H), 7.93-8.04 (m, 2H), 7.72-7.75 (m, 1H), 7.60-7.67 (m, 4H), 7.54-7.57 (m, 2H), 7.34-7.36 (m, 2H), 3.69 (s, 2H); MS (ESI−) M/Z 466 (M−H)−.

Example 103

2-(3-chlorophenyl)-N-[4-(4-chlorophenyl)-1-oxophthalazin-2(1H)-yl]acetamide

The product of Example 86A and 2-(3-chlorophenyl)acetic acid were treated using a method similar to that described in Example 57 to give the title compound. $^1$H NMR (500 MHz, DMSO-d$_6$/Deuterium Oxide) δ ppm 8.41-8.43 (m, 1H), 7.93-8.04 (m, 2H), 7.72-7.75 (m, 1H), 7.62-7.66 (m, 4H), 7.47 (t, J=1.8 Hz, 1H), 7.31-7.42 (m, 3H), 3.74 (s, 2H); MS (ESI$^-$) M/Z 422 (M–H)$^-$.

Example 104

N-[4-(4-chlorophenyl)-1-oxophthalazin-2(1H)-yl]-2-(4-methoxyphenyl)acetamide

The product of Example 86A and 2-(4-methoxyphenyl)acetic acid were treated using a method similar to that described in Example 57 to give the title compound. $^1$H NMR (500 MHz, DMSO-d$_6$/Deuterium Oxide) δ ppm 8.40-8.42 (m, 1H), 7.88-8.03 (m, 2H), 7.71-7.74 (m, 1H), 7.58-7.68 (m, 4H), 7.29-7.31 (m, 2H), 6.90-6.93 (m, 2H), 3.74 (s, 3H), 3.62 (s, 2H); MS (APCI+) M/Z 420 (M+H)+.

Example 105

N-[4-(4-chlorophenyl)-1-oxophthalazin-2(1H)-yl]-2-(3-methoxyphenyl)acetamide

The product of Example 86A and 2-(3-methoxyphenyl)acetic acid were treated using a method similar to that described in Example 57 to give the title compound. $^1$H NMR (500 MHz, DMSO-d$_6$/Deuterium Oxide) δ ppm 8.41-8.43 (m, 1H), 7.96-8.01 (m, 2H), 7.72-7.74 (m, 1H), 7.60-7.67 (m, 4H), 7.27 (t, J=7.9 Hz, 1H), 6.98 (d, J=2.4 Hz, 1H), 6.96 (d, J=7.6 Hz, 1H), 6.85 (dd, J=8.2, 2.6 Hz, 1H), 3.76 (s, 3H), 3.67-3.67 (bs, 2H; MS (ESI$^-$) M/Z 418 (M–H)$^-$.

Example 106

N-[4-(4-chlorophenyl)-1-oxophthalazin-2(1H)-yl]-2-(4-hydroxyphenyl)acetamide

The product of Example 86A and 2-(4-hydroxyphenyl)acetic acid were treated using a method similar to that described in Example 57 to give the title compound. $^1$H NMR (500 MHz, DMSO-d$_6$/Deuterium Oxide) δ ppm 8.38-8.42 (m, 1H), 7.95-8.02 (m, 2H), 7.72-7.75 (m, 1H), 7.60-7.67 (m, 4H), 7.17-7.19 (m, 2H), 6.73-6.75 (m, 2H), 3.57 (s, 2H); MS (ESI$^-$) M/Z 404 (M–H)$^-$.

Example 107

N-[4-(4-chlorophenyl)-1-oxophthalazin-2(1H)-yl]-2-(4-methylphenyl)acetamide

The product of Example 86A and 2-(4-methylphenyl)acetic acid were treated using a method similar to that described in Example 57 to give the title compound. $^1$H NMR (500 MHz, DMSO-d$_6$/Deuterium Oxide) δ ppm 8.40-8.42 (m, 1H), 7.90-8.03 (m, 2H), 7.71-7.73 (m, 1H), 7.53-7.68 (m, 4H), 7.25-7.27 (m, 2H), 7.15-7.17 (m, 2H), 3.64 (s, 2H), 2.29 (s, 3H); MS (APCI$^+$) M/Z 404 (M+H)$^+$.

Example 108

N-[4-(4-chlorophenyl)-1-oxophthalazin-2(1H)-yl]-2-(3-methylphenyl)acetamide

The product of Example 86A and 2-(3-methylphenyl)acetic acid were treated using a method similar to that described in Example 57 to give the title compound. $^1$H NMR (500 MHz, DMSO-d$_6$/Deuterium Oxide) δ ppm 8.41-8.43 (m, 1H), 7.93-8.04 (m, 2H), 7.72-7.74 (m, 1H), 7.60-7.66 (m, 4H), 7.24 (t, J=7.5 Hz, 1H), 7.19-7.21 (m, 1H), 7.16-7.19 (m, 1H), 7.08-7.12 (m, 1H), 3.65 (s, 2H), 2.31 (s, 3H); MS (ESI$^-$) M/Z 402 (M–H)$^-$.

Example 109

N-[4-(4-chlorophenyl)-1-oxophthalazin-2(1H)-yl]-2-cyclopentylacetamide

The product of Example 86A and 2-cyclopentylacetic acid were treated using a method similar to that described in Example 57 to give the title compound. $^1$H NMR (500 MHz, DMSO-d$_6$/Deuterium Oxide) δ ppm 8.40-8.43 (m, 1H), 7.88-8.04 (m, 2H), 7.73-7.75 (m, 1H), 7.59-7.69 (m, 4H), 2.33 (d, J=7.4 Hz, 2H), 2.16-2.28 (m, 1H), 1.75-1.87 (m, 2H), 1.59-1.69 (m, 2H), 1.49-1.58 (m, 2H), 1.19-1.31 (m, 2H); MS (ESI$^-$) M/Z 380 (M–H)$^-$.

Example 110

N-[4-(4-chlorophenyl)-1-oxophthalazin-2(1H)-yl]-4-methylpentanamide

The product of Example 86A and 4-methylpentanoic acid were treated using a method similar to that described in Example 57 to give the title compound. $^1$H NMR (500 MHz, DMSO-d$_6$/Deuterium Oxide) δ ppm 8.40-8.42 (m, 1H), 7.88-8.04 (m, 2H), 7.72-7.75 (m, 1H), 7.59-7.69 (m, 4H), 2.34 (t, J=7.7 Hz, 2H), 1.57-1.68 (m, 1H), 1.49-1.54 (m, 2H), 0.92 (d, J=6.6 Hz, 6H); MS (ESI$^-$) M/Z 368 (M–H)$^-$.

Example 111

N-[4-(4-chlorophenyl)-1-oxophthalazin-2(1H)-yl]-2-[4-(methylsulfonyl)phenyl]acetamide The product of Example 86A and 2-[4-(methylsulfonyl)phenyl]acetic acid were treated using a method similar to that described in Example 57 to give the title compound. $^1$H NMR (500 MHz, DMSO-d$_6$/Deuterium Oxide) δ ppm 8.40-8.43 (m, 1H), 7.95-8.02 (m, 2H), 7.90-7.94 (m, 2H), 7.72-7.75 (m, 1H), 7.65-7.68 (m, 2H), 7.61-7.66 (m, 4H), 3.86 (s, 2H), 3.20 (s, 3H); MS (ESI–) M/Z 466 (M–H)–.

Example 112

N-[4-(4-chlorophenyl)-1-oxophthalazin-2(1H)-yl]-2-(5-chloro-2-thienyl)acetamide

The product of Example 86A and 2-(5-chlorothiophen-2-yl)acetic acid were treated using a method similar to that described in Example 5 to give the title compound. $^1$H NMR (300 MHz, DMSO-d$_6$) δ ppm 11.77-11.81 (bs, 1H), 8.39-8.42 (m, 1H), 7.84-8.05 (m, 2H), 7.70-7.76 (m, 1H), 7.56-7.68 (m, 4H), 6.99 (d, J=3.8 Hz, 1H), 6.92 (d, J=3.8 Hz, 1H), 3.91-3.92 (bs, 2H); MS (ESI$^+$) M/Z 430 (M+H)$^+$.

Example 113

(±)-2-(exo-bicyclo[2.2.1]hept-2-yl)-N-[4-(4-chlorophenyl)-1-oxophthalazin-2(1H)-yl]acetamide The products from Example 86A and Example 58A were treated using a method similar to that described in Example 1C to give the title compound. $^1$H NMR (300 MHz, DMSO-d$_6$) δ ppm 11.30-11.37 (m, 1H), 8.37-8.43 (m, 1H), 7.88-8.04 (m, 2H), 7.71-7.76 (m, 1H), 7.64 (s, 4H), 2.06-2.36 (m, 4H), 1.84-2.00 (m, 1H), 1.32-1.54 (m, 4H), 1.01-1.21 (m, 4H); MS (ESI$^+$) M/Z 408 (M+H)$^+$.

Example 114

2-(4-chloro-3-fluorophenyl)-N-[4-(4-chlorophenyl)-1-oxophthalazin-2(1H)-yl]acetamide The product from Example 86A and 2-(4-chloro-3-fluorophenyl)acetyl chloride were treated using a method similar to that described in Example 1C to give the title compound. $^1$H NMR (300 MHz, DMSO-d$_6$) δ ppm 11.70-11.79 (m, 1H), 8.39-8.44 (m, 1H), 7.88-8.05 (m, 2H), 7.71-7.76 (m, 1H), 7.63 (s, 4H), 7.57 (t, J=8.1 Hz, 1H), 7.44 (dd, J=10.5, 1.9 Hz, 1H), 7.25 (dd, J=8.3, 1.9 Hz, 1H), 3.75 (s, 2H); MS (ESI$^+$) M/Z 442 (M+H)$^+$.

Example 115

N-[4-(4-chlorophenyl)-1-oxophthalazin-2(1H)-yl]-2-[(1S,2S,5S)-6,6-dimethylbicyclo[3.1.1]hept-2-yl]acetamide The product of Example 86A and 2-[(1S,2S,5S)-6,6-dimethylbicyclo[3.1.1]hept-2-yl]acetic acid (Eigenmann, G. W.; Arnold, R. T. JACS 1959, 81, 3440-2) were processed using a method similar to that described in Example 17C to afford the title compound. $^1$H NMR (400 MHz, DMSO-d$_6$) δ ppm 11.38-11.39 (bs, 1H), 8.39-8.42 (m, 1H), 7.90-8.03 (m, 2H), 7.70-7.75 (m, 1H), 7.61-7.67 (m, 4H), 2.20-2.43 (m, 3H), 1.73-2.06 (m, 6H), 1.36-1.69 (m, 1H), 1.20 (s, 3H), 1.07 (s, 3H), 0.91 (d, J=9.5 Hz, 1H); MS (ESI$^+$) m/z 436 (M+H)$^+$.

Example 116

2-(adamantan-1-yl)-N-[4-(4-chlorophenyl)-1-oxophthalazin-2(1H)-yl]acetamide

The product of Example 86A and 2-(adamantan-1-yl)acetic acid were processed using a method similar to that described in Example 17C to afford the title compound. $^1$H NMR (400 MHz, DMSO-d$_6$) δ ppm 11.18-11.35 (bs, 1H), 8.39-8.42 (m, 1H), 7.89-8.02 (m, 2H), 7.70-7.73 (m, 1H), 7.56-7.68 (m, 4H), 2.04 (s, 2H), 1.92-1.95 (m, 3H), 1.66-1.69 (m, 6H), 1.63-1.70 (m, 3H), 1.57-1.62 (m, 3H); MS (ESI$^+$) m/z 448 (M+H)$^+$.

Example 117

2-(4-chlorophenyl)-N-[4-(4-chlorophenyl)-1-oxophthalazin-2(1H)-yl]acetamide

The product of Example 86A and 2-(4-chlorophenyl)acetic acid were processed using a method similar to that described in Example 17C to afford the title compound. $^1$H NMR (400 MHz, DMSO-d$_6$) δ ppm 11.63-11.81 (bs, 1H), 8.39-8.42 (m, 1H), 7.90-8.03 (m, 2H), 7.69-7.76 (m, 1H), 7.60-7.66 (m, 4H), 7.34-7.46 (m, 4H), 3.71 (s, 2H); MS (ESI$^+$) m/z 424 (M+H)$^+$.

Example 118

N-[4-(4-chlorophenyl)-1-oxophthalazin-2(1H)-yl]-2-(3,5-difluorophenyl)acetamide

The product of Example 86A and 2-(3,5-difluorophenyl)acetic acid were processed using a method similar to that described in Example 17C to afford the title compound. $^1$H NMR (400 MHz, DMSO-d$_6$) δ ppm 11.77-11.78 (bs, 1H), 8.39-8.42 (m, 1H), 7.89-8.03 (m, 2H), 7.69-7.74 (m, 1H), 7.60-7.65 (m, 4H), 7.06-7.20 (m, 3H), 3.76 (s, 2H); MS (ESI$^+$) m/z 426 (M+H)$^+$.

Example 119

N-[4-(4-chlorophenyl)-1-oxophthalazin-2(1H)-yl]-2-(1-phenylcyclopentyl)acetamide The product from Example 86A and 1-phenylcyclopentanecarboxylic acid were treated using a method similar to that described in Example 39 to give the title compound. $^1$H NMR (300 MHz, DMSO-d$_6$) δ ppm 11.22 (s, 1H), 8.36-8.40 (m, 1H), 7.86-8.03 (m, 2H), 7.68-7.76 (m, 1H), 7.62-7.67 (m, 2H), 7.56-7.61 (m, 2H), 7.34-7.41 (m, 2H), 7.22-7.28 (m, 2H), 7.10-7.18 (m, 1H), 2.64 (s, 2H), 2.08-2.32 (m, 2H), 1.87-2.04 (m, 2H), 1.69-1.83 (m, 2H), 1.49-1.66 (m, 2H); MS (ESI$^+$) M/Z 458 (M+H)$^+$.

Example 120 trans-N-[4-(4-chlorophenyl)-1-oxophthalazin-2(1H)-yl]-2-phenylcyclopropanecarboxamide The product from Example 86A and trans-2-phenyl-1-cyclopropanecarbonyl chloride were treated using a method similar to that described in Example 53 to give the title compound. $^1$H NMR (300 MHz, DMSO-d$_6$) δ ppm 11.69 (s, 1H), 8.39-8.43 (m, 1H), 7.88-8.06 (m, 2H), 7.68-7.82 (m, 1H), 7.64 (s, 4H), 7.28-7.36 (m, 2H), 7.18-7.25 (m, 3H), 2.36-2.45 (m, 1H), 2.05-2.14 (m, 1H), 1.37-1.56 (m, 2H); MS (ESI$^+$) M/Z 416 (M+H)$^+$.

Example 121

N-[4-(4-chlorophenyl)-1-oxophthalazin-2(1H)-yl]-2-(2-naphthyl)acetamide

The product from Example 86A and 2-(2-naphthyl)acetic acid were treated using a method similar to that described in Example 57 to give the title compound. $^1$H NMR (500 MHz, DMSO-d$_6$/Deuterium Oxide) δ ppm 8.41-8.43 (m, 1H), 7.96-8.04 (m, 2H), 7.86-7.94 (m, 4H), 7.72-7.75 (m, 1H), 7.61-7.66 (m, 4H), 7.50-7.57 (m, 3H), 3.88 (s, 2H); MS (APCI$^+$) M/Z 440 (M+H)$^+$.

Example 122

N-[4-(4-chlorophenyl)-1-oxophthalazin-2(1H)-yl]-2-(1-naphthyl)acetamide

The product from Example 86A and 2-(1-naphthyl)acetic acid were treated using a method similar to that described in Example 57 to give the title compound. $^1$H NMR (500 MHz, DMSO-d$_6$/Deuterium Oxide) δ ppm 8.40-8.43 (m, 1H), 8.18 (d, J=8.2 Hz, 1H), 7.95-8.01 (m, 3H), 7.88 (d, J=8.1 Hz, 1H), 7.70-7.77 (m, 1H), 7.61-7.66 (m, 4H), 7.54-7.60 (m, 3H), 7.51 (dd, J=8.2, 7.1 Hz, 1H), 4.19 (s, 2H); MS (ESI$^-$) M/Z 438 (M–H)$^-$.

Example 123

N-[4-(4-chlorophenyl)-1-oxophthalazin-2(1H)-yl]-4,4,4-trifluorobutanamide

The product from Example 86A and 4,4,4-trifluorobutanoic acid were treated using a method similar to that described in Example 57 to give the title compound. $^1$H NMR (500 MHz, DMSO-d$_6$/Deuterium Oxide) δ ppm 8.40-8.43 (m, 1H), 7.89-8.05 (m, 2H), 7.73-7.75 (m, 1H), 7.60-7.70 (m, 4H), 2.58-2.71 (m, 4H); MS (ESI$^-$) M/Z 394 (M–H)$^-$.

Example 124

N-[4-(4-chlorophenyl)-1-oxophthalazin-2(1H)-yl]-3,3,3-trifluoropropanamide

The product from Example 86A and 4,4,4-trifluoropropanoic acid were treated using a method similar to that described in Example 57 to give the title compound. $^1$H NMR (500 MHz, DMSO-d$_6$/Deuterium Oxide) δ ppm 8.41-8.45 (m, 1H), 7.96-8.03 (m, 2H), 7.72-7.76 (m, 1H), 7.63-7.66 (m, 4H), 3.60 (q, J=11.0 Hz, 2H); MS (ESI$^-$) M/Z 380 (M–H)$^-$.

Example 125

(±)-2-(exo-bicyclo[2.2.1]hept-2-yl)-N-[4-(3-chlorophenyl)-1-oxophthalazin-2(1H)-yl]acetamide Example 125A 2-amino-4-(3-chlorophenyl)phthalazin-1(2H)-one 4-(3-Chlorophenyl)phthalazin-1(2H)-one was processed using the method described in Example 1B to afford the title compound. MS (ESI) m/z 272 (M+H)$^+$.

Example 125B (±)-2-(exo-bicyclo[2.2.1]hept-2-yl)-N-[4-(3-chlorophenyl)-1-oxophthalazin-2(1H)-yl]acetamide The product of Example 125A and (±)-2-(exo-bicyclo[2.2.1]hept-2-yl)acetyl chloride were processed using a method similar to that described Example 1C, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to afford the title compound. $^1$H NMR (400 MHz, DMSO-d$_6$) δ ppm 11.36 (s, 1H), 8.39-8.42 (m, 1H), 7.90-8.04 (m, 2H), 7.70-7.74 (m, 1H), 7.56-7.68 (m, 4H), 2.07-2.34 (m, 4H), 1.87-1.91 (m, 1H), 1.33-1.57 (m, 4H), 1.06-1.23 (m, 4H); MS (ESI$^+$) m/z 408 (M+H)$^+$.

Example 126

2-(adamantan-1-yl)-N-[4-(3-chlorophenyl)-1-oxophthalazin-2(1H)-yl]acetamide

The product of Example 125A and 2-(adamantan-1-yl)acetic acid were processed using a method similar to that described in Example 17C to afford the title compound. $^1$H NMR (400 MHz, DMSO) δ 11.29 (s, 1H), 8.46-8.39 (m, 1H), 8.02-7.92 (m, 2H), 7.76-7.69 (m, 1H), 7.68-7.54 (m, 4H), 2.06 (s, 2H), 1.95 (s, 3H), 1.74-1.51 (m, 12H); MS (APCI) m/z 448 (M+H)$^+$.

Example 127

2-(4-chlorophenyl)-N-[4-(3-chlorophenyl)-1-oxophthalazin-2(1H)-yl]acetamide

The product of Example 125A and 2-(4-chlorophenyl)acetic acid were processed using a method similar to that described in Example 17C to afford the title compound. $^1$H NMR (400 MHz, DMSO-d$_6$) δ ppm 11.74 (s, 1H), 8.39-8.42 (m, 1H), 7.90-8.05 (m, 2H), 7.68-7.74 (m, 1H), 7.55-7.67 (m, 4H), 7.35-7.46 (m, 4H), 3.71 (s, 2H); MS (ESI+) m/z 424 (M+H)$^+$.

Example 128

N-[4-(3-chlorophenyl)-1-oxophthalazin-2(1H)-yl]-2-(3,5-difluorophenyl)acetamide

The product of Example 125A and 2-(3,5-difluorophenyl)acetic acid were processed using a method similar to that described in Example 17C to afford the title compound. $^1$H NMR (400 MHz, DMSO-d$_6$) δ ppm 11.79 (s, 1H), 8.40-8.43 (m, 1H), 7.91-8.05 (m, 2H), 7.71-7.75 (m, 1H), 7.63-7.68 (m, 2H), 7.56-7.63 (m, 2H), 7.07-7.22 (m, 3H), 3.78 (s, 2H); MS (ESI+) m/z 426 (M+H)$^+$.

Example 129

2-[(1S,2S,4R)-bicyclo[2.2.1]hept-2-yl]-N-[4-(4-fluorophenyl)-1-oxophthalazin-2(1H)-yl]acetamide Example 129A 2-amino-4-(4-fluorophenyl)phthalazin-1(2H)-one 2-(4-Fluorobenzoyl)benzoic acid was treated with hydrazine hydrate using a method similar to that described in Example 1A, the product obtained and with O-(diphenylphosphoryl)hydroxylamine using a method similar to that described in Example 1B to give the title compound. MS (APCI$^+$) M/Z 256 (M+H)$^+$.

Example 129B

2-[(1S,2S,4R)-bicyclo[2.2.1]hept-2-yl]-N-[4-(4-fluorophenyl)-1-oxophthalazin-2(1H)-yl]acetamide The product of Example 130 was treated with hydrogen similar to that described in Example 66 to give the title compound. $^1$H NMR (400 MHz, DMSO-d$_6$) δ ppm 11.33 (s, 1H), 8.38-8.41 (m, 1H), 7.89-8.03 (m, 2H), 7.70-7.73 (m, 1H), 7.62-7.68 (m, 2H), 7.35-7.48 (m, 2H), 2.29-2.39 (m, 2H), 2.20-2.29 (m, 1H), 2.14-2.22 (m, 2H), 1.72-1.81 (m, 1H), 1.53-1.62 (m, 1H), 1.44-1.53 (m, 1H), 1.29-1.41 (m, 2H), 1.23-1.29 (m, 1H), 1.09-1.18 (m, 1H), 0.75 (ddd, J=12.1, 4.9, 2.5 Hz, 1H); MS (APCI$^+$) M/Z 392 (M+H)$^+$.

Example 130

2-[(1S,2S,4S)-bicyclo[2.2.1]hept-5-en-2-yl]-N-[4-(4-fluorophenyl)-1-oxophthalazin-2(1H)-yl]acetamide The product of Example 129A and 2-[(1S,2S,4S)-bicyclo[2.2.1]hept-5-en-2-yl]acetic acid were treated using a method similar to that described in Example 17C to give the title compound. ¹H NMR (400 MHz, DMSO-d$_6$) δ 11.29 (s, 1H), 8.43-8.37 (m, 1H), 8.05-7.88 (m, 2H), 7.76-7.68 (m, 1H), 7.70-7.61 (m, 2H), 7.48-7.34 (m, 2H), 6.22 (dd, J=5.7, 2.9, 1H), 6.06 (dd, J=5.7, 2.8, 1H), 2.92-2.86 (m, 1H), 2.81-2.75 (m, 1H), 2.42-2.48 (m, buried), 2.19-1.98 (m, 2H), 1.90 (ddd, J=11.6, 9.0, 3.8, 1H), 1.39-1.30 (m, 1H), 1.30-1.22 (m, 1H), 0.60 (ddd, J=11.6, 4.2, 2.6, 1H); MS (APCI⁺) M/Z 390 (M+H)⁺.

Example 131

(±)-2-(exo-bicyclo[2.2.1]hept-2-yl)-N-[4-(4-fluorophenyl)-1-oxophthalazin-2(1H)-yl]acetamide The product of Example 129A and the product from Example 58A were treated using a method similar to that described in Example 1C to give the title compound. ¹H NMR (400 MHz, DMSO) δ 11.34 (s, 1H), 8.43-8.37 (m, 1H), 8.04-7.88 (m, 2H), 7.75-7.68 (m, 1H), 7.69-7.61 (m, 2H), 7.48-7.34 (m, 2H), 2.27 (dd, J=14.1, 8.3, 1H), 2.23-2.17 (m, 1H), 2.20-2.08 (m, 2H), 1.95-1.83 (m, 1H), 1.56-1.39 (m, 3H), 1.43-1.33 (m, 1H), 1.22-1.06 (m, 4H); MS (APCI⁺) M/Z 392 (M+H)⁺.

Example 132

2-(4-chlorophenyl)-N-[4-(4-fluorophenyl)-1-oxophthalazin-2(1H)-yl]acetamide

The product of Example 129A and 2-(4-chlorophenyl)acetic acid were treated using a method similar to that described in Example 17C to give the title compound. ¹H NMR (400 MHz, DMSO-d$_6$) δ ppm 11.71-11.73 (bs, 1H), 8.39-8.45 (m, 1H), 7.90-8.03 (m, 2H), 7.69-7.74 (m, 1H), 7.62-7.68 (m, 2H), 7.37-7.44 (m, 6H), 3.71 (s, 2H); MS (APCI⁺) M/Z 408 (M+H)⁺.

Example 133

2-(3,5-difluorophenyl)-N-[4-(4-fluorophenyl)-1-oxophthalazin-2(1H)-yl]acetamide

The product of Example 129A and 2-(3,5-difluorophenyl) acetic acid were treated using a method similar to that described in Example 17C to give the title compound. ¹H NMR (400 MHz, DMSO-d$_6$) δ ppm 11.77-11.79 (bs, 1H), 8.40-8.43 (m, 1H), 7.90-8.03 (m, 2H), 7.69-7.74 (m, 1H), 7.63-7.69 (m, 2H), 7.38-7.43 (m, 2H), 7.06-7.21 (m, 3H), 3.77-3.78 (bs, 2H); MS (APCI⁺) M/Z 410 (M+H)⁺.

Example 134

(±)-2-(exo-bicyclo[2.2.1]hept-2-yl)-N-[4-(2,4-difluorophenyl)-1-oxophthalazin-2(1H)-yl]acetamide Example 134A 2-amino-4-(2,4-difluorophenyl)phthalazin-1(2H)-one 4-Chlorophthalazin-1(2H)-one and 2,4-difluorophenylboronic acid were treated using a method similar to that described in Example 81A to give 4-(2,4-difluorophenyl) phthalazin-1(2H)-one, which was then treated with O-(diphenylphosphoryl)hydroxylamine using a method similar to that described in Example 1B to give the title compound. MS (APCI⁺) M/Z 274 (M+H)⁺.

Example 134B (±)-2-(exo-bicyclo[2.2.1]hept-2-yl)-N-[4-(2,4-difluorophenyl)-1-oxophthalazin-2(1H)-yl]acetamide The product of Example 134A and the product from Example 58A were treated using a method similar to that described in Example 1C to give the title compound. ¹H NMR (400 MHz, DMSO-d$_6$) δ ppm 11.25-11.49 (bs, 1H), 8.37-8.42 (m, 1H), 7.90-8.02 (m, 2H), 7.64 (td, J=8.5, 6.5 Hz, 1H), 7.44-7.57 (m, 2H), 7.32 (tdd, J=8.4, 2.6, 0.9 Hz, 1H), 2.26 (dd, J=14.2, 8.2 Hz, 1H), 2.18-2.22 (m, 1H), 2.14 (dd, J=14.4, 7.6 Hz, 1H), 2.09-2.11 (m, 1H), 1.84-1.94 (m, 1H), 1.41-1.54 (m, 3H), 1.34-1.40 (m, 1H), 1.07-1.20 (m, 4H); MS (APCI⁺) M/Z 410 (M+H)⁺.

Example 135

2-(4-chlorophenyl)-N-[4-(4-methylphenyl)-1-oxophthalazin-2(1H)-yl]acetamide

Example 135A 2-amino-4-(4-methylphenyl)-phthalazin-1(2H)-one 4-(4-methylphenyl)-phthalazin-1(2H)-one was treated with O-(diphenylphosphoryl)hydroxylamine using a method similar to that described in Example 1B to give the title compound. MS (APCI⁺) M/Z 252 (M+H)⁺.

Example 135B 2-(4-chlorophenyl)-N-[4-(4-methylphenyl)-1-oxophthalazin-2(1H)-yl]acetamide The product of Example 135A and 2-(4-chlorophenyl)acetic acid were treated using a method similar to that described in Example 17C to give the title compound. ¹H NMR (400 MHz, DMSO-d$_6$) δ ppm 11.71 (s, 1H), 8.38-8.41 (m, 1H), 7.89-8.02 (m, 2H), 7.72-7.75 (m, 1H), 7.46-7.49 (m, 2H), 7.38-7.44 (m, 4H), 7.36-7.40 (m, 2H), 3.70 (s, 2H), 2.41 (s, 3H); MS (APCI⁺) M/Z 404 (M+H)⁺.

Example 136

2-(3,5-difluorophenyl)-N-[4-(4-methylphenyl)-1-oxophthalazin-2(1H)-yl]acetamide

The product of Example 135A and 2-(3,5-difluorophenyl) acetic acid were treated as in Example 17C to give the title compound. ¹H NMR (400 MHz, DMSO-d$_6$) δ ppm 11.75 (s, 1H), 8.39-8.42 (m, 1H), 7.89-8.03 (m, 2H), 7.73-7.76 (m, 1H), 7.47-7.50 (m, 2H), 7.37-7.40 (m, 2H), 7.09-7.22 (m, 3H), 3.77 (s, 2H), 2.42 (s, 3H); MS (APCI⁺) M/Z 406 (M+H)⁺.

Example 137

2-[(1S,2S,5S)-6,6-dimethylbicyclo[3.1.1]hept-2-yl]-N-[4-(4-methylphenyl)-1-oxophthalazin-2(1H)-yl] acetamide The product of Example 135A and 2-[(1S,2S,5S)-6,6-dimethylbicyclo[3.1.1]hept-2-yl]acetic acid were treated using a method similar to that described in Example 17C to give the title compound. ¹H NMR (300 MHz, DMSO-d$_6$) δ ppm 11.34 (s, 1H), 8.37-8.41 (m, 1H), 7.86-8.04 (m, 2H), 7.72-7.77 (m, 1H), 7.46-7.50 (m, 2H), 7.36-7.40 (m, 2H), 2.51-2.60 (m, 2H), 2.42 (s, 3H), 2.29-2.45 (m, 2H), 1.79-2.06 (m, 5H), 1.47-1.63 (m, 1H), 1.20 (s, 3H), 1.07 (d, J=0.6 Hz, 3H), 0.91 (d, J=9.5 Hz, 1H); MS (APCI$^+$) M/Z 416 (M+H)$^+$.

Example 138

2-(adamantan-1-yl)-N-[4-(4-methylphenyl)-1-oxophthalazin-2(1H)-yl]acetamide

The product of Example 135A and 2-(adamantan-1-yl) acetic acid were treated using a method similar to that described in Example 17C to give the title compound. $^1$H NMR (400 MHz, DMSO-d$_6$) δ ppm 11.24 (s, 1H), 8.39-8.42 (m, 1H), 7.88-8.02 (m, 2H), 7.73-7.76 (m, 1H), 7.47-7.50 (m, 2H), 7.37-7.40 (m, 2H), 2.42 (s, 3H), 2.05 (s, 2H), 1.94-1.99 (m, 3H), 1.65-1.73 (m, 9H), 1.57-1.64 (m, 3H); MS (APCI$^+$) M/Z 428 (M+H)$^+$.

Example 139

N-(4-benzyl-1-oxophthalazin-2(1H)-yl)-2-[1-(trifluoromethyl)cyclopentyl]acetamide Example 139A 2-amino-4-benzylphthalazin-1(2H)-one 2-(2-phenylacetyl)benzoic acid was treated using methods similar to that described in Examples 11A and 11B to give the title compound. MS (APCI+) M/Z 253 (M+H)+.

Example 139B

N-(4-benzyl-1-oxophthalazin-2(1H)-yl)-2-[1-(trifluoromethyl)cyclopentyl]acetamide The product of Example 139A and 1-(trifluoromethyl)cyclopentanecarboxylic acid were treated using a method similar to that described in Example 87 to give the title compound. $^1$H NMR (300 MHz, DMSO-d$_6$) δ ppm 11.60 (s, 1H), 8.30-8.34 (m, 1H), 7.96-8.03 (m, 1H), 7.92 (ddd, J=7.9, 7.1, 1.6 Hz, 1H), 7.86 (ddd, J=7.8, 7.1, 1.5 Hz, 1H), 7.25-7.36 (m, 4H), 7.15-7.24 (m, 1H), 4.31 (s, 2H), 2.59 (s, 2H), 2.08-2.32 (m, 2H), 1.80-1.91 (m, 2H), 1.51-1.79 (m, 4H); MS (ESI$^-$) M/Z 428 (M−H)$^-$.

Example 140

N-(4-benzyl-1-oxophthalazin-2(1H)-yl)-3-methyl-3-phenylbutanamide

The product of Example 139A and 3-methyl-3-phenylbutanoic acid were treated using a method similar to that described in Example 17C to give the title compound. $^1$H NMR (400 MHz, DMSO-d$_6$) δ ppm 11.31 (s, 1H), 8.31 (dd, J=7.8, 1.4 Hz, 1H), 7.96-8.01 (m, 1H), 7.90 (ddd, J=8.0, 7.2, 1.5 Hz, 1H), 7.85 (ddd, J=7.8, 7.2, 1.4 Hz, 1H), 7.44-7.47 (m, 2H), 7.25-7.35 (m, 6H), 7.17-7.23 (m, 2H), 4.30-4.30 (bs, 2H), 2.61 (s, 2H), 1.48 (s, 6H); LC/MS (APCI) M/Z 412 (M+H)$^+$.

Example 141

(±)-N-(4-benzyl-1-oxophthalazin-2(1H)-yl)-2-(exo-bicyclo[2.2.1]hept-2-yl)acetamide The product of Example 139A and the product of Example 58A were treated using a method similar to that described in Example 1C to give the title compound. $^1$H NMR (400 MHz, DMSO-d$_6$) δ ppm 11.26 (s, 1H), 8.30 (dd, J=7.8, 1.5 Hz, 1H), 7.96-7.99 (m, 1H), 7.90 (ddd, J=8.0, 7.2, 1.5 Hz, 1H), 7.85 (ddd, J=7.8, 7.1, 1.4 Hz, 1H), 7.24-7.37 (m, 4H), 7.17-7.22 (m, 1H), 4.31-4.31 (bs, 2H), 2.26 (dd, J=14.3, 8.3 Hz, 1H), 2.19-2.23 (m, 1H), 2.14 (dd, J=14.3, 7.2 Hz, 1H), 2.11-2.14 (m, 1H), 1.86-1.94 (m, 1H), 1.34-1.58 (m, 4H), 1.02-1.23 (m, 4H); LC/MS (APCI) M/Z 388 (M+H)$^+$.

Example 142

N-(4-benzyl-1-oxophthalazin-2(1H)-yl)-2-(4-chlorophenyl)acetamide

The product of Example 139A and 2-(4-chlorophenyl)acetic acid were treated using a method similar to that described in Example 17C to give the title compound. $^1$H NMR (400 MHz, DMSO-d$_6$) δ ppm 11.64 (s, 1H), 8.30 (dd, J=7.8, 1.5 Hz, 1H), 7.96-7.99 (m, 1H), 7.91 (ddd, J=8.0, 7.2, 1.5 Hz, 1H), 7.85 (ddd, J=7.8, 7.2, 1.4 Hz, 1H), 7.35-7.47 (m, 4H), 7.25-7.33 (m, 4H), 7.16-7.23 (m, 1H), 4.31-4.32 (bs, 2H), 3.71 (s, 2H); LC/MS (APCI) M/Z 404 (M+H)$^+$.

Example 143

N-(4-benzyl-1-oxophthalazin-2(1H)-yl)-2-(3,5-difluorophenyl)acetamide

The product of Example 139A and 2-(3,5-difluorophenyl) acetic acid were treated using a method similar to that described in Example 17C to give the title compound. $^1$H NMR (400 MHz, DMSO-d$_6$) δ ppm 11.66-11.72 (bs, 1H), 8.32 (dd, J=7.8, 1.5 Hz, 1H), 7.97-8.00 (m, 1H), 7.92 (ddd, J=8.0, 7.2, 1.5 Hz, 1H), 7.86 (ddd, J=7.8, 7.1, 1.3 Hz, 1H), 7.24-7.37 (m, 4H), 7.11-7.23 (m, 4H), 4.32-4.32 (bs, 2H), 3.77 (s, 2H); LC/MS (APCI) M/Z 406 (M+H)$^+$.

Example 144

(±)-2-(exo-bicyclo[2.2.1]hept-2-yl)-N-[4-(4-chlorobenzyl)-1-oxophthalazin-2(1H)-yl]acetamide Example 144A 2-amino-4-(4-chlorobenzyl)-phthalazin-1(2H)-one A solution of (4-chlorobenzyl)zinc(II) chloride in THF was added to a suspension of 4-chlorophthalazin-1(2H)-one and Pd(PPh$_3$)$_4$ in THF, and subjected to microwave conditions at 180° C. for 20 minutes. The mixture was diluted with EtOAc, washed with saturated aqueous NaHCO$_3$ and brine, dried (Na$_2$SO$_4$), filtered, and concentrated to give crude 4-(4-chlorobenzyl)phthalazin-1(2H)-one. This material was treated with O-(diphenylphosphoryl)hydroxylamine similar to that described in Example 1B to give the title compound. LC/MS (APCI) M/Z 286 (M+H)$^+$.

Example 144B (±)-2-(exo-bicyclo[2.2.1]hept-2-yl)-N-[4-(4-chlorobenzyl)-1-oxophthalazin-2(1H)-yl]acetamide The product of Example 144A and the product of Example 58A were treated using a method similar to that described in Example 1C to give the title compound. $^1$H NMR (400 MHz, DMSO-d$_6$) δ ppm 11.25 (s, 1H), 8.31 (dd, J=7.8, 1.4 Hz, 1H), 7.96 (d, J=1.3 Hz, 1H), 7.92 (ddd, J=7.9, 7.1, 1.4 Hz, 1H), 7.87 (ddd, J=7.8, 7.1, 1.4 Hz, 1H), 7.32-7.35 (m, 4H), 4.32 (s, 2H), 2.25 (dd, J=14.2, 8.4 Hz, 1H), 2.20-2.23 (m, 1H), 2.13 (dd, J=14.3, 7.3 Hz, 1H), 2.10-2.13 (m, 1H), 1.83-1.94 (m, 1H), 1.41-1.56 (m, 3H), 1.35-1.40 (m, 1H), 1.07-1.21 (m, 4H); LC/MS (APCI) M/Z 422 (M+H)$^+$.

Example 145

N-[4-(4-chlorobenzyl)-1-oxophthalazin-2(1H)-yl]-2-(4-chlorophenyl)acetamide

The product of Example 144A and 2-(4-chlorophenyl)acetic acid were treated using a method similar to that described in Example 17C to give the title compound. $^1$H NMR (400 MHz, DMSO-d$_6$) δ ppm 11.63 (s, 1H), 8.30 (d, J=8.3 Hz, 1H), 7.95-7.99 (m, 1H), 7.90-7.95 (m, 1H), 7.84-7.89 (m, 1H), 7.37-7.44 (m, 4H), 7.31-7.38 (m, 4H), 4.32-4.32 (bs, 2H), 3.70 (s, 2H); LC/MS (APCI) M/Z 438 (M+H)$^+$.

Example 146

N-[4-(4-chlorobenzyl)-1-oxophthalazin-2(1H)-yl]-2-(3,5-difluorophenyl)acetamide

The product of Example 144A and 2-(3,5-difluorophenyl)acetic acid were treated using a method similar to that described in Example 17C to give the title compound. $^1$H NMR (500 MHz, DMSO-d$_6$) δ ppm 11.68 (s, 1H), 8.32 (dd, J=7.9, 1.4 Hz, 1H), 7.98 (d, J=7.9 Hz, 1H), 7.91-7.95 (m, 1H), 7.85-7.89 (m, 1H), 7.32-7.38 (m, 4H), 7.11-7.19 (m, 3H), 4.33 (s, 2H), 3.76 (s, 2H); LC/MS (APCI) M/Z 440 (M+H)$^+$.

Example 147

2-[(1S,2S,4R)-bicyclo[2.2.1]hept-2-yl]-N-{1-oxo-4-[4-(trifluoromethyl)phenyl]phthalazin-2(1H)-yl}acetamide

Example 147A 2-amino-4-[4-(trifluoromethyl)phenyl]phthalazin-1(2H)-one

4-Chlorophthalazin-1(2H)-one and 4-(trifluoromethyl)phenylboronic acid were treated using a method similar to that described in Example 81A to give 4-[4-(trifluoromethyl)phenyl]phthalazin-1(2H)-one, which was then treated with O-(diphenylphosphoryl)hydroxylamine using a method similar to that described in Example 1B to give the title compound. MS (APCI$^+$) M/Z 306 (M+H)$^+$.

Example 147B

2-[(1S,2S,4R)-bicyclo[2.2.1]hept-2-yl]-N-{1-oxo-4-[4-(trifluoromethyl)phenyl]phthalazin-2(1H)-yl}acetamide The product of Example 147A and 2-[(1S,2S,4S)-bicyclo[2.2.1]hept-5-en-2-yl]acetic acid were treated using a method similar to that described in Example 17C, followed by treatment with hydrogen similar to that described in Example 66 to give the title compound. $^1$H NMR (400 MHz, DMSO) δ 11.41-11.35 (m, 1H), 8.45-8.38 (m, 1H), 8.01-7.91 (m, 4H), 7.88-7.81 (m, 2H), 7.76-7.70 (m, 1H), 2.37-2.30 (m, 2H), 2.28-2.22 (m, 1H), 2.22-2.13 (m, 2H), 1.82-1.72 (m, 1H), 1.62-1.43 (m, 2H), 1.39-1.29 (m, 2H), 1.29-1.21 (m, 1H), 1.19-1.08 (m, 1H), 0.79-0.70 (m, 1H); MS (DCI$^+$) M/Z 459 (M+NH$_4$)$^+$.

Example 148

3-methyl-N-{1-oxo-4-[4-(trifluoromethyl)phenyl]phthalazin-2(1H)-yl}-3-phenylbutanamide The product of Example 147A and 3-methyl-3-phenylbutanoic acid were treated using a method similar to that described in Example 17C to give the title compound. $^1$H NMR (400 MHz, DMSO-d$_6$) δ ppm 11.37-11.43 (m, 1H), 8.39-8.48 (m, 1H), 7.95-8.01 (m, 2H), 7.94-7.97 (m, 2H), 7.82-7.85 (m, 2H), 7.71-7.75 (m, 1H), 7.43-7.46 (m, 2H), 7.29-7.33 (m, 2H), 7.15-7.21 (m, 1H), 2.63 (s, 2H), 1.47 (s, 6H); MS (APCI$^+$) M/Z 466 (M+H)$^+$.

Example 149

2-(adamantan-1-yl)-N-{1-oxo-4-[4-(trifluoromethyl)phenyl]phthalazin-2(1H)-yl}acetamide The product of Example 147A and 2-(adamantan-1-yl)acetyl chloride were treated using a method similar to that described in Example 1C to give the title compound. $^1$H NMR (400 MHz, DMSO-d$_6$) δ ppm 11.31 (s, 1H), 8.42-8.45 (m, 1H), 7.96-8.01 (m, 2H), 7.93-7.97 (m, 2H), 7.83-7.86 (m, 2H), 7.72-7.76 (m, 1H), 2.06 (s, 2H), 1.93-1.96 (m, 3H), 1.58-1.73 (m, 12H); MS (APCI$^+$) M/Z 482 (M+H)$^+$.

Example 150

(±)-2-(exo-bicyclo[2.2.1]hept-2-yl)-N-{1-oxo-4-[4-(trifluoromethyl)phenyl]phthalazin-2(1H)-yl}acetamide The product of Example 147A and the product of Example 58A were treated using a method similar to that in Example 1C to give the title compound. $^1$H NMR (400 MHz, DMSO-d$_6$) δ ppm 11.39 (s, 1H), 8.41-8.45 (m, 1H), 7.97-8.01 (m, 2H), 7.93-7.97 (m, 2H), 7.83-7.86 (m, 2H), 7.72-7.76 (m, 1H), 2.28 (dd, J=14.2, 8.4 Hz, 1H), 2.19-2.23 (m, 1H), 2.16 (dd, J=14.3, 7.5 Hz, 1H), 2.10-2.13 (m, 1H), 1.85-1.94 (m, 1H), 1.42-1.54 (m, 3H), 1.35-1.41 (m, 1H), 1.08-1.21 (m, 4H); MS (APCI$^+$) M/Z 442 (M+H)$^+$.

Example 151

(±)-2-(exo-bicyclo[2.2.1]hept-2-yl)-N-[4-(4-methoxyphenyl)-1-oxophthalazin-2(1H)-yl]acetamide

Example 151A 2-amino-4-(4-methoxyphenyl)phthalazin-1(2H)-one 4-(4-methoxyphenyl)phthalazin-1(2H)-one was treated as in Example 1B to give the title compound. MS (APCI$^+$) M/Z 268 (M+H)$^+$.

Example 151B (±)-2-(exo-bicyclo[2.2.1]hept-2-yl)-N-[4-(4-methoxyphenyl)-1-oxophthalazin-2(1H)-yl]acetamide A mixture of the product from Example 151A, O-(7-azabenzotriazol-1-yl)-N,N,N',N'-tetramethyluronium hexafluorophosphate (HATU), triethylamine, and (±)-2-(exo-bicyclo[2.2.1]heptan-2-yl)acetic acid in DMF was stirred overnight, heated at 80° C. for 4 hours, diluted with EtOAc, washed with 0.5N NaOH and brine, dried ($Na_2SO_4$), filtered, and purified by preparative HPLC [Phenomenex Luna C8(2) 5 um 100 Å AXIA column (30 mm×75 mm); a gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A)] to give the title compound.: $^1H$ NMR (300 MHz, DMSO-$d_6$) δ ppm 11.29 (s, 1H), 8.37-8.41 (m, 1H), 7.86-8.04 (m, 2H), 7.74-7.80 (m, 1H), 7.51-7.55 (m, 2H), 7.11-7.14 (m, 2H), 3.85 (s, 3H), 2.10-2.32 (m, 4H), 1.84-1.94 (m, 1H), 1.32-1.53 (m, 4H), 1.04-1.21 (m, 4H); MS ($ESI^+$) M/Z 404 (M+H)$^+$.

Example 152

N-[4-(4-methoxyphenyl)-1-oxophthalazin-2(1H)-yl]-2-(4-methylcyclohexyl)acetamide The product from Example 151A and 2-(4-methylcyclohexyl)acetic acid were treated using a method similar to that described in Example 5 to give the title compound. $^1H$ NMR (300 MHz, DMSO-$d_6$) δ ppm 11.31 (s, 1H), 8.37-8.44 (m, 1H), 7.86-8.04 (m, 2H), 7.74-7.80 (m, 1H), 7.51-7.55 (m, 2H), 7.10-7.14 (m, 2H), 3.85 (s, 3H), 2.23-2.34 (m, 2H), 1.95-2.09 (m, 1H), 1.77-1.88 (m, 1H), 1.42-1.72 (m, 5H), 1.20-1.35 (m, 2H), 0.88-1.06 (m, 1H), 0.92 (d, J=6.7 Hz, 3H); MS ($ESI^+$) M/Z 406 (M+H)$^+$.

Example 153

2-(3,5-difluorophenyl)-N-[4-(4-methoxyphenyl)-1-oxophthalazin-2(1H)-yl]acetamide The product from Example 151A and 2-(3,5-difluorophenyl)acetyl chloride were treated using a method similar to that described in Example 1C to give the title compound. $^1H$ NMR (300 MHz, DMSO-$d_6$) δ ppm 11.73 (s, 1H), 8.39-8.42 (m, 1H), 7.87-8.05 (m, 2H), 7.75-7.79 (m, 1H), 7.52-7.55 (m, 2H), 7.05-7.23 (m, 5H), 3.85 (s, 3H), 3.77 (s, 2H); MS (ESI+) M/Z 422 (M+H)+.

Example 154

2-(adamantan-1-yl)-N-[4-(4-methoxyphenyl)-1-oxophthalazin-2(1H)-yl]acetamide

The product from Example 151A and (adamantan-1-yl)acetyl chloride were treated using a method similar to that described in Example 1C to give the title compound. $^1H$ NMR (400 MHz, DMSO-$d_6$) δ ppm 11.23 (s, 1H), 8.39-8.42 (m, 1H), 7.88-8.02 (m, 2H), 7.75-7.78 (m, 1H), 7.52-7.55 (m, 2H), 7.11-7.14 (m, 2H), 3.85 (s, 3H), 2.05 (s, 2H), 1.94-1.97 (m, 3H), 1.59-1.70 (m, 12H); MS (ESI+) M/Z 444 (M+H)+.

Example 155

(±)-2-(exo-bicyclo[2.2.1]hept-2-yl)-N-[4-(2,5-dimethylphenyl)-1-oxophthalazin-2(1H)-yl]acetamide 4-(2,5-dimethylphenyl)phthalazin-1(2H)-one was treated using a method similar to that described in Example 1B to give 2-amino-4-(2,5-dimethylphenyl)phthalazin-1(2H)-one, which was used without purification, and treated with (±)-2-(exo-bicyclo[2.2.1]hept-2-yl)acetic acid using a method similar to that described in Example 17C to give the title compound. $^1H$ NMR (400 MHz, DMSO-$d_6$) δ ppm 11.31 (s, 1H), 8.37-8.41 (m, 1H), 7.85-8.00 (m, 2H), 7.25-7.29 (m, 3H), 7.13-7.14 (m, 1H), 2.34 (s, 3H), 2.25 (dd, J=14.2, 8.2 Hz, 1H), 2.18-2.22 (m, 1H), 2.13 (dd, J=14.3, 7.4 Hz, 1H), 2.09-2.12 (m, 1H), 2.03 (s, 3H), 1.84-1.92 (m, 1H), 1.40-1.53 (m, 3H), 1.34-1.40 (m, 1H), 1.05-1.22 (m, 4H); MS ($APCI^+$) M/Z 403 (M+H)$^+$.

Example 156

2-(adamantan-1-yl)-N-[4-(2,5-dimethylphenyl)-1-oxophthalazin-2(1H)-yl]acetamide 4-(2,5-dimethylphenyl)phthalazin-1(2H)-one was treated using a method similar to that described in Example 1B to give 2-amino-4-(2,5-dimethylphenyl)phthalazin-1(2H)-one, which was used without purification, and treated with 2-(adamantan-1-yl)acetic acid using a method similar to that described in Example 17C to give the title compound. $^1H$ NMR (400 MHz, DMSO-$d_6$) δ ppm 11.24 (s, 1H), 8.38-8.41 (m, 1H), 7.85-7.98 (m, 2H), 7.22-7.34 (m, 3H), 7.15 (s, 1H), 2.34 (s, 3H), 2.04-2.05 (m, 5H), 1.93-1.96 (m, 3H), 1.64-1.72 (m, 8H), 1.54-1.63 (m, 4H); MS ($APCI^+$) M/Z 443 (M+H)$^+$.

Example 157

2-(4-chlorophenyl)-N-[4-(2,5-dimethylphenyl)-1-oxophthalazin-2(1H)-yl]acetamide 4-(2,5-dimethylphenyl)phthalazin-1(2H)-one was treated using a method similar to that described in Example 1B to give 2-amino-4-(2,5-dimethylphenyl)phthalazin-1(2H)-one, which was used without purification, and treated with 2-(4-chlorophenyl)acetic acid using a method similar to that described in Example 17C to give the title compound. $^1H$ NMR (400 MHz, DMSO-$d_6$) δ ppm 11.57-11.82 (bs, 1H), 8.37-8.41 (m, 1H), 7.85-7.98 (m, 2H), 7.34-7.43 (m, 4H), 7.21-7.32 (m, 3H), 7.14 (s, 1H), 3.69 (s, 2H), 2.33 (s, 3H), 2.02 (s, 3H); MS ($APCI^+$) M/Z 418 (M+H)$^+$.

Example 158

2-(3,5-difluorophenyl)-N-[4-(2,5-dimethylphenyl)-1-oxophthalazin-2(1H)-yl]acetamide 4-(2,5-dimethylphenyl)phthalazin-1(2H)-one was treated using a method similar to that described in Example 1B to give 2-amino-4-(2,5-dimethylphenyl)phthalazin-1(2H)-one, which was used without purification, and treated with 2-(3,5-difluorophenyl)acetic acid using a method similar to that described in Example 17C to give the title compound. $^1H$ NMR (400 MHz, DMSO-$d_6$) δ ppm 11.58-11.89 (bs, 1H), 8.39-8.42 (m, 1H), 7.86-7.99 (m, 2H), 7.22-7.33 (m, 3H), 7.06-7.20 (m, 4H), 3.75 (s, 2H), 2.33 (s, 3H), 2.03 (s, 3H); MS ($APCI^+$) M/Z 420 (M+H)$^+$.

Example 159

2-[(1S,2S,4S)-bicyclo[2.2.1]hept-5-en-2-yl]-N-[4-(2,4-dimethylphenyl)-1-oxophthalazin-2(1H)-yl]acetamide Example 159A 2-amino-4-(2,4-dimethylphenyl)phthalazin-1(2H)-one 2-(2,4-Dimethylbenzoyl)benzoic acid was treated with hydrazine hydrate using a method similar to that described in Example 11A [MS (APCI$^+$) M/Z 251 (M+H)$^+$], followed by treatment with O-(diphenylphosphoryl)hydroxylamine using a method similar to that described in Example 1B to give the title compound.

Example 159B

2-[(1S,2S,4S)-bicyclo[2.2.1]hept-5-en-2-yl]-N-[4-(2,4-dimethylphenyl)-1-oxophthalazin-2(1H)-yl]acetamide The product of Example 159A and 2-[(1S,2S,4S)-bicyclo [2.2.1]hept-5-en-2-yl]acetic acid were treated using a method similar to that described in Example 17C to give the title compound. $^1$H NMR (400 MHz, DMSO-d$_6$) δ ppm 11.26 (s, 1H), 8.37-8.40 (m, 1H), 7.85-7.97 (m, 2H), 7.26-7.32 (m, 1H), 7.20-7.25 (m, 2H), 7.16-7.20 (m, 1H), 6.21 (dd, J=5.7, 2.9 Hz, 1H), 6.05 (dd, J=5.7, 2.9 Hz, 1H), 2.86-2.91 (m, 1H), 2.76-2.81 (m, 1H), 2.41-2.49 (m, 1H), 2.38 (s, 3H), 2.01-2.12 (m, 2H), 2.06 (s, 3H), 1.86-1.93 (m, 1H), 1.33 (dd, J=7.9, 2.5 Hz, 1H), 1.26 (d, J=8.1 Hz, 1H), 0.59 (ddd, J=11.5, 4.3, 2.5 Hz, 1H); MS (APCI$^+$) M/Z 400 (M+H)$^+$.

Example 160

(±)-2-(exo-bicyclo[2.2.1]hept-2-yl)-N-[4-(2,4-dimethylphenyl)-1-oxophthalazin-2(1H)-yl]acetamide The product of Example 159A and (±)-2-(exo-bicyclo [2.2.1]hept-2-yl)acetic acid were treated using a method similar to that described in Example 17C to give the title compound. $^1$H NMR (400 MHz, DMSO-d$_6$) δ ppm 11.31 (s, 1H), 8.37-8.40 (m, 1H), 7.85-7.97 (m, 2H), 7.26-7.31 (m, 1H), 7.20-7.25 (m, 2H), 7.14-7.20 (m, 1H), 2.38 (s, 3H), 2.25 (dd, J=14.2, 8.4 Hz, 1H), 2.18-2.21 (m, 1H), 2.12 (dd, J=14.3, 7.4 Hz, 1H), 2.08-2.12 (m, 1H), 2.05 (s, 3H), 1.84-1.90 (m, 1H), 1.40-1.54 (m, 3H), 1.34-1.40 (m, 1H), 1.04-1.22 (m, 4H); MS (APCI$^+$) M/Z 402 (M+H)$^+$.

Example 161

2-(4-chlorophenyl)-N-[4-(2,4-dimethylphenyl)-1-oxophthalazin-2(1H)-yl]acetamide

The product of Example 159A and 2-(4-chlorophenyl)acetic acid were treated using a method similar to that described in Example 17C to give the title compound. $^1$H NMR (400 MHz, DMSO-d$_6$) δ ppm 11.68 (s, 1H), 8.37-8.40 (m, 1H), 7.85-7.97 (m, 2H), 7.34-7.45 (m, 4H), 7.25-7.31 (m, 1H), 7.19-7.24 (m, 2H), 7.14-7.18 (m, 1H), 3.69 (s, 2H), 2.37 (s, 3H), 2.04 (s, 3H); MS (APCI$^+$) M/Z 418 (M+H)$^+$.

Example 162

2-(3,5-difluorophenyl)-N-[4-(2,4-dimethylphenyl)-1-oxophthalazin-2(1H)-yl]acetamide The product of Example 159A and 2-(3,5-difluorophenyl) acetic acid were treated using a method similar to that described in Example 17C to give the title compound. $^1$H NMR (400 MHz, DMSO-d$_6$) δ ppm 11.67-11.81 (bs, 1H), 8.38-8.41 (m, 1H), 7.85-7.98 (m, 2H), 7.25-7.32 (m, 1H), 7.20-7.24 (m, 2H), 7.09-7.19 (m, 4H), 3.75 (s, 2H), 2.37 (s, 3H), 2.05 (s, 3H); MS (APCI$^+$) M/Z 420 (M+H)$^+$.

Example 163

(±)-2-(exo-bicyclo[2.2.1]hept-2-yl)-N-[4-(3,4-dimethylphenyl)-1-oxophthalazin-2(1H)-yl]acetamide Example 163A 2-amino-4-(3,4-dimethylphenyl)phthalazin-1(2H)-one 2-(3,4-Dimethylbenzoyl)benzoic acid was treated with hydrazine hydrate using a method similar to that described in Example 11A, followed by treatment with O-(diphenylphosphoryl)hydroxylamine using a method similar to that described in Example 1B to give the title compound. MS (APCI$^+$) M/Z 266 (M+H)$^+$.

Example 163B (±)-2-(exo-bicyclo[2.2.1]hept-2-yl)-N-[4-(3,4-dimethylphenyl)-1-oxophthalazin-2(1H)-yl]acetamide The product of Example 163A and (±)-2-(exo-bicyclo [2.2.1]hept-2-yl)acetic acid were treated using a method similar to that described in Example 17C to give the title compound. $^1$H NMR (400 MHz, DMSO) δ 11.31 (s, 1H), 8.42-8.36 (m, 1H), 7.99-7.89 (m, 2H), 7.77-7.71 (m, 1H), 7.38-7.25 (m, 3H), 2.32 (s, 3H), 2.31 (s, 3H), 2.27 (dd, J=14.3, 8.4, 1H), 2.20 (m, 1H), 2.14 (dd, J=14.3, 7.3, 2H), 1.89 (dt, J=15.8, 7.9, 1H), 1.55-1.34 (m, 4H), 1.21-1.04 (m, 4H); MS (APCI$^+$) M/Z 402 (M+H)$^+$.

Example 164

2-(adamantan-1-yl)-N-[4-(3,4-dimethylphenyl)-1-oxophthalazin-2(1H)-yl]acetamide

The product of Example 163A and 2-(adamantan-1-yl) acetyl chloride were treated using a method similar to that described in Example 1C to give the title compound. $^1$H NMR (400 MHz, DMSO-d$_6$) δ ppm 11.24 (s, 1H), 8.39-8.42 (m, 1H), 7.88-8.01 (m, 2H), 7.75 (dd, J=6.9, 2.1 Hz, 1H), 7.29-7.35 (m, 3H), 3.56 (s, 1H), 2.33 (s, 2H), 2.32 (s, 3H), 2.05 (d, J=3.0 Hz, 2H), 1.93-1.97 (m, 3H), 1.54-1.72 (m, 12H); MS (APCI$^+$) M/Z 442 (M+H)$^+$.

Example 165

2-(4-chlorophenyl)-N-[4-(3,4-dimethylphenyl)-1-oxophthalazin-2(1H)-yl]acetamide

The product of Example 163A and 2-(4-chlorophenyl)acetic acid were treated using a method similar to that described in Example 17C to give the title compound. $^1$H NMR (400 MHz, DMSO-d$_6$) δ ppm 11.69 (s, 1H), 8.38-8.40 (m, 1H), 7.88-8.02 (m, 2H), 7.74 (d, J=6.5 Hz, 1H), 7.38-7.44 (m, 4H), 7.33-7.36 (m, 1H), 7.27-7.33 (m, 2H), 3.70 (s, 2H), 2.32 (s, 3H), 2.31 (s, 3H); MS (APCI$^+$) M/Z 418 (M+H)$^+$.

Example 166

2-(3,5-difluorophenyl)-N-[4-(3,4-dimethylphenyl)-1-oxophthalazin-2(1H)-yl]acetamide The product of Example 163A and 2-(3,5-difluorophenyl) acetic acid were treated using a method similar to that described in Example 17C to give the title compound. $^1$H NMR (400 MHz, DMSO-d$_6$) δ ppm 11.74 (s, 1H), 8.39-8.42 (m, 1H), 7.89-8.02 (m, 2H), 7.74-7.77 (m, 1H), 7.25-7.39 (m, 3H), 7.12-7.18 (m, 3H), 3.77 (s, 2H), 2.32 (s, 3H), 2.31 (s, 3H); MS (APCI$^+$) M/Z 420 (M+H)$^+$.

Example 167

(±)-2-(exo-bicyclo[2.2.1]hept-2-yl)-N-[1-oxo-4-(2-phenylethyl)phthalazin-2(1H)-yl]acetamide A mixture of 4-chlorophthalazin-1(2H)-one, ethynylbenzene, triethylamine, copper(I) iodide, and Pd(PPh$_3$)$_4$ in DMF was microwaved at 185° C. for 30 minutes, diluted with EtOAc, washed with water and saturated aqueous NH$_4$Cl, and chromatographed to give impure 4-(phenylethynyl)phthalazin-1(2H)-one, which was used without further purification. This material was treated with O-(diphenylphosphoryl) hydroxylamine as in Example 1B to give impure 2-amino-4-(phenylethynyl)phthalazin-1(2H)-one.

The impure 2-amino-4-(phenylethynyl)phthalazin-1(2H)-one and the product from Example 58A were treated using a method similar to that described in Example 1C to give impure (±)-2-(exo-bicyclo[2.2.1]heptan-2-yl)-N-(1-oxo-4-phenethynylphthalazin-2(1H)-yl)acetamide, which was dissolved in MeOH and stirred with a catalytic amount 10% Pd/C under H$_2$ (1 atm) for 4 hours. The mixture was filtered through celite, concentrated, and chromatographed on SiO$_2$ to give the title compound.: $^1$H NMR (300 MHz, DMSO-d$_6$) δ ppm 11.19 (s, 1H), 8.30-8.34 (m, 1H), 8.07-8.11 (m, 1H), 7.98 (ddd, J=8.0, 7.2, 1.5 Hz, 1H), 7.90 (ddd, J=7.9, 7.2, 1.3 Hz, 1H), 7.25-7.37 (m, 4H), 7.16-7.23 (m, 1H), 3.21-3.29 (m, 2H), 2.92-3.08 (m, 2H), 2.25 (dd, J=14.3, 8.3 Hz, 1H), 2.20-2.24 (m, 1H), 2.13-2.15 (m, 1H), 2.14 (dd, J=14.1, 7.4 Hz, 1H), 1.83-1.96 (m, 1H), 1.42-1.57 (m, 3H), 1.35-1.42 (m, 1H), 1.06-1.22 (m, 4H); MS (DCI+) M/Z 402 (M+H)+.

Example 168

(±)-2-(exo-bicyclo[2.2.1]hept-2-yl)-N-[4-(4-isopropylphenyl)-1-oxophthalazin-2(1H)-yl]acetamide Example 168A 2-amino-4-(4-isopropylphenyl)phthalazin-1(2H)-one 4-(4-Isopropylphenyl)phthalazin-1(2H)-one was treated with O-(diphenylphosphoryl)hydroxylamine using a method similar to that described in Example 1B to give the title compound. MS (APCI$^+$) M/Z 279 (M+H)$^+$.

Example 168B (±)-2-(exo-bicyclo[2.2.1]hept-2-yl)-N-[4-(4-isopropylphenyl)-1-oxophthalazin-2(1H)-yl]acetamide The product of Example 168A and (±)-2-(exo-bicyclo[2.2.1]hept-2-yl)acetic acid were treated using a method similar to that described in Example 17C to give the title compound. $^1$H NMR (400 MHz, DMSO-d$_6$) δ ppm 11.32 (s, 1H), 8.38-8.41 (m, 1H), 7.88-8.02 (m, 2H), 7.75-7.78 (m, 1H), 7.50-7.53 (m, 2H), 7.43-7.46 (m, 2H), 2.95-3.04 (m, 1H), 2.26 (dd, J=14.1, 8.3 Hz, 1H), 2.19-2.22 (m, 1H), 2.14 (dd, J=14.1, 7.4 Hz, 1H), 2.10-2.13 (m, 1H), 1.85-1.93 (m, 1H), 1.39-1.55 (m, 3H), 1.35-1.41 (m, 1H), 1.27 (d, J=6.9 Hz, 6H), 1.05-1.22 (m, 4H); MS (APCI$^+$) M/Z 417 (M+H)$^+$.

Example 169

2-(adamantan-1-yl)-N-[4-(4-isopropylphenyl)-1-oxophthalazin-2(1H)-yl]acetamide

The product of Example 168A and 2-(adamantan-1-yl) acetic acid were treated using a method similar to that described in Example 17C to give the title compound. $^1$H NMR (400 MHz, DMSO-d$_6$) δ ppm 11.24 (s, 1H), 8.39-8.42 (m, 1H), 7.89-8.02 (m, 2H), 7.75-7.78 (m, 1H), 7.50-7.53 (m, 2H), 7.43-7.46 (m, 2H), 2.96-3.06 (m, 1H), 2.05 (s, 2H), 1.94-1.97 (m, 3H), 1.65-1.72 (m, 9H), 1.58-1.64 (m, 3H), 1.28 (d, J=6.9 Hz, 6H); MS (APCI$^+$) M/Z 457 (M+H)$^+$.

Example 170

2-(4-chlorophenyl)-N-[4-(4-isopropylphenyl)-1-oxophthalazin-2(1H)-yl]acetamide

The product of Example 168A and 2-(4-chlorophenyl)acetic acid were treated using a method similar to that described in Example 17C to give the title compound. $^1$H NMR (400 MHz, DMSO-d$_6$) δ ppm 11.69-11.71 (bs, 1H), 8.38-8.41 (m, 1H), 7.89-8.03 (m, 2H), 7.75-7.77 (m, 1H), 7.50-7.53 (m, 2H), 7.42-7.46 (m, 2H), 7.37-7.43 (m, 4H), 3.70 (s, 2H), 2.93-3.06 (m, 1H), 1.27 (d, J=6.9 Hz, 6H); MS (APCI$^+$) M/Z 432 (M+H)$^+$.

Example 171

2-(3,5-difluorophenyl)-N-[4-(4-isopropylphenyl)-1-oxophthalazin-2(1H)-yl]acetamide The product of Example 168A and 2-(3,5-difluorophenyl) acetic acid were treated using a method similar to that described in Example 17C to give the title compound. $^1$H NMR (400 MHz, DMSO-d$_6$) δ ppm 11.70-11.81 (m, 1H), 8.40-8.42 (m, 1H), 7.89-8.03 (m, 2H), 7.75-7.78 (m, 1H), 7.51-7.53 (m, 2H), 7.43-7.46 (m, 2H), 7.07-7.22 (m, 3H), 3.77 (s, 2H), 2.94-3.07 (m, 1H), 1.27 (d, J=6.9 Hz, 6H); MS (APCI$^+$) M/Z 434 (M+H)$^+$.

Example 172

(±)-2-(exo-bicyclo[2.2.1]hept-2-yl)-N-[1-oxo-4-(1-phenylcyclopropyl)phthalazin-2(1H)-yl]acetamide A solution of (2-(ethoxycarbonyl)phenyl)zinc(II) bromide (2.2 mL, 1.1 mmol) was added to a mixture of 1-phenylcyclopropanecarbonyl chloride (0.200 g, 1.1 mmol) and Pd(PPh$_3$)$_4$ (0.0644 g, 0.056 mmol) in THF (1.1 mL), stirred for 2 hours, diluted with EtOAc, washed with 1N HCl and brine, dried (Na$_2$SO$_4$), filtered, and chromatographed (20% Et$_2$O/hexanes) to give 216.2 mg of impure ethyl 2-(1-phenylcyclopropanecarbonyl)benzoate. A mixture of impure ethyl 2-(1-phenylcyclopropanecarbonyl)benzoate (0.216 g, 0.735 mmol) and hydrazine hydrate (0.13 mL, 2.298 mmol) in ethanol (3 mL) was stirred at 75° C. overnight, and concentrated to give 179.7 mg of impure 4-(1-phenylcyclopropyl) phthalazin-1(2H)-one, which was treated with O-(diphenylphosphoryl)hydroxylamine using a method similar to that described in Example 1B to give impure 2-amino-4-(1-phenylcyclopropyl)phthalazin-1(2H)-one.

The impure 2-amino-4-(1-phenylcyclopropyl)phthalazin-1(2H)-one and the product of Example 58A were treated using a method similar to that described in Example 53 to give the title compound. $^1$H NMR (300 MHz, DMSO-d$_6$) δ ppm 11.26 (s, 1H), 8.28-8.32 (m, 1H), 7.75-7.98 (m, 3H), 7.22-7.30 (m, 2H), 7.10-7.21 (m, 3H), 2.28 (dd, J=14.3, 8.3 Hz, 1H), 2.12-2.24 (m, 3H), 1.85-1.96 (m, 1H), 1.33-1.60 (m, 8H), 1.02-1.26 (m, 4H); MS (ESI$^-$) M/Z 412 (M–H)$^-$.

Example 173

2-(adamantan-1-yl)-N-[4-isopropyl-1-oxo-7-(trifluoromethyl)phthalazin-2(1H)-yl]acetamide

Example 173A 2-amino-4-isopropyl-7-(trifluoromethyl)phthalazin-1(2H)-one

A suspension of 5-(trifluoromethyl)isobenzofuran-1,3-dione and 2-methylpropan-2-amine in acetic acid was heated at 100° C. overnight, concentrated, diluted with EtOAc, washed with saturated aqueous NaHCO$_3$ and brine, dried (Na$_2$SO$_4$), filtered, and concentrated to give crude 2-tert-butyl-5-(trifluoromethyl)isoindoline-1,3-dione, which was used without purification.

The crude 2-tert-butyl-5-(trifluoromethyl)isoindoline-1,3-dione was treated with isopropylmagnesium bromide and hydrazine using a method similar to that described in Example 1A, followed by treatment with O-(diphenylphosphoryl)hydroxylamine using a method similar to that described in Example 1B to give the title compound. LC/MS (APCI) m/z 272 (M+H)$^+$.

Example 173B 2-(adamantan-1-yl)-N-[4-isopropyl-1-oxo-7-(trifluoromethyl)phthalazin-2(1H)-yl]acetamide The product from Example 173A and 2-(adamantan-1-yl)acetyl chloride were treated as in Example 1C to give the title compound. $^1$H NMR (300 MHz, DMSO-d$_6$) δ ppm 11.19-11.28 (m, 1H), 8.58 (s, 1H), 8.28-8.40 (m, 2H), 3.58-3.70 (m, 1H), 2.04 (s, 2H), 1.93-1.98 (bs, 3H), 1.55-1.75 (m, 12H), 1.27 (d, J=6.7 Hz, 6H); MS (ESI$^+$) M/Z 448 (M+H)$^+$.

Example 174

2-(adamantan-1-yl)-N-[7-bromo-4-(4-methoxyphenyl)-1-oxophthalazin-2(1H)-yl]acetamide

Example 174A 2-amino-7-bromo-4-(4-methoxyphenyl)phthalazin-1(2H)-one

A suspension of AlCl$_3$ and 5-bromoisobenzofuran-1,3-dione in 1,2-dichloroethane was briefly heated to form a solution, and cooled to room temperature. Anisole was added dropwise and stirred overnight. The mixture was quenched with 1N HCl, extracted with dichloromethane, dried (Na$_2$SO$_4$), filtered, and triturated (Hexanes/Et$_2$O) to give a ~1:1 mixture of 4-bromo-2-(4-methoxybenzoyl)benzoic acid:5-bromo-2-(4-methoxybenzoyl)benzoic acid as a white solid. A solution of this material and hydrazine hydrate in EtOH was heated at 60° C. overnight, concentrated, diluted with EtOAc, washed with saturated aqueous NaHCO$_3$ and brine, dried (Na$_2$SO$_4$), and chromatographed (15-50% (1:1 EtOAc:dichloromethane)/hexanes) to give a mixture of 6-bromo-4-(4-methoxyphenyl)phthalazin-1(2H)-one and 7-bromo-4-(4-methoxyphenyl)phthalazin-1(2H)-one as a white solid. A solution of this mixture in THF was treated with O-(diphenylphosphoryl)hydroxylamine using a method similar to that described in Example 1B, and the regioisomers separated upon purification by chromatography on SiO$_2$ (7% EtOAc/dichloromethane) to give the title compound. $^1$H NMR (300 MHz, DMSO) δ 8.45 (d, J=2.1, 1H), 8.05 (dd, J=8.7, 2.2, 1H), 7.69 (d, J=8.7, 1H), 7.59-7.48 (m, 2H), 7.17-7.07 (m, 2H), 6.55 (d, J=6.1, 2H), 3.85 (s, 3H).

Example 174B 2-(adamantan-1-yl)-N-[7-bromo-4-(4-methoxyphenyl)-1-oxophthalazin-2(1H)-yl]acetamide The product from Example 174A and 2-(adamant-1-yl)acetyl chloride were treated using a method similar to that described in Example 53 to give the title compound. $^1$H NMR (300 MHz, DMSO-d$_6$) δ ppm 11.28 (s, 1H), 8.50 (d, J=2.1 Hz, 1H), 8.14 (dd, J=8.6, 2.2 Hz, 1H), 7.70 (d, J=8.7 Hz, 1H), 7.51-7.55 (m, 2H), 7.11-7.15 (m, 2H), 3.85 (s, 3H), 2.05 (s, 2H), 1.92-1.98 (bs, 3H), 1.58-1.70 (m, 12H); MS (ESI$^+$) M/Z, 524 (M+H)$^+$.

Example 175

2-(adamantan-1-yl)-N-[6-bromo-4-(4-methoxyphenyl)-1-oxophthalazin-2(1H)-yl]acetamide

Example 175A 2-amino-6-bromo-4-(4-methoxyphenyl)phthalazin-1(2H)-one

The product was obtained from Example 174A. $^1$H NMR (300 MHz, DMSO-d$_6$) δ 8.28 (d, J=8.6, 1H), 8.05 (dd, J=8.5, 1.9, 1H), 7.79 (d, J=1.8, 1H), 7.59-7.50 (m, 2H), 7.18-7.09 (m, 2H), 6.52 (d, J=6.2, 2H), 3.86 (s, 3H).

Example 175B 2-(adamantan-1-yl)-N-[6-bromo-4-(4-methoxyphenyl)-1-oxophthalazin-2(1H)-yl]acetamide The product from Example 175A and 2-(adamant-1-yl)acetyl chloride were treated using a method similar to that described in Example 53 to give the title compound. $^1$H NMR (300 MHz, DMSO-d$_6$) δ ppm 11.26 (s, 1H), 8.31 (d, J=8.5 Hz, 1H), 8.11 (dd, J=8.5, 1.9 Hz, 1H), 7.80 (d, J=1.9 Hz, 1H), 7.53-7.56 (m, 2H), 7.12-7.16 (m, 2H), 3.86 (s, 3H), 2.05 (s, 2H), 1.90-1.99 (bs, 3H), 1.57-1.69 (m, 12H); MS (ESI$^+$) M/Z, 524 (M+H)$^+$.

Example 176

N-[6-bromo-4-(4-methoxyphenyl)-1-oxophthalazin-2(1H)-yl]-2-(3,5-difluorophenyl)acetamide The product from Example 175A and 2-(3,5-difluorophenyl)acetyl chloride were treated using a method similar to that described in Example 53 to give the title compound. $^1$H NMR (300 MHz, DMSO-d$_6$) δ ppm 11.72-11.78 (bs, 1H), 8.31 (d, J=8.5 Hz, 1H), 8.12 (dd, J=8.5, 1.9 Hz, 1H), 7.81 (d, J=1.9 Hz, 1H), 7.53-7.56 (m, 2H), 7.06-7.22 (m, 5H), 3.85 (s, 3H), 3.76 (s, 2H); MS (ESI+) M/Z 502 (M+H)+.

Example 177

N-[7-bromo-4-(4-methoxyphenyl)-1-oxophthalazin-2(1H)-yl]-2-(3,5-difluorophenyl)acetamide The product from Example 174A and 2-(3,5-difluorophenyl)acetyl chloride were treated using a method similar to that described in Example 53 to give the title compound. $^1$H NMR (300 MHz, DMSO-$d_6$) δ ppm 11.77-11.80 (bs, 1H), 8.49 (d, J=2.1 Hz, 1H), 8.15 (dd, J=8.6, 2.2 Hz, 1H), 7.70 (d, J=8.7 Hz, 1H), 7.51-7.55 (m, 2H), 7.06-7.22 (m, 5H), 3.85 (s, 3H), 3.76-3.77 (bs, 2H); MS (ESI+) M/Z 503 (M+H)+.

Example 178

2-(3-bromoadamantan-1-yl)-N-(7-oxo-4-phenylthieno[2,3-d]pyridazin-6(7H)-yl)acetamide The product from Example 29B and 2-(3-bromoadamantan-1-yl)acetic acid were processed using a method similar to that described in Example 17C to afford the title compound. $^1$H NMR (500 MHz, DMSO-$d_6$) δ ppm 11.47 (s, 1H), 8.36 (d, J=5.2 Hz, 1H), 7.71-7.73 (m, 2H), 7.56-7.59 (m, 4H), 2.32-2.34 (m, 2H), 2.27-2.32 (m, 2H), 2.19-2.25 (m, 2H), 2.17 (s, 2H), 2.12-2.16 (m, 2H), 1.62-1.75 (m, 5H), 1.56-1.60 (m, 1H); MS (APCI+) M/Z 498 (M+H)+.

Example 179

2-(3-fluoroadamantan-1-yl)-N-(7-oxo-4-phenylthieno[2,3-d]pyridazin-6(7H)-yl)acetamide The product from Example 180 and (diethylamino)sulfur trifluoride were processed using a method similar to that described in Example 60 to afford the title compound. $^1$H NMR (500 MHz, DMSO-$d_6$) δ 11.45 (s, 1H), 8.36 (d, J=5.2, 1H), 7.75-7.68 (m, 2H), 7.61-7.52 (m, 4H), 2.25 (s, 2H), 2.20 (s, 2H), 1.71-1.85 (m, 6H), 1.46-1.65 (m, 6H); MS (APCI+) M/Z 438 (M+H)+.

Example 180

2-(3-hydroxyadamantan-1-yl)-N-(7-oxo-4-phenylthieno[2,3-d]pyridazin-6(7H)-yl)acetamide The product from Example 29B and 2-(3-hydroxyadamantan-1-yl)acetic acid were processed using a method similar to that described in Example 17C to afford the title compound. $^1$H NMR (500 MHz, DMSO-$d_6$) δ ppm 11.37 (s, 1H), 8.35 (d, J=5.2 Hz, 1H), 7.70-7.73 (m, 2H), 7.56-7.58 (m, 4H), 4.39 (s, 1H), 2.12 (s, 2H), 2.07-2.12 (m, 2H), 1.41-1.62 (m, 12H); MS (APCI+) M/Z 436 (M+H)+.

Example 181

N-[4-(4-chlorophenyl)-5,8-difluoro-1-oxophthalazin-2(1H)-yl]-2-(3,5-difluorophenyl)acetamide

Example 181A 2-amino-5,8-difluoro-4-(4-chlorophenyl)phthalazin-2(1H)-one 4,7-Difluoroisobenzofuran-1,3-dione was treated with chlorobenzene using a method similar to that described in Example 14A, followed by treatment with O-(diphenylphosphoryl)hydroxylamine using a method similar to that described in Example 9B to give the title compound. MS (APCI+) M/Z 308 (M+H)+.

Example 181B

N-[4-(4-chlorophenyl)-5,8-difluoro-1-oxophthalazin-2(1H)-yl]-2-(3,5-difluorophenyl)acetamide The product from Example 181A and 2-(3,5-difluorophenyl)acetic acid were treated using a method similar to that described in Example 17C to give the title compound. $^1$H NMR (400 MHz, DMSO-$d_6$) δ ppm 11.73-11.75 (bs, 1H), 7.77-7.90 (m, 2H), 7.53-7.59 (m, 4H), 7.04-7.21 (m, 3H), 3.75 (s, 2H); MS (APCI+) M/Z 462 (M+H)+.

Example 182

2-(4-chlorophenyl)-N-[4-(4-chlorophenyl)-5,8-difluoro-1-oxophthalazin-2(1H)-yl]acetamide The product from Example 181A and 2-(4-chlorophenyl)acetic acid were treated using a method similar to that described in Example 17C to give the title compound. $^1$H NMR (400 MHz, DMSO-$d_6$) δ ppm 11.69 (s, 1H), 7.74-7.90 (m, 2H), 7.53 (s, 4H), 7.32-7.45 (m, 4H), 3.69 (s, 2H); MS (APCI+) M/Z 460 (M+H)+.

Example 183

2-(adamantan-1-yl)-N-[4-(4-chlorophenyl)-5,8-difluoro-1-oxophthalazin-2(1H)-yl]acetamide The product from Example 181A and 2-(adamantan-1-yl) acetic acid were treated using a method similar to that described in Example 17C to give the title compound. $^1$H NMR (400 MHz, DMSO) δ 11.25 (s, 1H), 7.87-7.73 (m, 2H), 7.53 (s, 4H), 2.04 (d, J=1.6, 2H), 1.94 (m, 3H), 1.67 (m, 12H); MS (APCI+) M/Z 484 (M+H)+.

Example 184

(±)-2-(exo-bicyclo[2.2.1]hept-2-yl)-N-[4-(4-chlorophenyl)-5,8-difluoro-1-oxophthalazin-2(1H)-yl]acetamide The product from Example 181A and the product of Example 58A were treated using a method similar to that described in Example 1C to give the title compound. $^1$H NMR (400 MHz, DMSO-$d_6$) δ ppm 11.32 (s, 1H), 7.73-7.90 (m, 2H), 7.49-7.57 (m, 4H), 2.25 (dd, J=14.3, 8.2 Hz, 1H), 2.17-2.22 (m, 1H), 2.13 (dd, J=14.3, 7.5 Hz, 1H), 2.06-2.10 (m, 1H), 1.82-1.92 (m, 1H), 1.39-1.54 (m, 3H), 1.34-1.39 (m, 1H), 1.04-1.20 (m, 4H); MS (APCI+) M/Z 444 (M+H)+.

Example 185

2-(adamantan-1-yl)-N-(1-oxo-4-phenyl-5,6,7,8-tetrahydrophthalazin-2(1H)-yl)acetamide

Example 185A 2-amino-4-Phenyl-5,6,7,8-tetrahydrophthalazin-1(2H)-one

4-Phenyl-5,6,7,8-tetrahydrophthalazin-1(2H)-one was treated with O-(diphenylphosphoryl)hydroxylamine using a method similar to that described in Example 1B to give the title compound. MS (APCI+) M/Z 242 (M+H)+.

Example 185B 2-(adamantan-1-yl)-N-(1-oxo-4-phenyl-5,6,7,8-tetrahydrophthalazin-2(1H)-yl)acetamide The product from Example 185A and 2-(adamantan-1-yl) acetic acid were treated using a method similar to that described in Example 17C to give the title compound. $^1$H NMR (400 MHz, DMSO-$d_6$) δ ppm 11.16 (s, 1H), 7.39-7.52 (m, 5H), 2.51-2.56 (m, 2H), 2.37-2.41 (m, 2H), 2.01 (s, 2H), 1.90-1.96 (bs, 3H), 1.70-1.77 (m, 2H), 1.53-1.71 (m, 14H); MS (APCI+) M/Z 419 (M+H)+.

Example 186

2-(3,5-difluorophenyl)-N-(1-oxo-4-phenyl-5,6,7,8-tetrahydrophthalazin-2(1H)-yl)acetamide The product from Example 185A and 2-(3,5-difluorophenyl)acetic acid were treated using a method similar to that described in Example 17C to give the title compound. $^1$H NMR (400 MHz, DMSO-$d_6$) δ ppm 11.68-11.71 (bs, 1H), 7.39-7.51 (m, 5H), 7.04-7.20 (m, 3H), 3.72 (s, 2H), 2.51-2.55 (m, 2H), 2.37-2.41 (m, 2H), 1.69-1.77 (m, 2H), 1.58-1.65 (m, 2H); MS (APCI+) M/Z 396 (M+H)+.

Example 187

2-(4-chlorophenyl)-N-(1-oxo-4-phenyl-5,6,7,8-tetrahydrophthalazin-2(1H)-yl)acetamide The product from Example 185A and 2-(4-chlorophenyl) acetic acid were treated using a method similar to that described in Example 17C to give the title compound. $^1$H NMR (400 MHz, DMSO-$d_6$) δ ppm 11.64 (s, 1H), 7.29-7.51 (m, 9H), 3.65 (s, 2H), 2.50-2.55 (m, 2H), 2.36-2.40 (m, 2H), 1.68-1.76 (m, 2H), 1.57-1.65 (m, 2H); MS (APCI+) M/Z 394 (M+H)+.

Example 188

2-(3,5-difluorophenyl)-N-(1-oxo-4-phenyl-1,5,6,7-tetrahydro-2H-cyclopenta[d]pyridazin-2-yl)acetamide

Example 188A 4-phenyl-2,5,6,7-tetrahydro-1H-cyclopenta[d]pyridazin-1-one 5,6-dihydro-1H-cyclopenta[c]furan-1,3(4H)-dione (1 g, 7 mmol) was added slowly to a well-stirred suspension of aluminum trichloride (1.9 g, 14 mmol) in 15 mL of benzene and 15 mL of CS$_2$. The red reaction mixture was refluxed for 1.5 hours. After cooling, the mixture was poured into water, and extracted with CHCl$_3$. The organic layer was dried (Na$_2$SO$_4$), filtered and concentrated to afford a solid. The solid was dissolved in 20 mL of EtOH, and 5 mL of hydrazine hydrate was added. The mixture was refluxed for 12 hours, allowed to cool, and filtered. The solid collected was washed with water, and dried to afford the title compound. MS (APCI+) M/Z 213 (M+H)+.

Example 188B 4-phenyl-2,5,6,7-tetrahydro-1H-cyclopenta[d]pyridazin-1-one

The product of Example 188A was treated with O-(diphenylphosphoryl)hydroxylamine using a method similar to that described in Example 1B to give the title compound. MS (APCI+) M/Z 228 (M+H)+.

Example 188C 2-(3,5-difluorophenyl)-N-(1-oxo-4-phenyl-1,5,6,7-tetrahydro-2H-cyclopenta[d]pyridazin-2-yl)acetamide The product from Example 188B and 2-(3,5-difluorophenyl)acetic acid were treated using a method similar to that described in Example 17C to give the title compound. $^1$H NMR (400 MHz, DMSO-$d_6$) δ ppm 11.75 (s, 1H), 7.59-7.62 (m, 2H), 7.44-7.55 (m, 3H), 7.08-7.20 (m, 3H), 3.74-3.75 (bs, 2H), 3.02-3.07 (m, 2H), 2.82-2.86 (m, 2H), 2.09 (p, J=7.5 Hz, 2H); MS (APCI+) M/Z 382 (M+H)+.

Example 189

2-(adamantan-1-yl)-N-(1-oxo-4-phenyl-1,5,6,7-tetrahydro-2H-cyclopenta[d]pyridazin-2-yl)acetamide The product from Example 188B and 2-(adamantan-1-yl) acetic acid were treated using a method similar to that described in Example 17C to give the title compound. $^1$H NMR (400 MHz, DMSO-$d_6$) δ ppm 11.22 (s, 1H), 7.53-7.65 (m, 2H), 7.41-7.52 (m, 3H), 3.02-3.07 (m, 2H), 2.81-2.86 (m, 2H), 2.09 (p, J=7.6 Hz, 2H), 2.03 (s, 2H), 1.92-1.95 (m, 3H), 1.63-1.71 (m, 9H), 1.56-1.63 (m, 3H); MS (APCI+) M/Z 404 (M+H)+.

Example 190

2-(4-chlorophenyl)-N-(1-oxo-4-phenyl-1,5,6,7-tetrahydro-2H-cyclopenta[d]pyridazin-2-yl)acetamide The product from Example 188B and 2-(4-chlorophenyl) acetic acid were treated using a method similar to that described in Example 17C to give the title compound. $^1$H NMR (400 MHz, DMSO-$d_6$) δ ppm 11.69 (s, 1H), 7.57-7.62 (m, 2H), 7.45-7.52 (m, 3H), 7.35-7.43 (m, 4H), 3.68 (s, 2H), 3.01-3.06 (m, 2H), 2.81-2.85 (m, 2H), 2.09 (p, J=7.6 Hz, 2H); MS (APCI+) M/Z 380 (M+H)+.

Example 191

2-(methylthio)-N-[1-oxo-4-(trifluoromethyl)phthalazin-2(1H)-yl]acetamide

The product from Example 11B and 2-(methylthio)acetic acid were treated using a method similar to that described in Example 57 to give the title compound $^1$H NMR (500 MHz, DMSO-$d_6$/Deuterium Oxide) δ ppm 8.45 (ddd, J=8.0, 1.4, 0.7 Hz, 1H), 8.15 (td, J=7.7, 1.4 Hz, 1H), 8.04-8.11 (m, 2H), 3.37 (s, 2H), 2.24 (s, 3H); MS (ESI−) M/Z 316 (M−H)−.

Example 192

2-(adamantan-1-ylthio)-N-[1-oxo-4-(trifluoromethyl) phthalazin-2(1H)-yl]acetamide The product from Example 11B and 2-(adamantan-1-ylthio)acetic acid were treated using a method similar to that described in Example 17C to give the title compound $^1$H NMR (400 MHz, DMSO-d$_6$) δ ppm 11.68-11.85 (bs, 1H), 8.43 (ddd, J=8.0, 1.4, 0.7 Hz, 1H), 8.13 (ddd, J=8.0, 7.4, 1.4 Hz, 1H), 8.03-8.08 (m, 1H), 8.00-8.05 (m, 1H), 3.44 (s, 2H), 2.01-2.04 (m, 3H), 1.86-1.89 (m, 6H), 1.65-1.69 (m, 6H); MS (APCI$^+$) M/Z 438 (M+H)$^+$.

Example 193

2-(adamantan-1-ylthio)-N-(1-oxo-4-phenylphthalazin-2(1H)-yl)acetamide

The product from Example 17B and 2-(adamantan-1-ylthio)acetic acid were treated using a method similar to that described in Example 17C to give the title compound $^1$H NMR (400 MHz, DMSO-d$_6$) δ ppm 11.57 (s, 1H), 8.39-8.42 (m, 1H), 7.89-8.04 (m, 2H), 7.74-7.76 (m, 1H), 7.58-7.60 (m, 5H), 3.41 (s, 2H), 1.99-2.02 (m, 3H), 1.86-1.89 (m, 6H), 1.62-1.69 (m, 6H); MS (APCI$^+$) M/Z 446 (M+H)$^+$.

Example 194

2-(1,3-benzodioxol-5-yl)-N-[4-(4-chlorophenyl)-1-oxophthalazin-2(1H)-yl]acetamide The product from Example 86A and 2-(benzo[d][1,3]dioxol-5-yl)acetic acid were treated using a method similar to that described in Example 57 to give the title compound. $^1$H NMR (500 MHz, DMSO-d$_6$/D$_2$O) δ 8.41 (m, 1H), 8.01-7.95 (m, 2H), 7.72 (m, 1H), 7.63 (m, 4H), 6.96 (d, J=1.6, 1H), 6.88 (d, J=7.9, 1H), 6.84 (dd, J=8.0, 1.6, 1H), 5.99 (s, 2H), 3.61 (s, 2H); MS (APCI$^+$) M/Z 434 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:
1. A compound of formula (I)

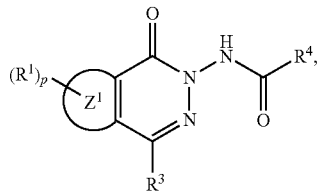

(I)

or a pharmaceutically acceptable salt thereof, wherein
$Z^1$ is a ring fused with the pyridazine ring, selected from the group consisting of benzo, cycloalkyl, and cycloalkenyl;
$R^1$ is an optional substituent wherein each occurrence of $R^1$ is independently $G^a$, alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —S(O)$_2$NR$^a$R$^b$, —C(O)R$^a$, —C(O)OR$^a$, —C(O)NR$^a$R$^b$, —N(R$^a$)COOR$^b$, —N(R$^a$)CONR$^a$R$^b$, —N(R$^a$)SO$_2$NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$OC(O)R$^a$, —(CR$^{za}$R$^{zb}$)$_m$—OC(O)NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—S(O)$_2$NR$^a$R$^b$, —(CR$^{za}$R$^{zb}$)$_m$—C(O)R$^a$, —CR$^{za}$R$^{zb}$)$_m$—C(O)OR$^a$—(CR$^{za}$R$^{zb}$)$_m$—C(O)NR$^a$R$^b$, —(CR$^{za}$R$^{zb}$)$_m$N-R$^a$R$^b$, —(CR$^{za}$R$^{zb}$)$_m$—N(R$^a$)COOR$^b$, —(CR$^{za}$R$^{zb}$)$_m$—(R$^a$)CONR$^a$R$^b$)R$^a$R$^b$, —(CR$^{za}$R$^{zb}$)$_m$—N(R$^a$)SO$_2$NR$^a$R$^b$, or —(CR$^{za}$R$^{zb}$)$_m$-G$^a$;
p is 0, 1, 2, 3, or 4;
$R^3$ is hydrogen, alkyl, alkenyl, alkynyl, halogen, haloalkyl, —(CR$^{3a}$R$^{3b}$)$_m$-G$^3$a, or G$^{3a}$;
$G^{3a}$, at each occurrence, is independently aryl, cycloalkyl, or cycloalkenyl; each of which is optionally substituted;
$R^4$ is alkenyl, alkynyl, haloalkyl, —(CR$^{4a}$R$^{4b}$)$_n$-G$^{4a}$, or alkyl which is optionally substituted with one or two groups independently selected from the group consisting of S(R$^{1a}$), O(R$^{1a}$) and N(R$^{1a}$)$_2$;
each occurrence of R$^{1a}$ is independently hydrogen, G$^a$, —(CR$^{za}$R$^{zb}$)$_m$-G$^a$, alkyl, haloalkyl, hydroxyalkyl, or alkoxyalkyl;
$G^{4a}$, at each occurrence, is independently aryl, heteroaryl, heterocycle, cycloalkyl, or cycloalkenyl; each of which is optionally substituted;
$G^{3a}$ and $G^{3a}$, at each occurrence, are each independently unsubstituted or substituted with 1, 2, 3, or 4 substituents independently selected from the group consisting of G$^a$, alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —S(O)$_2$NR$^a$R$^b$, —C(O)R$^a$, —C(O)OR$^a$, —C(O)NR$^a$R$^b$, —N(R$^a$)COOR$^b$, —N(R$^a$)CONR$^a$R$^b$, —N(R$^a$)SO$_2$NR$^a$R$^b$, —(CR$^{za}$R$^{zb}$)$_m$-G$^a$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—S(O)$_2$NR$^a$R$^b$, —(CR$^{za}$R$^{zb}$)$_m$—C(O)R$^a$, —(CR$^{za}$R$^{zb}$)$_m$C(O)OR$^a$, —(CR$^{za}$R$^{zb}$)$_m$—C(O)NR$^a$R$^b$, —(CR$^{za}$R$^{zb}$)$_m$—NR$^a$R$^b$, —(CR$^{za}$R$^{zb}$)$_m$—N(R$^a$)COOR$^b$, —(CR$^{za}$R$^{zb}$)$_m$—N(R$^a$)CONR$^a$R$^b$, and —(CR$^{za}$R$^{zb}$)$_m$—N(R$^a$)SO$_2$NR$^a$R$^b$;
$G^a$, at each occurrence, is independently aryl, heteroaryl, heterocycle, cycloalkyl, or cycloalkenyl; each of which is independently unsubstituted or substituted with 1, 2, or 3 substituents selected from the group consisting of alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —S(O)$_2$NR$^a$R$^b$, —C(O)R$^a$, —C(O)OR$^a$, —C(O)NR$^a$R$^b$, —N(R$^a$)COOR$^b$, —N(R$^a$)CONR$^a$R$^b$, —N(R$^a$)SO$_2$NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—S(O)$_2$NR$^a$R$^b$, —(CR$^{za}$R$^{zb}$)$_m$C(O)R$^a$, —(CR$^{za}$R$^{zb}$)$_m$C(O)OR$^a$, —(CR$^{za}$R$^{zb}$)$_m$—OC(O)NR$^a$R$^b$, —(CR$^{za}$R$^{zb}$)$_m$—NR$^a$R$^b$, —(CR$^{za}$R$^{zb}$)$_m$—N(R$^a$)COOR$^b$, —(CR$^{za}$R$^{zb}$)$_m$—N(R$^a$)CONR$^a$R$^b$, and —(CR$^{za}$R$^{zb}$)$_m$—N(R$^a$)SO$_2$NR$^a$R$^b$;
R$^{za}$, R$^{zb}$, R$^{3a}$, R$^{3b}$, R$^{4a}$, and R$^{4b}$, at each occurrence, are each independently hydrogen, alkyl, halogen, or haloalkyl;
R$^a$ and R$^b$, at each occurrence, are each independently hydrogen, alkyl, or haloalkyl; and
m and n, at each occurrence, are each independently 1, 2, 3, or 4;

with the proviso that when $Z^1$ is benzo, p is 0 or 4, $R^1$ is halogen, $R^3$ is $G^{3a}$, and $G^{3a}$ is aryl, substituted with 1 or 2 substituents selected from the group consisting of alkyl and unsubstituted aryl, then $R^4$ is other than unsubstituted alkyl or haloalkyl.

2. The compound according to claim 1 or a pharmaceutically acceptable salt thereof, wherein $Z^1$ is benzo or cycloalkyl.

3. The compound of formula (I-a) according to claim 1 or a pharmaceutically acceptable salt thereof,

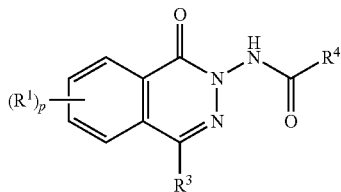

(I-a)

wherein
$R^1$, $R^3$, p, and $R^4$ are as set forth in claim 1.

4. The compound of formula (I-e) according to claim 1 or a pharmaceutically acceptable salt thereof

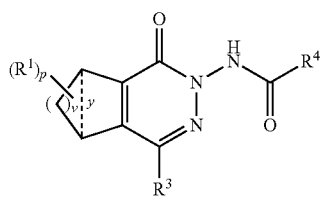

(I-e)

wherein
$R^1$, $R^3$, $R^4$, and p are as set forth in claim 1; and
v is 1, 2, or 3; and
y is absent, a bond, —$CH_2$—, or —$CH_2CH_2$—.

5. The compound of formula (I) according to claim 1, or a pharmaceutically acceptable salt thereof, wherein
$R^3$ is alkyl, halogen, haloalkyl, $G^{3a}$, or —$(CR^{3a}R^{3b})_m$-$G^{3a}$.

6. The compound of formula (I) according claim 1, or a pharmaceutically acceptable salt thereof, wherein $R^4$ is unsubstituted alkyl, haloalkyl, —$C(R^{4a}R^{4b})_n$-$G^{4a}$, or alkyl substituted with a —$S(R^{1a})$ group.

7. The compound of formula (I) according to claim 1, or a pharmaceutically acceptable salt thereof, wherein $Z^1$ is benzo or cycloalkyl; and
$R^4$ is unsubstituted alkyl, haloalkyl, —$C(R^{4a}R^{4b})_n$-$G^{4a}$, or alkyl substituted with a —$S(R^{1a})$ group.

8. The compound of formula (I) according to claim 1, or a pharmaceutically acceptable salt thereof, wherein
$Z^1$ is benzo or cycloalkyl; and
$R^4$ is —$C(R^{4a}R^{4b})_n$-$G^{4a}$.

9. The compound of formula (I) according to claim 1, or a pharmaceutically acceptable salt thereof, wherein
$Z^1$ is benzo or cycloalkyl;
$R^4$ is —$C(R^{4a}R^{4b})_n$-$G^{4a}$; and
$R^3$ is alkyl, halogen, haloalkyl, $G^{3a}$, or —$(CR^{3a}R^{3b})_m$-$G^{3a}$.

10. The compound of formula (I) according to claim 1, or a pharmaceutically acceptable salt thereof, wherein
$Z^1$ is benzo or cycloalkyl;
$R^4$ is —$C(R^{4a}R^{4b})_n$-$G^{4a}$;
$R^3$ is alkyl, halogen, haloalkyl, $G^{3a}$, or —$(CR^{3a}R^{3b})_m$-$G^{3a}$; and
$G^{3a}$ is aryl or cycloalkyl.

11. The compound of formula (I) according to claim 1, or a pharmaceutically acceptable salt thereof, wherein
$Z^1$ is benzo or cycloalkyl; and
$R^4$ is unsubstituted alkyl or haloalkyl.

12. The compound of formula (I) according to claim 1, or a pharmaceutically acceptable salt thereof, wherein
$Z^1$ is benzo or cycloalkyl;
$R^4$ is unsubstituted alkyl or haloalkyl; and
$R^3$ is alkyl, halogen, haloalkyl, $G^{3a}$, or —$(CR^{3a}R^{3b})_m$-$G^{3a}$.

13. The compound of formula (I) according to claim 1, or a pharmaceutically acceptable salt thereof, wherein
$Z^1$ is benzo or cycloalkyl;
$R^4$ is unsubstituted alkyl or haloalkyl;
$R^3$ is alkyl, halogen, haloalkyl, $G^{3a}$, or —$(CR^{3a}R^{3b})_m$-$G^{3a}$; and
$G^{3a}$ is aryl or cycloalkyl.

14. The compound of formula (I) according to claim 1, or a pharmaceutically acceptable salt thereof, wherein
$Z^1$ is benzo or cycloalkyl; and
$R^4$ is alkyl substituted with a —$S(R^{1a})$ group.

15. The compound of formula (I) according to claim 1, or a pharmaceutically acceptable salt thereof, wherein
$Z^1$ is benzo or cycloalkyl;
$R^4$ is alkyl substituted with a —$S(R^{1a})$ group; and
$R^3$ is alkyl, halogen, haloalkyl, $G^{3a}$, or —$(CR^{3a}R^{3b})_m$-$G^{3a}$.

16. The compound of formula (I) according to claim 1, or a pharmaceutically acceptable salt thereof, wherein
$Z^1$ is benzo or cycloalkyl;
$R^4$ is alkyl substituted with a —$S(R^{1a})$ group;
$R^3$ is alkyl, halogen, haloalkyl, $G^{3a}$, or —$(CR^{3a}R^{3b})_m$-$G^{3a}$; and
$G^{3a}$ is aryl or cycloalkyl.

17. The compound of formula (I) according to claim 1, or a pharmaceutically acceptable salt thereof, wherein the compound is selected from the group consisting of
2-(4-chlorophenyl)-N-(4-isopropyl-1-oxophthalazin-2(1H)-yl)acetamide;
2-(1-adamantyl)-N-[4-(4-bromophenyl)-1-oxophthalazin-2(1H)-yl]acetamide;
N-[4-(4-bromophenyl)-1-oxophthalazin-2(1H)-yl]-2-(4-chlorophenyl)acetamide;
2-(4-chlorophenyl)-N-(1-oxo-4-phenylphthalazin-2(1H)-yl)acetamide;
2-(3,5-difluorophenyl)-N-(4-isopropyl-1-oxophthalazin-2(1H)-yl)acetamide;
2-(1-adamantyl)-N-(4-isopropyl-1-oxophthalazin-2(1H)-yl)acetamide;
2-(1-adamantyl)-N-(4-isopropyl-1-oxo-5,6,7,8-tetrahydro-5,8-ethanophthalazin-2(1H)-yl)acetamide;
2-(3,5-difluorophenyl)-N-[1-oxo-4-(trifluoromethyl)phthalazin-2(1H)-yl]acetamide;
2-(1-adamantyl)-N-[1-oxo-4-(trifluoromethyl)phthalazin-2(1H)-yl]acetamide;
2-(4-chlorophenyl)-N-[1-oxo-4-(trifluoromethyl)phthalazin-2(1H)-yl]acetamide;
N-(5,8-difluoro-1-oxo-4-phenylphthalazin-2(1H)-yl)-2-(4-fluorophenyl)acetamide;
2-(1-adamantyl)-N-(5,8-difluoro-1-oxo-4-phenylphthalazin-2(1H)-yl)acetamide;
2-(4-chlorophenyl)-N-(5,8-difluoro-1-oxo-4-phenylphthalazin-2(1H)-yl)acetamide;
2-(1-adamantyl)-N-(1-oxo-4-phenylphthalazin-2(1H)-yl)acetamide;

2-(3,5-difluorophenyl)-N-(1-oxo-4-phenylphthalazin-2(1H)-yl)acetamide;
N-(4-chloro-1-oxophthalazin-2(1H)-yl)-2-(3,5-difluorophenyl)acetamide;
2-(1-adamantyl)-N-(4-chloro-1-oxophthalazin-2(1H)-yl)acetamide;
N-(4-chloro-1-oxophthalazin-2(1H)-yl)-2-(4-chlorophenyl)acetamide;
2-(4-chlorophenyl)-N-(4-cyclopropyl-1-oxophthalazin-2(1H)-yl)acetamide;
N-(4-cyclopropyl-1-oxophthalazin-2(1H)-yl)-2-(3,5-difluorophenyl)acetamide;
2-(1-adamantyl)-N-(4-cyclopropyl-1-oxophthalazin-2(1H)-yl)acetamide;
2-(2,3-difluorophenyl)-N-(1-oxo-4-phenylphthalazin-2(1H)-yl)acetamide;
2-(4-fluorophenyl)-N-(1-oxo-4-phenylphthalazin-2(1H)-yl)acetamide;
2-(2,5-difluorophenyl)-N-(1-oxo-4-phenylphthalazin-2(1H)-yl)acetamide;
2-(4-chlorophenyl)-N-(4-methyl-1-oxophthalazin-2(1H)-yl)acetamide;
2-[3,5-dimethyl-1-adamantyl]-N-(4-isopropyl-1-oxophthalazin-2(1H)-yl)acetamide;
2-(3,5-difluorophenyl)-N-(6-fluoro-1-oxo-4-phenylphthalazin-2(1H)-yl)acetamide;
2-(4-chlorophenyl)-N-(6-fluoro-1-oxo-4-phenylphthalazin-2(1H)-yl)acetamide;
2-(1-adamantyl)-N-(6-fluoro-1-oxo-4-phenylphthalazin-2(1H)-yl)acetamide;
2-(3,5-difluorophenyl)-N-(4-methyl-1-oxophthalazin-2(1H)-yl)acetamide;
2-[1-(4-chlorophenyl)cyclopropyl]-N-[1-oxo-4-(trifluoromethyl)phthalazin-2(1H)-yl]acetamide;
2-[1-(4-chlorophenyl)cyclobutyl]-N-[1-oxo-4-(trifluoromethyl)phthalazin-2(1H)-yl]acetamide;
2-(2-naphthyl)-N-[1-oxo-4-(trifluoromethyl)phthalazin-2(1H)-yl]acetamide;
3-(4-chlorophenyl)-3-methyl-N-[1-oxo-4-(trifluoromethyl)phthalazin-2(1H)-yl]butanamide;
2-cyclopentyl-N-[1-oxo-4-(trifluoromethyl)phthalazin-2(1H)-yl]acetamide;
2,2-difluoro-N-[1-oxo-4-(trifluoromethyl)phthalazin-2(1H)-yl]-2-phenylacetamide;
2-cyclobutyl-N-[1-oxo-4-(trifluoromethyl)phthalazin-2(1H)-yl]acetamide;
N-[1-oxo-4-(trifluoromethyl)phthalazin-2(1H)-yl]-2-[4-(trifluoromethyl)phenyl]acetamide;
2-[4-(dimethylamino)phenyl]-N-[1-oxo-4-(trifluoromethyl)phthalazin-2(1H)-yl]acetamide;
3,3-dimethyl-N-[1-oxo-4-(trifluoromethyl)phthalazin-2(1H)-yl]butanamide;
2-[4-(methylsulfonyl)phenyl]-N-[1-oxo-4-(trifluoromethyl)phthalazin-2(1H)-yl]acetamide;
N-[1-oxo-4-(trifluoromethyl)phthalazin-2(1H)-yl]-3-phenylpropanamide;
N-[1-oxo-4-(trifluoromethyl)phthalazin-2(1H)-yl]-2-(1-phenylcyclopropyl)acetamide;
3-methyl-N-[1-oxo-4-(trifluoromethyl)phthalazin-2(1H)-yl]-3-phenylbutanamide;
N-[1-oxo-4-(trifluoromethyl)phthalazin-2(1H)-yl]-2-(3-thienyl)acetamide;
N-[1-oxo-4-(trifluoromethyl)phthalazin-2(1H)-yl]-2-(2-thienyl)acetamide;
2-(5-chloro-2-thienyl)-N-[1-oxo-4-(trifluoromethyl)phthalazin-2(1H)-yl]acetamide;
2-(5-methyl-2-thienyl)-N-[1-oxo-4-(trifluoromethyl)phthalazin-2(1H)-yl]acetamide;
N-[1-oxo-4-(trifluoromethyl)phthalazin-2(1H)-yl]-2-phenylacetamide;
(±)-2-(exo-bicyclo[2.2.1]heptan-2-yl)-N-[1-oxo-4-(trifluoromethyl)phthalazin-2(1H)-yl]acetamide;
2-(4-chloro-3-fluorophenyl)-N-[1-oxo-4-(trifluoromethyl)phthalazin-2(1H)-yl]acetamide;
2-(3-fluoroadamantan-1-yl)-N-(4-isopropyl-1-oxophthalazin-2(1H)-yl)acetamide;
2-(3-hydroxyadamantan-1-yl)-N-(4-isopropyl-1-oxophthalazin-2(1H)-yl)acetamide;
N-(4-tert-butyl-1-oxophthalazin-2(1H)-yl)-2-cyclopentylacetamide;
(±)-2-(exo-bicyclo[2.2.1]heptan-2-yl)-N-(4-tert-butyl-1-oxophthalazin-2(1H)-yl)acetamide;
N-(4-tert-butyl-1-oxophthalazin-2(1H)-yl)-3-methyl-3-phenylbutanamide;
N-(4-tert-butyl-1-oxophthalazin-2(1H)-yl)-2-(4-chlorophenyl)acetamide;
2-[(1S,2S,4R)-bicyclo[2.2.1]hept-2-yl]-N-(4-cyclobutyl-1-oxophthalazin-2(1H)-yl)acetamide;
2-[(1S,2S,4S)-bicyclo[2.2.1]hept-5-en-2-yl]-N-(4-cyclobutyl-1-oxophthalazin-2(1H)-yl)acetamide;
(±)-2-(exo-bicyclo[2.2.1]heptan-2-yl)-N-(4-cyclobutyl-1-oxophthalazin-2(1H)-yl)acetamide;
N-(4-cyclobutyl-1-oxophthalazin-2(1H)-yl)-2-(3,5-difluorophenyl)acetamide;
2-(4-chlorophenyl)-N-(4-cyclobutyl-1-oxophthalazin-2(1H)-yl)acetamide;
(±)-2-(exo-bicyclo[2.2.1]heptan-2-yl)-N-(4-cyclopentyl-1-oxophthalazin-2(1H)-yl)acetamide;
2-(4-chlorophenyl)-N-(4-cyclopentyl-1-oxophthalazin-2(1H)-yl)acetamide;
N-(4-cyclopentyl-1-oxophthalazin-2(1H)-yl)-2-(3,5-difluorophenyl)acetamide;
(±)-2-(exo-bicyclo[2.2.1]heptan-2-yl)-N-(4-cyclohexyl-1-oxophthalazin-2(1H)-yl)acetamide;
2-(adamantan-1-yl)-N-(4-cyclohexyl-1-oxophthalazin-2(1H)-yl)acetamide;
2-(4-chlorophenyl)-N-(4-cyclohexyl-1-oxophthalazin-2(1H)-yl)acetamide;
N-(4-cyclohexyl-1-oxophthalazin-2(1H)-yl)-2-(3,5-difluorophenyl)acetamide;
(±)-4-(3-{[(exo-bicyclo[2.2.1]heptan-2-yl)acetyl]amino}-4-oxo-3,4-dihydrophthalazin-1-yl)benzoic acid;
(±)-methyl 4-(3-{[exo-bicyclo[2.2.1]hept-2-ylacetyl]amino}-4-oxo-3,4-dihydrophthalazin-1-yl)benzoate;
methyl 4-(3-{[(4-chlorophenyl)acetyl]amino}-4-oxo-3,4-dihydrophthalazin-1-yl)benzoate;
(±)-4-(3-{[exo-bicyclo[2.2.1]hept-2-ylacetyl]amino}-4-oxo-3,4-dihydrophthalazin-1-yl)-N,N-dimethylbenzamide;
3-methyl-N-(1-oxo-4-phenylphthalazin-2(1H)-yl)-3-phenylbutanamide;
2-(2,4-dichlorophenyl)-N-(1-oxo-4-phenylphthalazin-2(1H)-yl)acetamide;
(±)-2-(exo-bicyclo[2.2.1]heptan-2-yl)-N-[4-(4-bromophenyl)-1-oxophthalazin-2(1H)-yl]acetamide;
N-[4-(4-bromophenyl)-1-oxophthalazin-2(1H)-yl]-3-methyl-3-phenylbutanamide;
N-[4-(4-chlorophenyl)-1-oxophthalazin-2(1H)-yl]-2-(1-methylcyclopentyl)acetamide;
N-[4-(4-chlorophenyl)-1-oxophthalazin-2(1H)-yl]-2-[1-(trifluoromethyl)cyclopentyl]acetamide;

N-[4-(4-chlorophenyl)-1-oxophthalazin-2(1H)-yl]-2-[(1S,2S,5R)-3,3-difluoro-6,6-dimethylbicyclo[3.1.1]hept-2-yl]acetamide;
N-[4-(4-chlorophenyl)-1-oxophthalazin-2(1H)-yl]-3-methyl-3-phenylbutanamide;
N-[4-(4-chlorophenyl)-1-oxophthalazin-2(1H)-yl]-2-fluoro-2-phenylacetamide;
N-[4-(4-chlorophenyl)-1-oxophthalazin-2(1H)-yl]-2-phenylacetamide;
N-[4-(4-chlorophenyl)-1-oxophthalazin-2(1H)-yl]-2-(morpholin-4-yl)acetamide;
N-[4-(4-chlorophenyl)-1-oxophthalazin-2(1H)-yl]-2-(pyridin-3-yl)acetamide;
N-[4-(4-chlorophenyl)-1-oxophthalazin-2(1H)-yl]-2-(pyridin-2-yl)acetamide;
N-[4-(4-chlorophenyl)-1-oxophthalazin-2(1H)-yl]-2-(3,4-dichlorophenyl)acetamide;
N-[4-(4-chlorophenyl)-1-oxophthalazin-2(1H)-yl]-2-(3,5-dimethoxyphenyl)acetamide;
N-[4-(4-chlorophenyl)-1-oxophthalazin-2(1H)-yl]-2-(3,5-dimethylphenyl)acetamide;
N-[4-(4-chlorophenyl)-1-oxophthalazin-2(1H)-yl]-2-[3-(trifluoromethoxy)phenyl]acetamide;
N-[4-(4-chlorophenyl)-1-oxophthalazin-2(1H)-yl]-2-[4-(trifluoromethyl)phenyl]acetamide;
N-[4-(4-chlorophenyl)-1-oxophthalazin-2(1H)-yl]-2-[3-(trifluoromethyl)phenyl]acetamide;
N-[4-(4-chlorophenyl)-1-oxophthalazin-2(1H)-yl]-2-[4-(dimethylamino)phenyl]acetamide;
2-(4-bromophenyl)-N-[4-(4-chlorophenyl)-1-oxophthalazin-2(1H)-yl]acetamide;
2-(3-chlorophenyl)-N-[4-(4-chlorophenyl)-1-oxophthalazin-2(1H)-yl]acetamide;
N-[4-(4-chlorophenyl)-1-oxophthalazin-2(1H)-yl]-2-(4-methoxyphenyl)acetamide;
N-[4-(4-chlorophenyl)-1-oxophthalazin-2(1H)-yl]-2-(3-methoxyphenyl)acetamide;
N-[4-(4-chlorophenyl)-1-oxophthalazin-2(1H)-yl]-2-(4-hydroxyphenyl)acetamide;
N-[4-(4-chlorophenyl)-1-oxophthalazin-2(1H)-yl]-2-(4-methylphenyl)acetamide;
N-[4-(4-chlorophenyl)-1-oxophthalazin-2(1H)-yl]-2-(3-methylphenyl)acetamide;
N-[4-(4-chlorophenyl)-1-oxophthalazin-2(1H)-yl]-2-cyclopentylacetamide;
N-[4-(4-chlorophenyl)-1-oxophthalazin-2(1H)-yl]-4-methylpentanamide;
N-[4-(4-chlorophenyl)-1-oxophthalazin-2(1H)-yl]-2-[4-(methylsulfonyl)phenyl]acetamide;
N-[4-(4-chlorophenyl)-1-oxophthalazin-2(1H)-yl]-2-(5-chloro-2-thienyl)acetamide;
(±)-2-(exo-bicyclo[2.2.1]hept-2-yl)-N-[4-(4-chlorophenyl)-1-oxophthalazin-2(1H)-yl]acetamide;
2-(4-chloro-3-fluorophenyl)-N-[4-(4-chlorophenyl)-1-oxophthalazin-2(1H)-yl]acetamide;
N-[4-(4-chlorophenyl)-1-oxophthalazin-2(1H)-yl]-2-[(1S,2S,5S)-6,6-dimethylbicyclo[3.1.1]hept-2-yl]acetamide;
2-(adamantan-1-yl)-N-[4-(4-chlorophenyl)-1-oxophthalazin-2(1H)-yl]acetamide;
2-(4-chlorophenyl)-N-[4-(4-chlorophenyl)-1-oxophthalazin-2(1H)-yl]acetamide;
N-[4-(4-chlorophenyl)-1-oxophthalazin-2(1H)-yl]-2-(3,5-difluorophenyl)acetamide;
N-[4-(4-chlorophenyl)-1-oxophthalazin-2(1H)-yl]-2-(1-phenylcyclopentyl)acetamide;
N-[4-(4-chlorophenyl)-1-oxophthalazin-2(1H)-yl]-2-phenylcyclopropanecarboxamide;
N-[4-(4-chlorophenyl)-1-oxophthalazin-2(1H)-yl]-2-(2-naphthyl)acetamide;
N-[4-(4-chlorophenyl)-1-oxophthalazin-2(1H)-yl]-2-(1-naphthyl)acetamide;
N-[4-(4-chlorophenyl)-1-oxophthalazin-2(1H)-yl]-4,4,4-trifluorobutanamide;
N-[4-(4-chlorophenyl)-1-oxophthalazin-2(1H)-yl]-3,3,3-trifluoropropanamide;
(±)-2-(exo-bicyclo[2.2.1]hept-2-yl)-N-[4-(3-chlorophenyl)-1-oxophthalazin-2(1H)-yl]acetamide;
2-(adamantan-1-yl)-N-[4-(3-chlorophenyl)-1-oxophthalazin-2(1H)-yl]acetamide;
2-(4-chlorophenyl)-N-[4-(3-chlorophenyl)-1-oxophthalazin-2(1H)-yl]acetamide;
N-[4-(3-chlorophenyl)-1-oxophthalazin-2(1H)-yl]-2-(3,5-difluorophenyl)acetamide;
2-[(1S,2S,4R)-bicyclo[2.2.1]hept-2-yl]-N-[4-(4-fluorophenyl)-1-oxophthalazin-2(1H)-yl]acetamide;
2-[(1S,2S,4S)-bicyclo[2.2.1]hept-5-en-2-yl]-N-[4-(4-fluorophenyl)-1-oxophthalazin-2(1H)-yl]acetamide;
(±)-2-(exo-bicyclo[2.2.1]hept-2-yl)-N-[4-(4-fluorophenyl)-1-oxophthalazin-2(1H)-yl]acetamide;
2-(4-chlorophenyl)-N-[4-(4-fluorophenyl)-1-oxophthalazin-2(1H)-yl]acetamide;
2-(3,5-difluorophenyl)-N-[4-(4-fluorophenyl)-1-oxophthalazin-2(1H)-yl]acetamide;
(±)-2-(exo-bicyclo[2.2.1]hept-2-yl)-N-[4-(2,4-difluorophenyl)-1-oxophthalazin-2(1H)-yl]acetamide;
2-(4-chlorophenyl)-N-[4-(4-methylphenyl)-1-oxophthalazin-2(1H)-yl]acetamide;
2-(3,5-difluorophenyl)-N-[4-(4-methylphenyl)-1-oxophthalazin-2(1H)-yl]acetamide;
2-[(1S,2S,5S)-6,6-dimethylbicyclo[3.1.1]hept-2-yl]-N-[4-(4-methylphenyl)-1-oxophthalazin-2(1H)-yl]acetamide;
2-(adamantan-1-yl)-N-[4-(4-methylphenyl)-1-oxophthalazin-2(1H)-yl]acetamide;
N-(4-benzyl-1-oxophthalazin-2(1H)-yl)-2-[1-(trifluoromethyl)cyclopentyl]acetamide;
N-(4-benzyl-1-oxophthalazin-2(1H)-yl)-3-methyl-3-phenylbutanamide;
(±)—N-(4-benzyl-1-oxophthalazin-2(1H)-yl)-2-(exo-bicyclo[2.2.1]hept-2-yl)acetamide;
N-(4-benzyl-1-oxophthalazin-2(1H)-yl)-2-(4-chlorophenyl)acetamide;
N-(4-benzyl-1-oxophthalazin-2(1H)-yl)-2-(3,5-difluorophenyl)acetamide;
(±)-2-(exo-bicyclo[2.2.1]hept-2-yl)-N-[4-(4-chlorobenzyl)-1-oxophthalazin-2(1H)-yl]acetamide;
N-[4-(4-chlorobenzyl)-1-oxophthalazin-2(1H)-yl]-2-(4-chlorophenyl)acetamide;
N-[4-(4-chlorobenzyl)-1-oxophthalazin-2(1H)-yl]-2-(3,5-difluorophenyl)acetamide;
2-[(1S,2S,4R)-bicyclo[2.2.1]hept-2-yl]-N-{1-oxo-4-[4-(trifluoromethyl)phenyl]phthalazin-2(1H)-yl}acetamide;
3-methyl-N-{1-oxo-4-[4-(trifluoromethyl)phenyl]phthalazin-2(1H)-yl}-3-phenylbutanamide;
2-(adamantan-1-yl)-N-{1-oxo-4-[4-(trifluoromethyl)phenyl]phthalazin-2(1H)-yl}acetamide;
(±)-2-(exo-bicyclo[2.2.1]hept-2-yl)-N-{1-oxo-4-[4-(trifluoromethyl)phenyl]phthalazin-2(1H)-yl}acetamide;
(±)-2-(exo-bicyclo[2.2.1]hept-2-yl)-N-[4-(4-methoxyphenyl)-1-oxophthalazin-2(1H)-yl]acetamide;

N-[4-(4-methoxyphenyl)-1-oxophthalazin-2(1H)-yl]-2-(4-methylcyclohexyl)acetamide;
2-(3,5-difluorophenyl)-N-[4-(4-methoxyphenyl)-1-oxophthalazin-2(1H)-yl]acetamide;
2-(adamantan-1-yl)-N-[4-(4-methoxyphenyl)-1-oxophthalazin-2(1H)-yl]acetamide;
(±)-2-(exo-bicyclo[2.2.1]hept-2-yl)-N-[4-(2,5-dimethylphenyl)-1-oxophthalazin-2(1H)-yl]acetamide;
2-(adamantan-1-yl)-N-[4-(2,5-dimethylphenyl)-1-oxophthalazin-2(1H)-yl]acetamide;
2-(4-chlorophenyl)-N-[4-(2,5-dimethylphenyl)-1-oxophthalazin-2(1H)-yl]acetamide;
2-(3,5-difluorophenyl)-N-[4-(2,5-dimethylphenyl)-1-oxophthalazin-2(1H)-yl]acetamide;
2-[(1S,2S,4S)-bicyclo[2.2.1]hept-5-en-2-yl]-N-[4-(2,4-dimethylphenyl)-1-oxophthalazin-2(1H)-yl]acetamide;
(±)-2-(exo-bicyclo[2.2.1]hept-2-yl)-N-[4-(2,4-dimethylphenyl)-1-oxophthalazin-2(1H)-yl]acetamide;
2-(4-chlorophenyl)-N-[4-(2,4-dimethylphenyl)-1-oxophthalazin-2(1H)-yl]acetamide;
2-(3,5-difluorophenyl)-N-[4-(2,4-dimethylphenyl)-1-oxophthalazin-2(1H)-yl]acetamide;
(±)-2-(exo-bicyclo[2.2.1]hept-2-yl)-N-[4-(3,4-dimethylphenyl)-1-oxophthalazin-2(1H)-yl]acetamide;
2-(adamantan-1-yl)-N-[4-(3,4-dimethylphenyl)-1-oxophthalazin-2(1H)-yl]acetamide;
2-(4-chlorophenyl)-N-[4-(3,4-dimethylphenyl)-1-oxophthalazin-2(1H)-yl]acetamide;
2-(3,5-difluorophenyl)-N-[4-(3,4-dimethylphenyl)-1-oxophthalazin-2(1H)-yl]acetamide;
(±)-2-(exo-bicyclo[2.2.1]hept-2-yl)-N-[1-oxo-4-(2-phenylethyl)phthalazin-2(1H)-yl]acetamide;
(±)-2-(exo-bicyclo[2.2.1]hept-2-yl)-N-[4-(4-isopropylphenyl)-1-oxophthalazin-2(1H)-yl]acetamide;
2-(adamantan-1-yl)-N-[4-(4-isopropylphenyl)-1-oxophthalazin-2(1H)-yl]acetamide;
2-(4-chlorophenyl)-N-[4-(4-isopropylphenyl)-1-oxophthalazin-2(1H)-yl]acetamide;
2-(3,5-difluorophenyl)-N-[4-(4-isopropylphenyl)-1-oxophthalazin-2(1H)-yl]acetamide;
(±)-2-(exo-bicyclo[2.2.1]hept-2-yl)-N-[1-oxo-4-(1-phenylcyclopropyl)phthalazin-2(1H)-yl]acetamide;
2-(adamantan-1-yl)-N-[4-isopropyl-1-oxo-7-(trifluoromethyl)phthalazin-2(1H)-yl]acetamide;
2-(adamantan-1-yl)-N-[7-bromo-4-(4-methoxyphenyl)-1-oxophthalazin-2(1H)-yl]acetamide;
2-(adamantan-1-yl)-N-[6-bromo-4-(4-methoxyphenyl)-1-oxophthalazin-2(1H)-yl]acetamide;
N-[6-bromo-4-(4-methoxyphenyl)-1-oxophthalazin-2(1H)-yl]-2-(3,5-difluorophenyl)acetamide;
N-[7-bromo-4-(4-methoxyphenyl)-1-oxophthalazin-2(1H)-yl]-2-(3,5-difluorophenyl)acetamide;
N-[4-(4-chlorophenyl)-5,8-difluoro-1-oxophthalazin-2(1H)-yl]-2-(3,5-difluorophenyl)acetamide;
2-(4-chlorophenyl)-N-[4-(4-chlorophenyl)-5,8-difluoro-1-oxophthalazin-2(1H)-yl]acetamide;
2-(adamantan-1-yl)-N-[4-(4-chlorophenyl)-5,8-difluoro-1-oxophthalazin-2(1H)-yl]acetamide;
(±)-2-(exo-bicyclo[2.2.1]hept-2-yl)-N-[4-(4-chlorophenyl)-5,8-difluoro-1-oxophthalazin-2(1H)-yl]acetamide;
2-(adamantan-1-yl)-N-(1-oxo-4-phenyl-5,6,7,8-tetrahydrophthalazin-2(1H)-yl)acetamide;
2-(3,5-difluorophenyl)-N-(1-oxo-4-phenyl-5,6,7,8-tetrahydrophthalazin-2(1H)-yl)acetamide;
2-(4-chlorophenyl)-N-(1-oxo-4-phenyl-5,6,7,8-tetrahydrophthalazin-2(1H)-yl)acetamide;
2-(3,5-difluorophenyl)-N-(1-oxo-4-phenyl-1,5,6,7-tetrahydro-2H-cyclopenta[d]pyridazin-2-yl)acetamide;
2-(adamantan-1-yl)-N-(1-oxo-4-phenyl-1,5,6,7-tetrahydro-2H-cyclopenta[d]pyridazin-2-yl)acetamide;
2-(4-chlorophenyl)-N-(1-oxo-4-phenyl-1,5,6,7-tetrahydro-2H-cyclopenta[d]pyridazin-2-yl)acetamide;
2-(methylthio)-N-[1-oxo-4-(trifluoromethyl)phthalazin-2(1H)-yl]acetamide;
2-(adamantan-1-ylthio)-N-[1-oxo-4-(trifluoromethyl)phthalazin-2(1H)-yl]acetamide;
2-(adamantan-1-ylthio)-N-(1-oxo-4-phenylphthalazin-2(1H)-yl)acetamide; and
2-(1,3-benzodioxol-5-yl)-N-[4-(4-chlorophenyl)-1-oxophthalazin-2(1H)-yl]acetamide.

18. A pharmaceutical composition comprising a therapeutically effective amount of a compound of formula (I) according to claim 1 or a pharmaceutically acceptable salt thereof, in combination with one or more pharmaceutically acceptable carriers.

19. The pharmaceutical composition according to claim 18 further comprising one or more analgesic or one or more nonsteroidal anti-inflammatory drug, or a combination thereof.

20. The pharmaceutical composition according to claim 19 wherein the nonsteroidal anti-inflammatory drug is ibuprofen.

21. A method for treating pain in a subject in need of such treatment comprising administering to the subject a therapeutically effective amount of a compound of formula (I) according to claim 1, or a pharmaceutically acceptable salt thereof, alone or in combination with one or more pharmaceutically acceptable carrier.

22. The method according to claim 21 further comprising the step of co-administering with one or more analgesics, or with one or more nonsteroidal anti-inflammatory drug, or combination thereof.

23. The method according to claim 22 wherein the nonsteroidal anti-inflammatory drug is ibuprofen.

* * * * *